US011655253B2

(12) United States Patent
Ruan

(10) Patent No.: US 11,655,253 B2
(45) Date of Patent: May 23, 2023

(54) CBP/CATENIN SIGNALING PATHWAY INHIBITORS AND USES THEREOF

(71) Applicant: 3+2 Pharma, LLC, Lewes, DE (US)

(72) Inventor: Fuqiang Ruan, Bellevue, WA (US)

(73) Assignee: 3+2 PHARMA, LLC, Lewes, DE (US)

( * ) Notice: Subject to any disclaimer, the term of this patent is extended or adjusted under 35 U.S.C. 154(b) by 170 days.

(21) Appl. No.: 17/199,304

(22) Filed: Mar. 11, 2021

(65) Prior Publication Data

US 2021/0317123 A1    Oct. 14, 2021

Related U.S. Application Data

(60) Provisional application No. 62/988,827, filed on Mar. 12, 2020.

(51) Int. Cl.
| | | |
|---|---|---|
| C07D 487/04 | (2006.01) | |
| A61P 17/08 | (2006.01) | |
| A61P 1/16 | (2006.01) | |
| A61P 11/00 | (2006.01) | |
| A61K 8/49 | (2006.01) | |
| A61K 9/00 | (2006.01) | |
| A61K 39/39 | (2006.01) | |
| A61K 45/06 | (2006.01) | |
| A61Q 19/08 | (2006.01) | |

(52) U.S. Cl.
CPC .......... *C07D 487/04* (2013.01); *A61K 8/4966* (2013.01); *A61K 9/0014* (2013.01); *A61K 39/39* (2013.01); *A61K 45/06* (2013.01); *A61P 1/16* (2018.01); *A61P 11/00* (2018.01); *A61P 17/08* (2018.01); *A61Q 19/08* (2013.01)

(58) Field of Classification Search
None
See application file for complete search history.

(56) References Cited

U.S. PATENT DOCUMENTS

| | | |
|---|---|---|
| 7,671,054 B1 | 3/2010 | Moon et al. |
| 9,371,330 B2 | 6/2016 | Kahn et al. |
| 2010/0029630 A1 | 2/2010 | Moon et al. |
| 2010/0286094 A1 | 11/2010 | Chung et al. |
| 2014/0051706 A1 | 2/2014 | Kouji et al. |
| 2015/0011759 A1 | 1/2015 | Christie et al. |
| 2015/0175615 A1 | 6/2015 | Inoue et al. |

OTHER PUBLICATIONS

International Preliminary Report on Patentability for International Application No. PCT/US2021/021958 dated Sep. 22, 2022, 7 pages.
International Preliminary Report on Patentability for International Application No. PCT/US2021/021952 dated Sep. 22, 2022, 6 pages.
Akbar et al., "Aging immunity may exacerbate COVID-19: Increased general inflammation in aging inhibits immunity and affects responses to infections" Science, vol. 369 Issue 6501, Jul. 17, 2020, pp. 256-257.
Akcora et al., "Inhibition of canonical WNT signaling pathway by B-catenin/CBP inhibitor ICG-001 ameliorates liver fibrosis in vivo through suppression of stromal CXCL12" BBA—Molecular Basis of Disease, vol. 1864, Dec. 5, 2017, pp. 804-818.
Anderson et al., "The effect of influenza vaccination for the elderly on hospitalization and mortality: an observational study with a regression discontinuity design" Annals of Internal Medicine, vol. 172, Mar. 3, 2020, pp. 445-452.
Spagnolo et al., "Pulmonary fibrosis secondary to COVID-19: a call to arms?" The Lancet Respiratory Medicine, vol. 8 Issue 8, May 15, 2020, pp. 750-752.
Borsa et al., "Modulation of asymmetric cell division as a mechanism to boost CD8+ T cell memory" Science Immunology, vol. 4 Issue 34, Apr. 12, 2019, pp. 1-15.
Ciocca et al., "Cutting edge: asymmetric memory t cell division in response to rechallenge" The Journal of Immunology, vol. 188 No. 9, Mar. 30, 2012, pp. 4145-4148.
Parmigiani et al., "Impaired antibody response to influenza vaccine in HIV-infected and uninfected aging women is associated with immune activation and inflammation" PLoS One, vol. 8 Issue 11, Nov. 13, 2013, pp. 1-13.
Emami et al., "A small molecule inhibitor of B-catenin/CREB-binding protein transcription" Proceedings of the National Academy of Sciences USA, vol. 101 No. 34, Aug. 24, 2004, pp. 12682-12687.
George et al., "Pulmonary fibrosis and COVID-19: the potential role for antifibrotic therapy" The Lancet Respiratory Medicine, vol. 8, May 15, 2020, pp. 807-815.
Ma et al., "Differential roles for the coactivators CBP and p300 on TCF/B-catenin-mediated survivin gene expression" Oncogene, vol. 24, Mar. 14, 2005, pp. 3619-3631.
Kahn, "Can we safely target the WNT pathway?" Nature Reviews Drug Discovery, vol. 13, Jul. 1, 2014, pp. 513-532.
Kim et al., "Activation of miR-21-Regulated pathways in immune aging selects against signatures characteristic of memory T cells" Cell Reports, vol. 25, Nov. 20, 2018, pp. 2148-2162.

(Continued)

*Primary Examiner* — Zinna Northington Davis
(74) *Attorney, Agent, or Firm* — Aikin & Gallant, LLP

(57) ABSTRACT

Provided are compounds of formula (Ia), (Ib) and (IIa), and pharmaceutically acceptable salts thereof. Additionally provided are compositions and pharmaceutical compositions comprising the compounds, therapeutic methods using same for modulating (e.g., inhibiting) CREB binding protein (CBP)/β-catenin mediated signaling in treating a condition, disease or disorder (e.g., fibrosis, cancer, neurological conditions, metabolic disorders (e.g., diabetes, etc.), and skin conditions (dermatitis, psoriasis, scarring, alopecia, etc.) mediated by aberrant CBP/β-catenin signaling, and cosmetic methods for treating skin conditions (e.g., aging, etc.). Additionally, provided are methods for enhancing vaccine efficacy using the compounds and compositions. Further provided are methods for efficiently synthesizing a clinical grade drug, comprising use, in a penultimate, or last reaction step under GMP conditions, of an intermediate 2-propynyl-compound to form a clinical grade isoxazole derivative (e.g., via 3+2 cycloaddition).

54 Claims, 11 Drawing Sheets

(56) References Cited

OTHER PUBLICATIONS

Kim et al., "CBP/Catenin antagonists: targeting LSCs' achilles heel" Experimental Hematology, vol. 52, May 4, 2017, pp. 1-11.
Kimura et al., "Safety, tolerability, and preliminary efficacy of the anti-fibrotic small molecule PRI-724, a CBP/B-Catenin inhibitor, in patients with hepatitis C virus-related cirrhosis: a single-center, open-label, dose escalation phase 1 trial" EBioMedicine, vol. 23, Aug. 19, 2017, pp. 79-87.
Kumar et al., "Preferential induction of EphB4 over EphB2 and its implication in colorectal cancer progression" Cancer Research, vol. 69 No 9, Apr. 14, 2009, pp. 3736-3745.
Ljungberg et al., "Functions of the WNT signaling network in shaping host responses to infection" Frontiers in Immunology, vol. 10, Nov. 2019, pp. 1-23.
Mannick et al., "TORC1 inhibition enhances immune function and reduces infections in the elderly" Science Translational Medicine, vol. 10 Issue 449, Jul. 11, 2018, pp. 1-10.
Mavigner et al., "Pharmacological modulation of the Wnt/B-Catenin pathway inhibits proliferation and promotes differentiation of long-lived memory CD4+ T cells in antiretroviral therapy-suppressed simian immunodeficiency virus-infected macaques" Journal of Virology, vol. 94 Issue 1, Dec. 12, 2019, pp. 1-15.
Merad et al., "Pathological inflammation in patients with COVID-19: a key role for monocytes and macrophages" Nature Reviews Immunology, vol. 20, May 6, 2020, pp. 355-362.
MORROT "Asymmetric cell division regulates the transcriptional balance controlling memory fate decisions in T cells" Annals of Translational Medicine, vol. 5, Mar. 1, 2017, pp. 1-2.
Hirakawa et al., "B-catenin signaling inhibitors ICG-001 and C-82 improve fibrosis in preclinical models of endometriosis" Scientific Reports, vol. 9, Dec. 27, 2019, pp. 1-11.
Shiozaki et al., "Discovery of (1S,2R,3R)-2,3-Dimethyl-2-phenyl-1-sulfamidocyclopropanecarboxylates: novel and highly selective aggrecanase inhibitors" Journal of Medicinal Chemistry, vol. 54, Mar. 21, 2011, pp. 2839-2863.
Slutsky et al., "Ventilator-induced lung injury" New England Journal of Medicine, vol. 369, Nov. 28, 2013, pp. 2126-2136.
Thomas et al., "Kat3 coactivators in somatic stem cells and cancer stem cells: biological roles, evolution and pharmacologic manipulation" Cell Biology and Toxicology, vol. 32, Mar. 23, 2016, pp. 61-81.
Veltri et al., "Concise review: Wnt signaling pathways in skin development and epidermal stem cells" Stem Cells Express, vol. 36, Oct. 19, 2017, pp. 22-35.
Verbist et al., "Metabolic maintenance of cell asymmetry following division in activated T lymphocytes" Nature, vol. 532, Apr. 21, 2016, pp. 389-404.
WILLYARD "Ageing and COVID vaccines" Nature, vol. 586, Oct. 15, 2020, pp. 352-354.
Xiao et al., "Wnt/B-catenin regulates blood pressure and kidney injury in rats" BBA—Molecular Basis of Disease, vol. 1865 Issue 6, Jan. 30, 2019, pp. 1313-1322.
Zhao et al., "An essential role for Wnt/B-catenin signaling in mediating hypertensive heart disease" Scientific Reports, vol. 8, Jun. 12, 2018, pp. 1-14.
International Search Report and Written Opinion for International Application No. PCT/US2021/021952 dated Jun. 2, 2021, 8 pages.
"PubChem-CID-140634489," <https://pubchem.ncbi.nlm.nih.gov/compound/140634489>, Dec. 6, 2019, 9 pages.
International Search Report and Written Opinion for International Application No. PCT/US2021/021958 dated Jul. 21, 2021, 10 pages.
Nusse et al., "Many Tumors Induced by the Mouse Mammary Tumor Virus Contain a Provirus Integrated in the Same Region of the Host Genome," Cell vol. 31, Nov. 1982; pp. 99-109.
Baker et al., "Molecular cloning of sequences from *wingless*, a segment polarity gene is *Drosophila*: the spatial distribution of a transcript in embryos," The EMBO Journal, vol. 6, No. 6, 1987, pp. 1765-1773.
Logan et al., "The Wnt Signaling Pathway in Development and Disease," Annu. Rev. Cell Dev. Biol. 2004, 20, pp. 781-810.
Van Amerongen et al., "Towards an integrated view of Wnt signaling in development," Development 136, 2009, pp. 3205-3214.
Alonso et al., "Stem cells in the skin: waste not, Wnt not," Genes & Development 17, 2003, pp. 1189-1200.
Pinto, et al., "Wnt control of stem cells and differentiation in the intestinal epithelium," Experimental Cell Research 306, (2005), 357-363.
Nemeth et al., "β-Catenin Expression in the Bone Marrow Microenvironment is Required for Long-Term Maintenance of Primitive Hematopoietic Cells," Stem Cells, 2009, 27, pp. 1109-1119.
Reya et al., "Wnt signaling in stem cells and cancer," Nature, vol. 434, Apr. 14, 2005, pp. 843-850.
Groden et al., "Identification and Characterization of the Familial Adenomatous Polyposis *Coli* Gene," Cell, vol. 66, Aug. 9, 1991, pp. 589-600.
Kinzler et al., "Identification of FAP Locus Genes from Chromosome 5q21," Science, vol. 253, Aug. 9, 1991; pp. 661-665.
Nishisho et al., "Mutations of Chromosome 5q21 Genes in FAP and Colorectal Cancer Patients," Science, vol. 253, Aug. 9, 1991; 253:, pp. 665-669.
Morin, et al., "Activation of β-Catenin-Tcf Signaling in Colon Cancer by Mutations in B-Catenin or APC," Science, vol. 275, Mar. 21, 1997, pp. 1787-1790.
Rubinfeld et al., "Stabilization of β-Catenin by Genetic Defects in Melanoma Cell Lines," Science, vol. 275, Mar. 21, 1997, pp. 1790-1792.
Herr et al., "WNT secretion and signalling in human disease," Trends in Molecular Medicine, vol. 18, No. 8, Aug. 2012, pp. 483-493.
Han, "Functional Genomic Studies: Insights into the Pathogenesis of Liver Cancer," Annual Rev. Genom. Hum. Genet., 2012, 13, pp. 171-205.
Sastre-Perona, et al., "Role of the Wnt pathway in thyroid cancer," Frontiers in Endocrinology (Lausanne), vol. 3, Article 31, Feb. 29, 2012, pp. 1-10.
Gatcliffe, et al., "Wnt signaling in ovarian tumorigenesis," Int. J. Gynecol. Cancer, 2008; 18(5): 954-962.
Caldwell et al., "The Wnt Antagonist sFRP1 in Colorectal Tumorigenesis," Cancer Research 64, Feb. 1, 2004, pp. 883-888.
Lee et al., "Expression of the secreted frizzled-related protein gene family is downregulated in human mesothelioma," Oncogene 23, 2004, pp. 6672-6676.
Zou et al., "Aberrant methylation of secreted frizzled-related protein genes in esophageal adenocarcinoma and Barrett's esophagus," Int. J. Cancer, vol. 116, 2005, pp. 584-591.
Rhee et al., "Wnt and frizzled receptors as potential targets for immunotherapy in head and neck squamous cell carcinomas," Oncogene 21, 2002, pp. 6598-6605.
Milovanovic et al., "Expression of Wnt genes and frizzled 1 and 2 receptors in normal breast epithelium and infiltrating breast carcinoma," International Journal of Oncology 25, 2004, pp. 1337-1342.
Okino et al., "Up-regulation and overproduction of DVL-1, the human counterpart of the *Drosophila* dishevelled gene, in cervical squamous cell carcinoma," Oncology Reports 10, 2003, pp. 1219-1223.
Uematsu et al., "Wnt Pathway Activation in Mesothelioma: Evidence of Dishevelled Overexpression and Transcriptional Activity of β-Catenin," Cancer Research 63, Aug. 1, 2003, pp. 4547-4551.
Uematsu et al., "Activation of the Wnt pathway in non small cell lunch cancer: evidence of dishevelled overexpression," Oncogene (2003) 22, pp. 7218-7221.
Tang et al., "Inhibition of CREB binding protein-beta-catenin signaling down regulates CD133 expression and activates PP2A-PTEN signaling in tumor initiating liver cancer cells," Cell Communication and Signaling, 2018, 16:9, pp. 1-12.
Higuchi et al., "Specific Direct Small Molecule p300/β-Catenin Antagonists Maintain Stem Cell Potency," Current Molecular Pharmacology, 2016, 9, pp. 272-279.
Ramirez-Montagut et al., "Immunity to melanoma: unraveling the relation of tumor immunity and autoimmunity," Oncogene (2003) 22, pp. 3180-3187.

(56) References Cited

OTHER PUBLICATIONS

Sawaya et al., "Risk of Cervical Cancer Associated with Extending the Interval between Cervical-Cancer Screenings," The New England Journal of Medicine, vol. 349, No. 16, Oct. 16, 2003, pp. 1501-1509.

Rosen et al., "Low membranous expression of β-catenin and high mitotic count predict poor prognosis in endometrioid carcinoma of the ovary," Modern Pathology (2010) 23, pp. 113-122.

Gregory et al., "Non-hematopoietic bone marrow stem cells: Molecular control of expansion and differentiation," Experimental Cell Research 306 (2005), pp. 330-335.

Fukui et al., "Transcriptional silencing of secreted frizzled related protein 1 (SFRP1) by promoter hypermethylation in non-small lung cancer," Oncogene (2005) 24, pp. 6323-6327.

A

B C

D E

CBP/CATENIN SIGNALING PATHWAY INHIBITORS AND USES THEREOF

CROSS-REFERENCE TO RELATED APPLICATION

This application claims the benefit of priority to U.S. Provisional Patent Application Ser. No. 62/988,827, filed Mar. 12, 2020, which is hereby incorporated by reference in its entirety.

FIELD

Aspects of the invention relate generally to modulation of the Wnt/β-catenin pathway in mammalian (both human and non-human) cells and tissues, more particularly to small molecule inhibitors of CREB binding protein (CBP)/β-catenin signaling, and even more particularly to surprisingly active and bioavailable small molecule CBP/β-catenin inhibitors having broad utility for modulating and treating CBP/β-catenin signaling-mediated conditions and disorders, including but not limited to one or more of fibrosis, cancer, neurological disorders, metabolic disorders (including diabetes and fatty liver disease, e.g., alcoholic (ALD) and non-alcoholic hepatic steatosis (ALD and NAFLD, respectively), and including non-alcoholic steatohepatitis (NASH)), skin conditions (e.g., dermatitis, psoriasis, alopecia, aging etc.), wound healing, aging, and optionally further including one or more of pulmonary hypertension, congestive heart failure, chronic kidney disease, renal fibrosis, endometriosis, cardiac fibrosis, polycystic ovary syndrome (PCOS), and/or systemic fibrosis/scleroderma. Additional aspects relate to enhancing vaccine efficacy using the disclosed compounds and compositions.

BACKGROUND

The evolutionarily conserved Wnt/β-catenin signaling pathway plays fundamental and essential roles in both embryonic development and adult homeostasis. Additionally, given the established and critical roles of dysregulated/hyperactive CBP/β-catenin signaling in fibrosis, cancer, neurological disorders, skin disorders, and metabolic disorders (including diabetes and fatty liver disease) and aging, and in other Wnt/β-catenin-mediated conditions and disorders, there has been considerable interest in pursuing both therapeutic and cosmetic intervention by modulating (e.g., inhibiting) the CBP/β-catenin signaling, and/or increasing p300/β-catenin signaling, preferably using small molecule inhibitors of the CBP/β-catenin interaction. Developing specific small molecule inhibitors of the CBP/β-catenin interaction that are both sufficiently active and bioavailable (preferably orally available in many instances for therapeutic applications), however, remains a challenge that has, until now, substantially impeded realization of their therapeutic and cosmeceutical potential.

SUMMARY

Aspects of the present invention are directed to compounds, for example including small molecule inhibitors of the CBP/β-catenin interaction that are both sufficiently active and bioavailable, along with compositions, pharmaceutical compositions comprising the compounds, and methods for synthesizing and using the compounds and compositions, both therapeutically and cosmeceutically, as further described below.

Aspects of the invention may include a compound of formula (Ia):

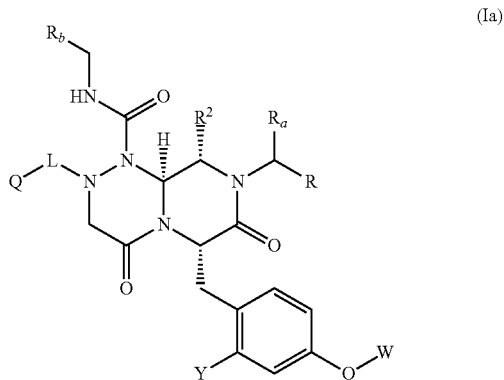

(Ia)

and pharmaceutically acceptable salts thereof, wherein:

$R_a$ is hydrogen or —$CH_3$;

$R_b$ is a monocyclic aryl group having 5 to 7 ring members, which may have 1 to 2 heteroatoms selected from nitrogen, oxygen or sulfur, and which may have one or more substituents selected from a group consisting of halide, cyano, and lower alkyl;

R is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group; or a bicyclic aryl group, or substituted bicyclic aryl, having 8 to 11 ring members, which may have 1 to 3 heteroatoms selected from nitrogen, oxygen or sulfur, where the substituted bicyclic aryl ring may have one or more substituents independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group;

$R^2$ is hydrogen, or —$CH_3$;

Y is selected from: hydrogen, deuterium, or halogen;

W is hydrogen, phosphate or phosphate salt, an ester of an alkyl acid or of a fatty acid, or X, wherein X is selected from:

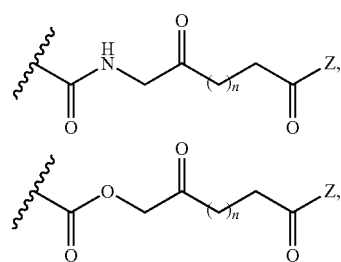

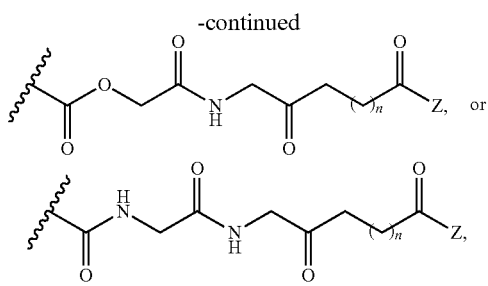

wherein Z is OR₄ where R₄ is hydrogen or $C_1$-$C_6$ alkyl, or Z is an amino acid or amino acid ester, and n is 1 or 2;

L is —CH₂—, —CF₂—, or —C(CH₃)₂—; and

Q is a 5- or 6-membered nitrogen-containing heterocycle substituted by 0-2 substituents, selected from:

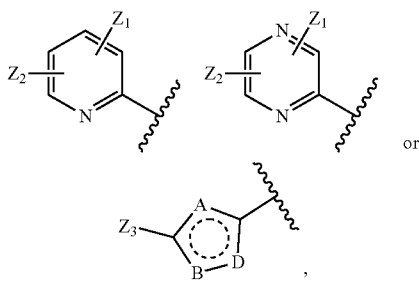

wherein A, B, and D are independently selected from O, S, N, or —CH, wherein $Z_1$, $Z_2$ are independently selected from hydrogen, deuterium, halogen, $C_1$-$C_4$ alkyl, —OH, —O$C_1$-$C_6$ alkyl, and

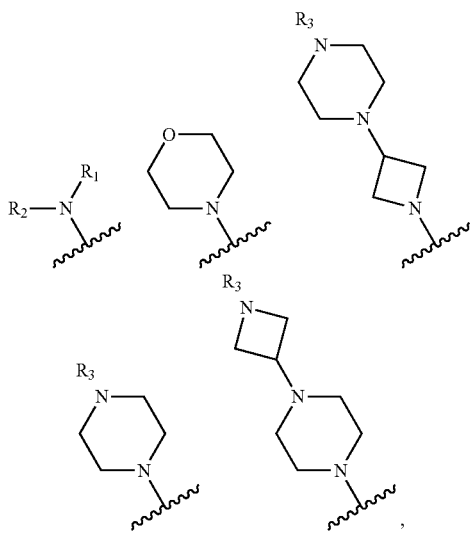

wherein $R_1$, $R_2$ and $R_3$ are independently selected from hydrogen, $C_1$-$C_6$ alkyl, or $C_1$-$C_6$ alkyl containing one or more —OH, and wherein $Z_3$ is selected from hydrogen, halogen, or a direct-bonded, or —NH-linked, —O$C_1$-$C_3$ alkyl linked, or —NH$C_1$-$C_3$ alkyl linked aryl, heteroaryl, cycloalkyl, heterocycloalkyl, or a nitrogen-bonded cycloalkyl, heterocycloalkyl, or —NH$C_1$-$C_4$ alkyl, —N($C_1$-$C_4$ alkyl)₂, each of which is substituted by 0-4 substituents independently selected from hydrogen, deuterium, halogen, $C_1$-$C_4$ alkyl, $C_1$-$C_3$ haloalkyl, —OH, —O$C_1$-$C_4$ alkyl, —O$C_1$-$C_6$ alkyl-C(O)NH—OH, —NH₂, —C(O)NH—$C_1$-$C_6$ alkyl-heteroaryl, —NHC(O)$C_1$-$C_6$ alkyl-C(O)NH—OH, heteroaryl, cycloalkyl, heterocycloalkyl, or a nitrogen-bonded cycloalkyl or heterocycloalkyl, —NH$C_1$-$C_4$ alkyl, or —N($C_1$-$C_4$ alkyl)₂.

In some aspects, the ester of the alkyl acid or of the fatty acid is selected from:

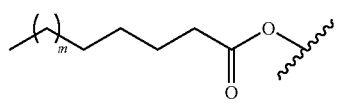

wherein m is 1 to 14,

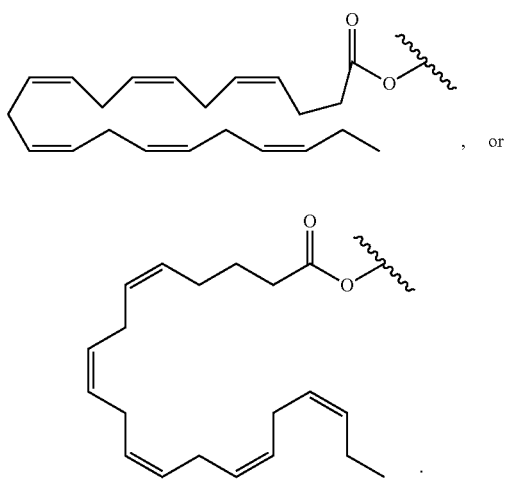

In some aspects, R is a bicyclic aryl selected from naphthyl, quinolinyl, isoquinolinyl, quinoxaline, phthalazine, quinazoline, cinnoline, or naphthyridine, or substituted variants thereof.

In some aspects, the compound is of the formula (Ib):

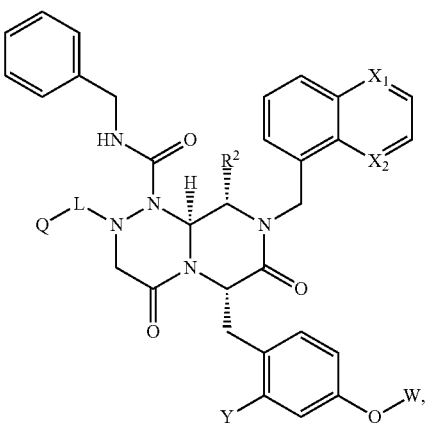

(Ib)

wherein $X_1$ and $X_2$ are independently selected from: N, or —CH.

In some aspects, L is —CH$_2$—;
Q is

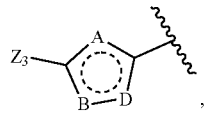

wherein A, B, and D are independently selected from O, S, N, or —CH.

In some aspects, A is —CH, B is N, and D is O (Q is Z$_3$-isoxazole-), and wherein W is hydrogen, phosphate or phosphate salt, an ester of an alkyl acid or of a fatty acid, or X, wherein X is selected from:

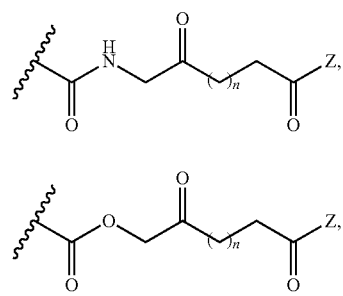

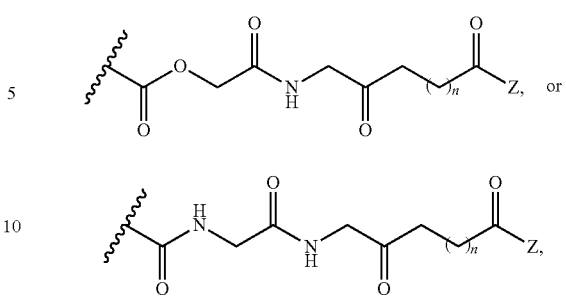

wherein Z is OR$_4$ where R$_4$ is hydrogen or C$_1$-C$_6$ alkyl, or Z is an amino acid or amino acid ester, and n is 1 or 2.

In some aspects, Z$_3$ is selected from aryl or heteroaryl, each of which is substituted by 0-4 substituents independently selected from hydrogen, deuterium, halogen, C$_1$-C$_4$ alkyl, C$_1$-C$_3$ haloalkyl, —OH, —OC$_1$-C$_6$ alkyl, —OC$_1$-C$_6$alkyl-C(O)NH—OH, —NH$_2$, —C(O)NH— C$_1$-C$_6$ alkyl-heteroaryl, —NHC(O)C$_1$-C$_6$ alkyl-C(O)NH—OH, heteroaryl, cycloalkyl, heterocycloalkyl, or a nitrogen-bonded cycloalkyl or heterocycloalkyl, —NHC$_1$-C$_4$ alkyl, or —N(C$_1$-C$_4$ alkyl)$_2$.

In some aspects, Z$_3$ is selected from aryl or heteroaryl, substituted by 0-4 substituents independently selected from hydrogen, deuterium, halogen, C$_1$-C$_4$ alkyl, C$_1$-C$_3$ haloalkyl, —OH, —OC$_1$-C$_6$ alkyl, or nitrogen-bonded heterocycloalkyl.

In some aspects, the compound is:

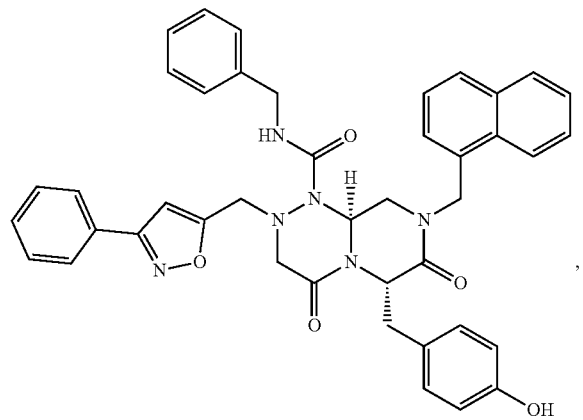

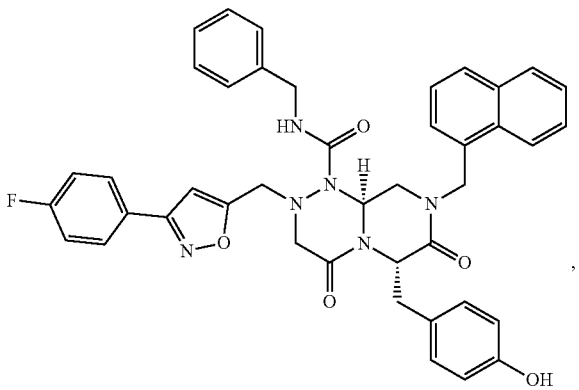

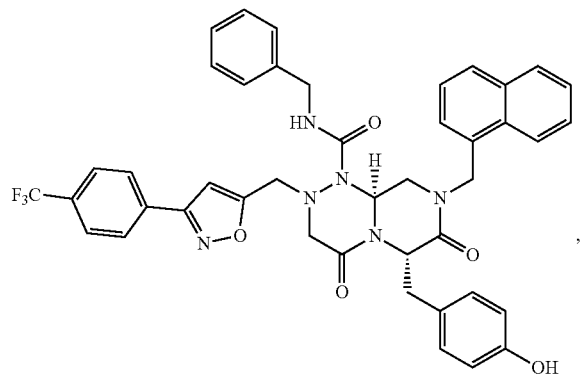

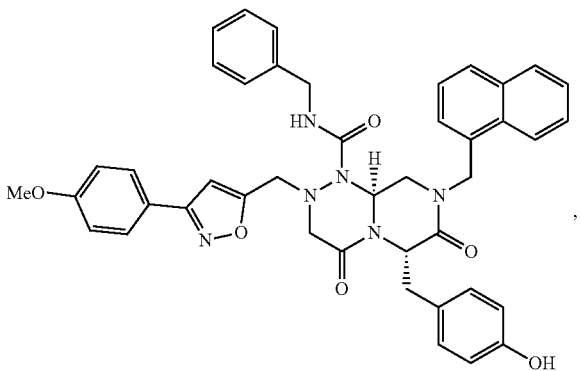

7
-continued
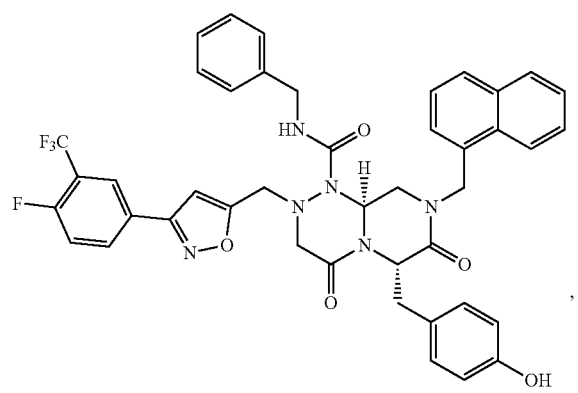
,
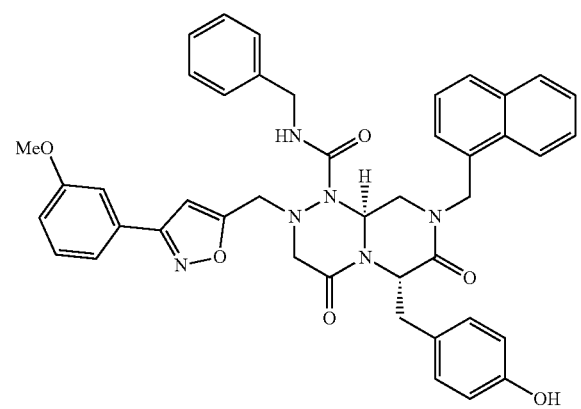
,
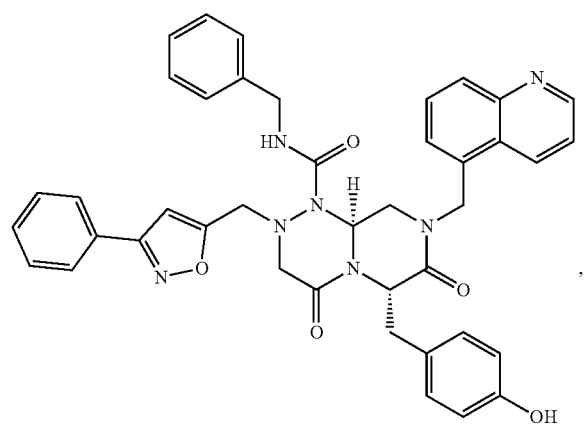
,
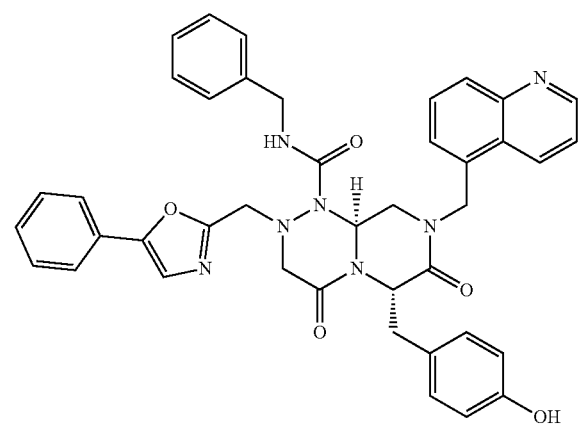
,
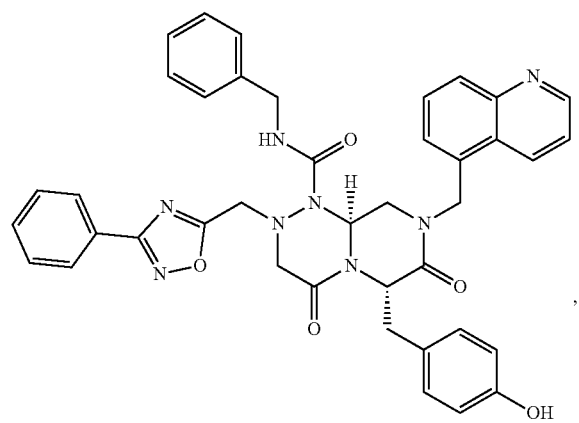
,
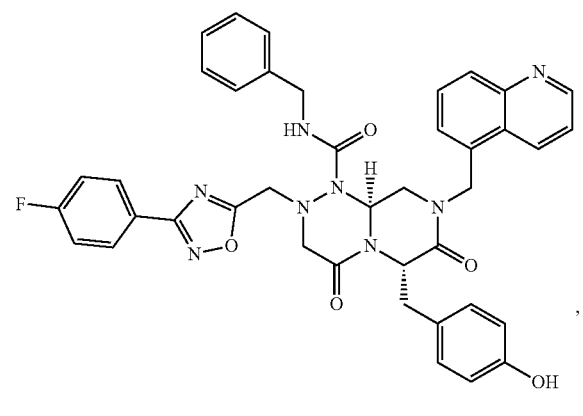
,
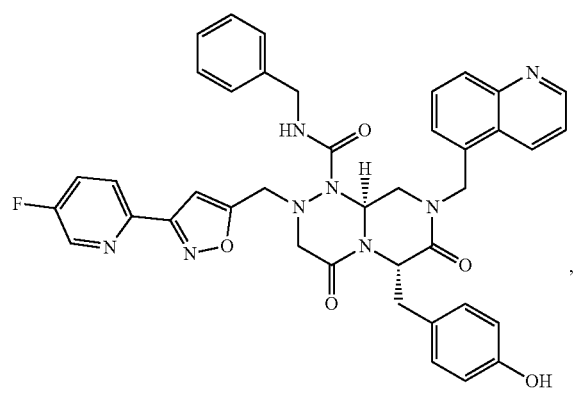
,
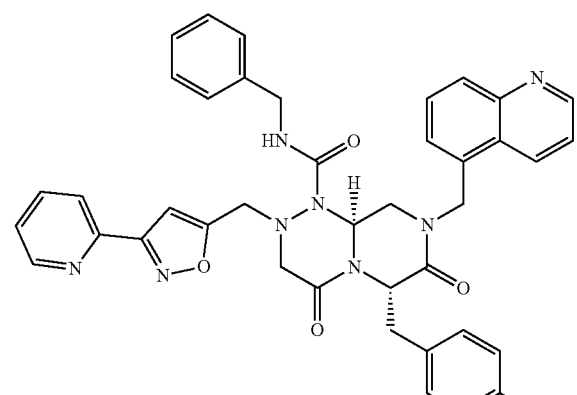
,

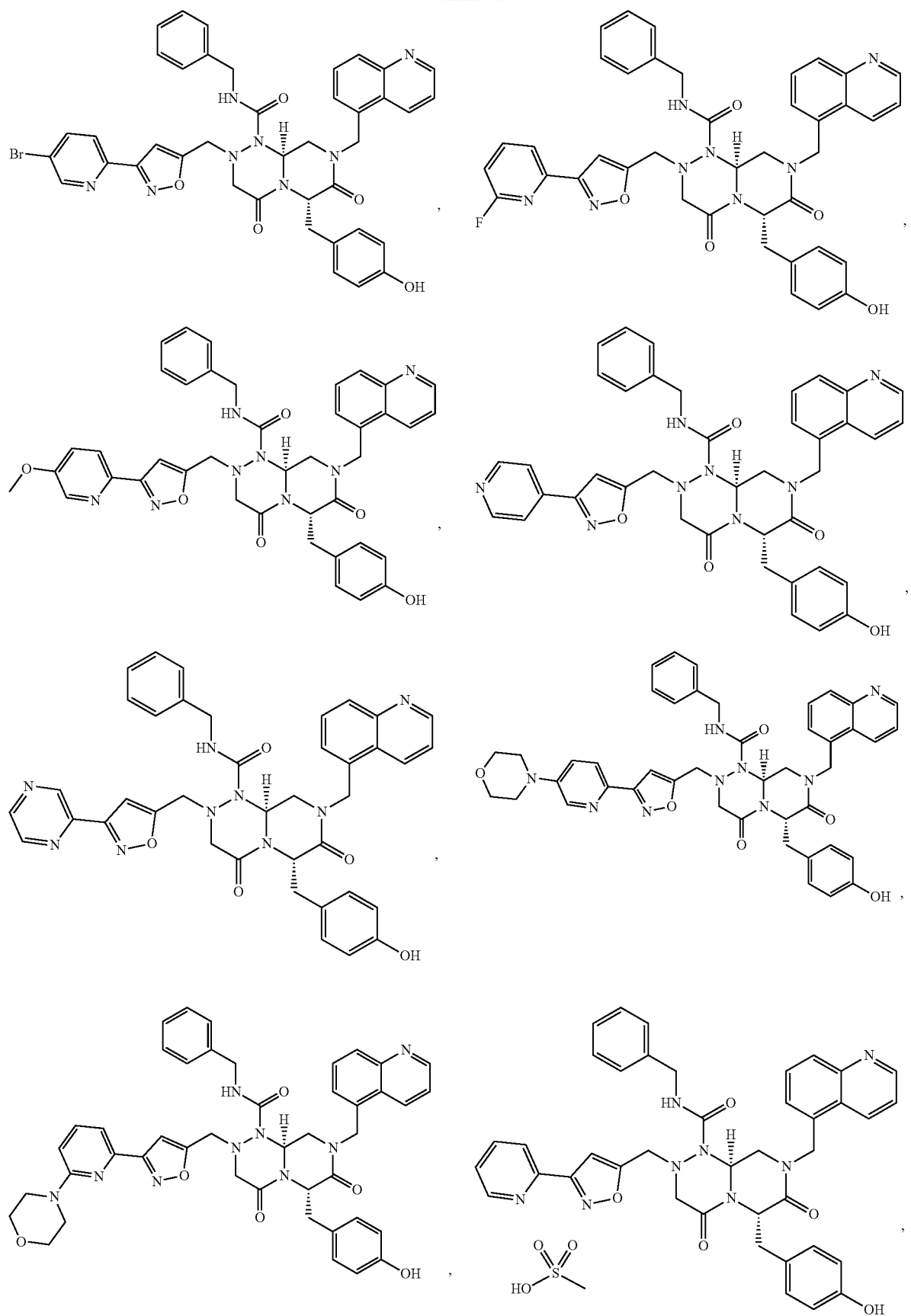

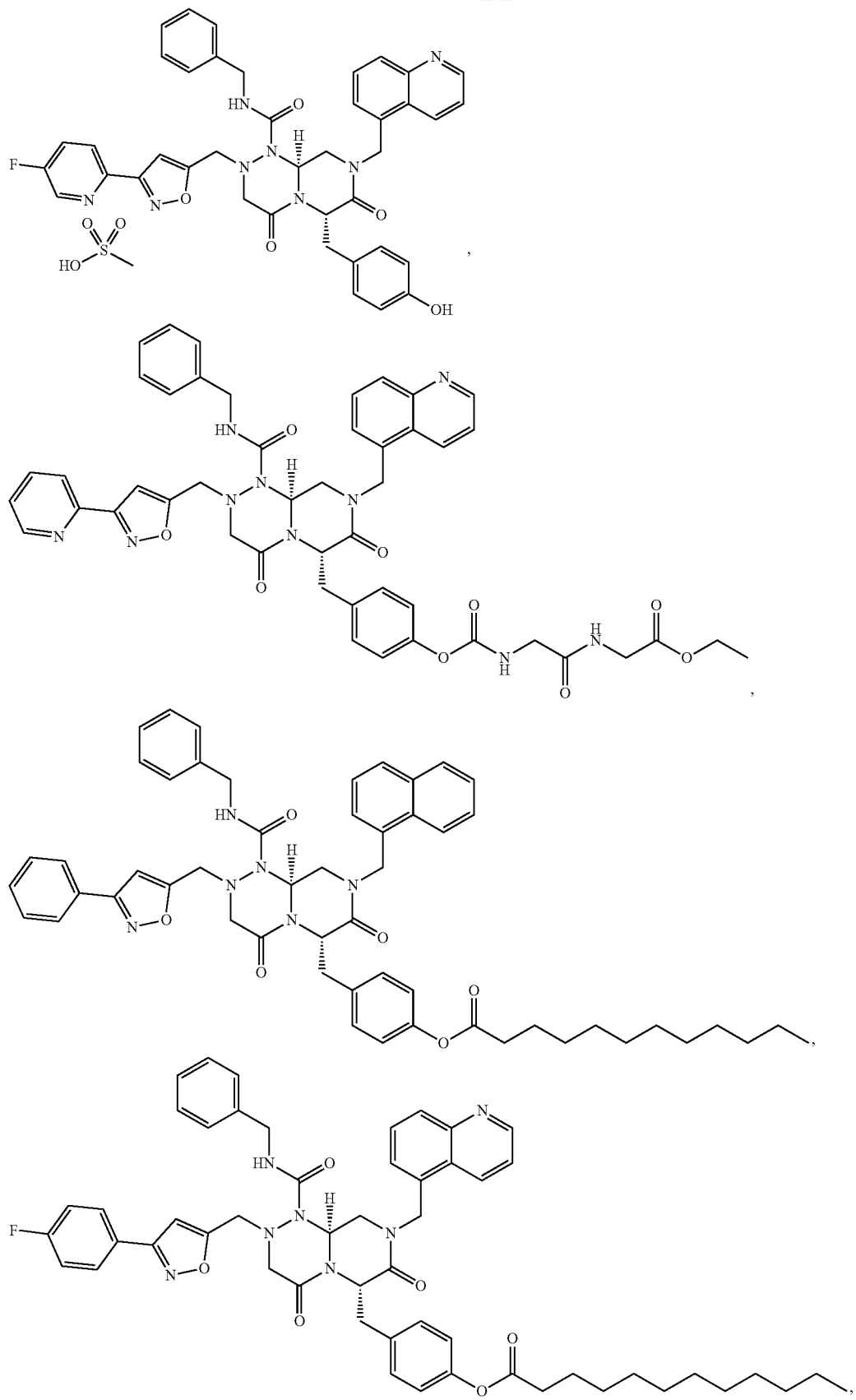

In some aspects, the invention is directed to a composition, or pharmaceutical composition comprising any one of the previously discussed compounds, and a pharmaceutically acceptable carrier.

In some aspects, the invention is directed to method of treating a disease or disorder, comprising administering to a patient or a warm-blooded mammal, having a disease or disorder mediated by aberrant CREB binding protein (CBP)/β-catenin signaling, an amount of any one of the previously discussed compounds sufficient to inhibit the CBP/catenin mediated signaling, and/or enhance p300/catenin mediated signaling.

In some aspects, an amount of the administered compound comprises a therapeutically effective amount.

In some aspects, the compound, W is X, wherein X is selected from or

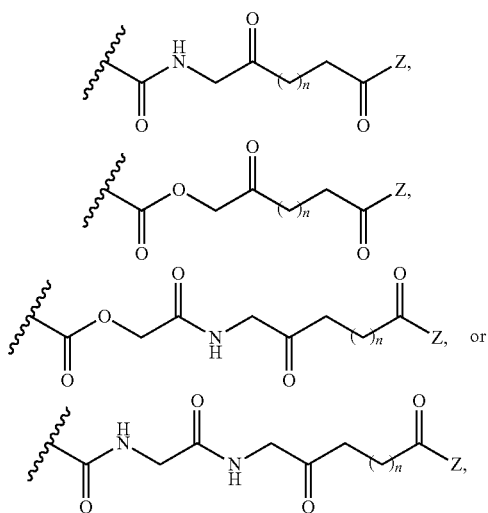

wherein Z is $OR_4$ where $R_4$ is hydrogen or $C_1$-$C_6$ alkyl, or Z is an amino acid or amino acid ester, and n is 1 or 2;

In some aspects, in the compound, X is

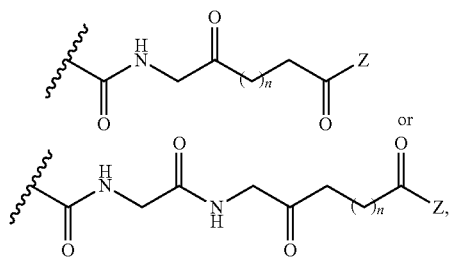

wherein Z is $OR_4$ where $R_4$ is hydrogen or $C_1$-$C_6$ alkyl, or Z is an amino acid or ester, and n is 1 or 2.

In some aspects, the disease or disorder comprises one or more of fibrosis, cancer, neurological conditions, metabolic disorders, and skin conditions.

In some aspects, the metabolic disorder comprises one or more of diabetes and/or fatty liver disease.

In some aspects, the fatty liver disease comprises one or more of alcoholic hepatic steatosis (ALD), non-alcoholic hepatic steatosis (NAFLD), and/or non-alcoholic steatohepatitis (NASH).

In some aspects, the fibrosis is fibrosis of the lung, liver, kidney, heart, endometrium, skin or systemic fibrosis.

In some aspects, the fibrosis comprises fibrosis in a SARS-CoV-2 (COVID-19) patient tissue.

In some aspects, treating cancer comprises administering the CBP/β-catenin antagonist in combination with, or as an adjunctive therapy with, one or more of cytotoxic and/or directed chemotherapy, and/or radiotherapy, and/or immunotherapy, including checkpoint inhibition (e.g., with anti-PD1, anti-PD-L1 or anti-CTLA4, etc.), chimeric antigen receptor (CAR-T) and/or CAR-NK cell based therapy.

In some aspects, the neurological condition comprises one or more of Huntington's (HD), Parkinson's (PD), Alzheimer's (AD), Multiple sclerosis (MS), and/or amyotrophic lateral sclerosis (ALS), muscular dystrophy (MD), and/or spinal muscular atrophy (SMA).

In some aspects, the skin condition comprises one or more of atopic dermatitis, psoriasis, acne, fibrosis, wounding, scarring, burns, sun or U.V. damage, diabetic ulceration, chronic ulceration, and/or alopecia.

In some aspects, W is an ester of an alkyl acid or of a fatty acid, and wherein administration comprises topical administration.

In some aspects, the invention is directed to a cosmetic method for treating a skin condition, comprising administering to a patient or a warm-blooded mammal, having a skin condition, a cosmeceutically effective amount of any one of the previously discussed compounds, wherein W is an ester of an alkyl acid or of a fatty acid, and wherein administration comprises topical administration.

In some aspects, the skin condition comprises one or more aging skin conditions selected from wrinkles, hyperpigmentation, redness, rosacea, dryness, cracking, loss of vibrance, loss of elasticity, thinning, loss of vibrance, scarring, acne, sun damage, hair loss, loss of hair coloration, reduced cuticle growth, reduced nail growth.

In some aspects, the invention is directed to a method for efficiently synthesizing a clinical grade drug, comprising use, in a penultimate or last reaction step under GMP conditions, of an intermediate 2-propynyl-compound to form a clinical grade isoxazole derivative via 3+2 cycloaddition.

In some aspects, preparing the clinical grade isoxazole derivative comprises preparing a compound according to of any one of claims 6-9 using, in a penultimate, or last reaction step, said step prior to any optional formation of a final pharmaceutically acceptable salt, phosphate or phosphate salt, an intermediate 2-propynyl-compound of formula (IIa):

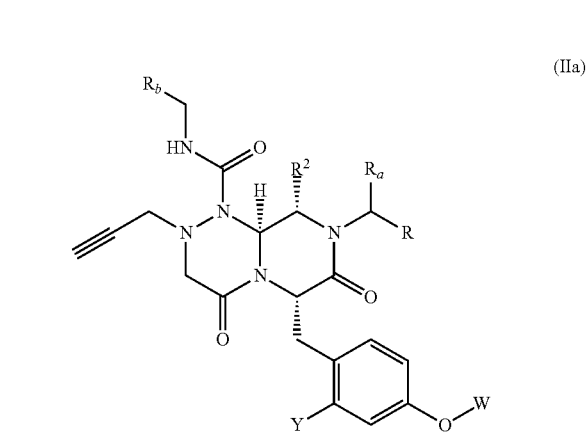

(IIa)

wherein:

$R_a$ is hydrogen or —CH$_3$;

$R_b$ is a monocyclic aryl group having 5 to 7 ring members, which may have 1 to 2 heteroatoms selected from nitrogen, oxygen or sulfur, and which may have one or more substituents selected from a group consisting of halide, cyano, or lower alkyl;

R is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group; or a bicyclic aryl group having 8 to 11 ring members, which may have 1 to 3 heteroatoms selected from nitrogen, oxygen or sulfur;

$R^2$ is hydrogen, or —CH$_3$;

Y is selected from: hydrogen, deuterium, or halogen;

W is hydrogen, an ester of an alkyl acid or of a fatty acid, or X, wherein X is selected from:

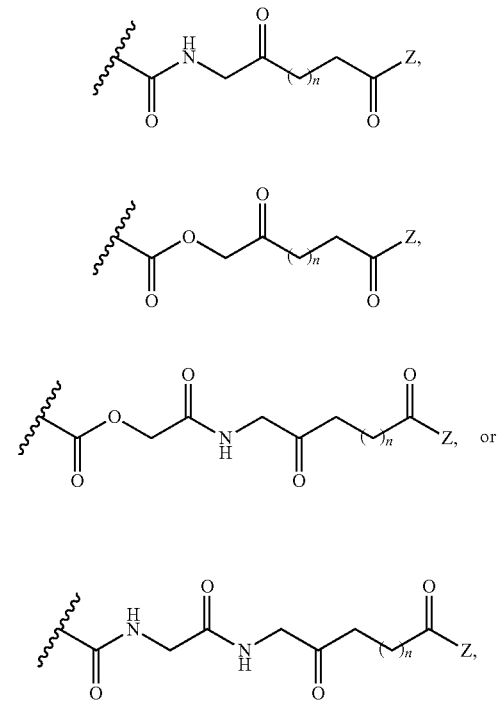

wherein Z is OR$_4$ where R$_4$ is hydrogen or C$_1$-C$_6$ alkyl, or Z is an amino acid or amino acid ester, and n is 1 or 2.

In some aspects, the last or penultimate step, performed under GMP conditions, is preceded by one or more reaction steps under non-GMP conditions, as part of an overall reaction scheme for preparing the clinical grade isoxazole derivative.

In some aspects, the invention is directed to a compound of formula (IIa):

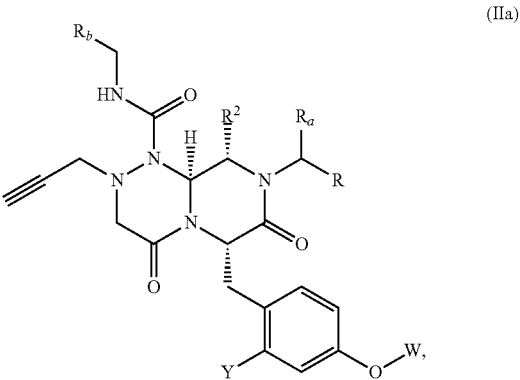

(IIa)

wherein:

$R_a$ is methyl or hydrogen;

$R_b$ is a monocyclic aryl group having 5 to 7 ring members, which may have 1 to 2 heteroatoms selected from nitrogen, oxygen or sulfur, and which may have one or more substituents selected from a group consisting of halide, cyano, or lower alkyl;

R is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group; or a bicyclic aryl group having 8 to 11 ring members, which may have 1 to 3 heteroatoms selected from nitrogen, oxygen or sulfur;

$R^2$ is hydrogen, or —CH$_3$;

Y is selected from: hydrogen, deuterium, or halogen;

W is X, wherein X is selected from:

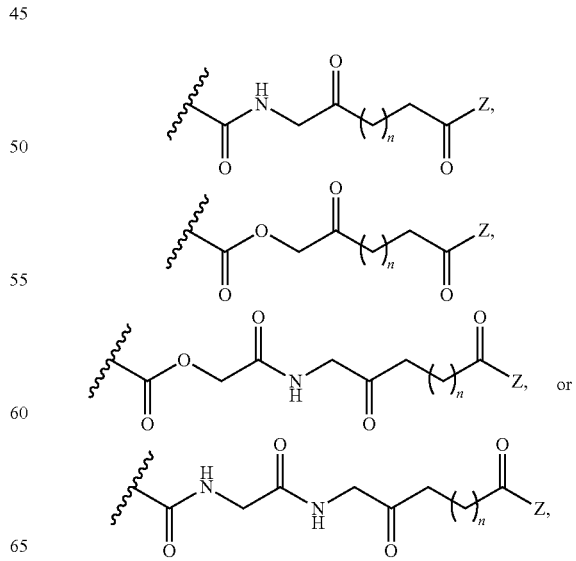

wherein Z is $OR_4$ where $R_4$ is hydrogen or $C_1$-$C_6$ alkyl, or Z is an amino acid or amino acid ester, and n is 1 or 2.

In some aspects, the method includes enhancing vaccine efficacy, comprising, administering to a subject, prior to, and/or during, and/or after vaccination, an amount of any one of the previously disclosed compounds sufficient to inhibit CBP/β-catenin mediated signaling and/or enhance p300/catenin mediated signaling.

In some aspects, the amount of the administered compound comprises a therapeutically effective amount.

In some aspects, enhancing vaccine efficacy comprises one or more of: increased levels of vaccine antigen-specific antibodies; an increase in the percent protection afforded; an increase in the number or and/or persistence of differentiated memory T-cells; and/or an increase in the duration of protection.

In some aspects, inhibiting the CBP/β-catenin mediated signaling and/or enhancing the p300/catenin mediated signaling comprises one or more of: metabolic maintenance of cell asymmetry following division in activated T cells in the subject; enhancing antigen-specific immunity by increasing the number and/or persistence of differentiated memory T-cells: and/or enhancing the presentation of antigens to T-cells by antigen presenting cells to enhance cooperativity between the innate and acquired immune systems.

In some aspects, the vaccination, comprises administration of an anti-viral vaccine.

In some aspects, the vaccination comprises administration of an anti-viral vaccine selected from influenza, SARS, SARS-CoV-2, HPV-A, HPV-B, and/or Herpes Zoster.

In some aspects, the subject is a human having an age of 55-75 yr, 55-85 yr, ≥50 yr, ≥60 yr, or ≥65 yrs).

In some aspects, administration comprises: administration as a primer before vaccination; and/or co-administration with vaccination; and/or administration or co-administration subsequent to initial vaccine.

The above summary does not include an exhaustive list of all aspects of the present invention. It is contemplated that the invention includes all compositions and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The aspects are illustrated by way of example and not by way of limitation in the figures of the accompanying drawings in which like references indicate similar elements. It should be noted that references to "an" or "one" aspect in this disclosure are not necessarily to the same aspect, and they mean at least one.

FIG. 3A compares the inventive compound [3+2]-101 (at 1 μM) with the art-recognized positive control ICG-001 (at 10 μM) in inhibiting the CBP/β-catenin specific gene (H. Ma et al Oncogene 2005, 24, 3619-31) Survivin/Birc5 gene expression (reflected as an increase in $\Delta\Delta C_t$). As is readily apparent, the CBP/β-Catenin expression inhibition activity of the inventive isoxazole is at least 10× greater than that of the control. FIG. 3B compares the inventive compound [3+2]-101 (at 1 μM) with the art-recognized positive control ICG-001 (at 10 μM) in stimulating EphB2 (p300/β-catenin-specific gene (Kumar S, et. al. Cancer Res. 2009, 69, 3736-45) gene expression (reflected as a decrease in $\Delta\Delta C_t$). As is readily apparent, the EphB2 gene expression stimulating activity of the inventive isoxazole is at least 10× greater than that of the control. This reflects a decrease in CBP/β-catenin based transcription with an increase in p300/β-catenin based transcription, mediated by the specific CBP/β-catenin inhibitory activities of [3+2]-101 and ICG-001.

FIG. 5 shows, according to further non-limiting aspects of the present invention, that there was a significant (Bonferrorii Multiple Comparison Test; mean+/−SD) increase in body weight gain in mice treated with [3+2]-120A and with

[3+2]-120B in a bleomycin-induced pulmonary fibrosis model study in mice (treatment period: day 7-20).

Figure 5:
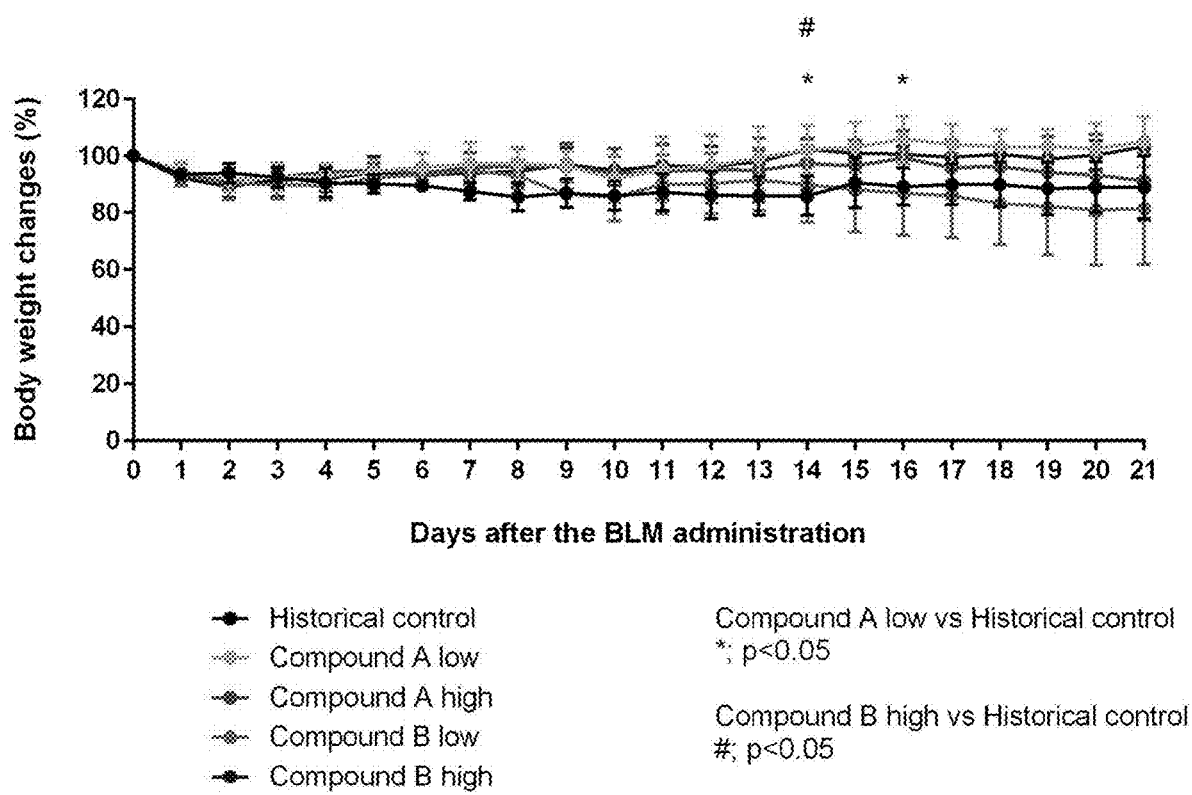
Figure 6:
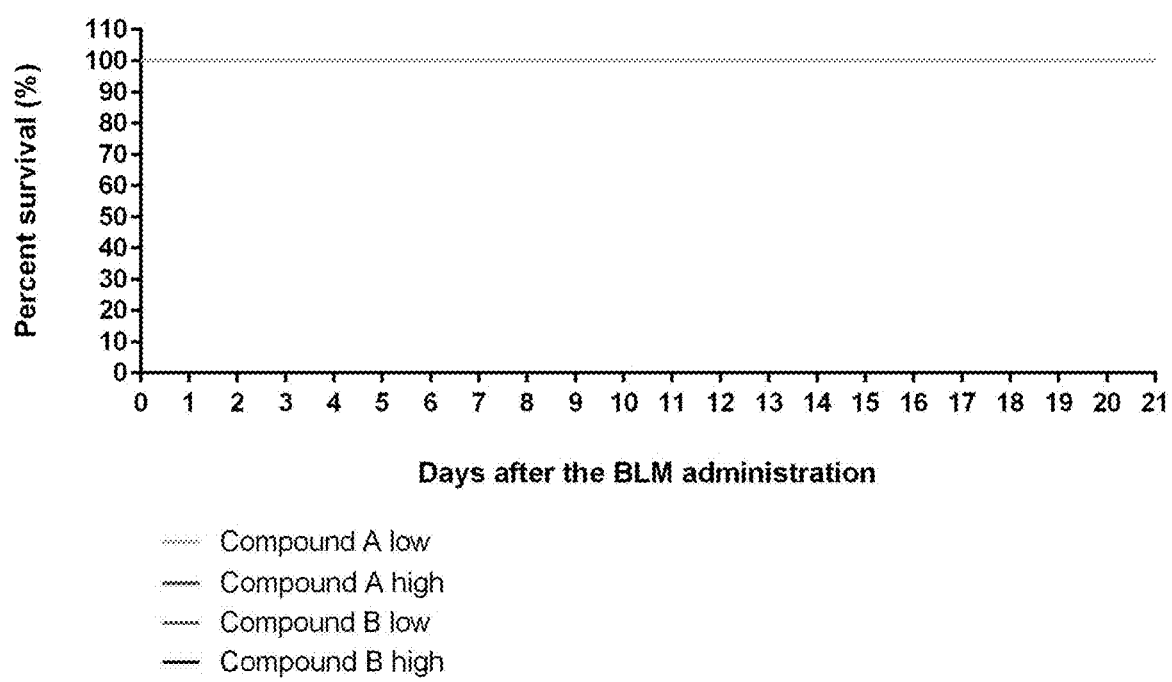
Figure 7A:
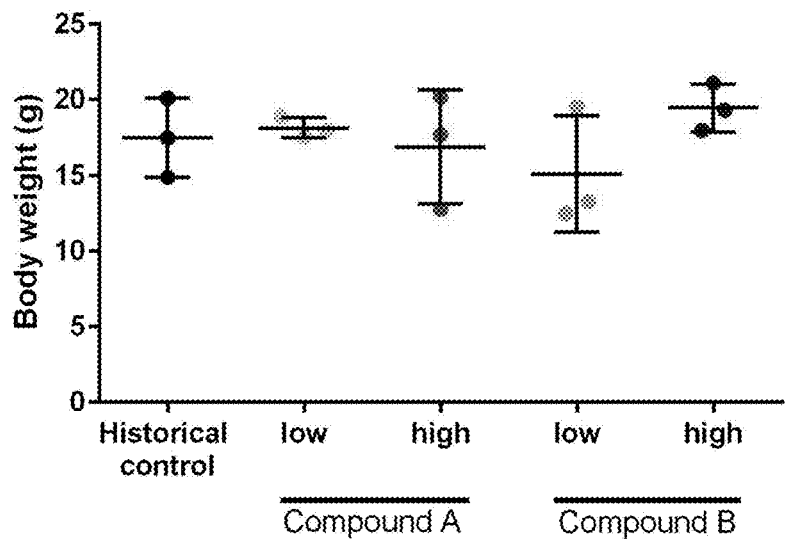
Figure 7B:
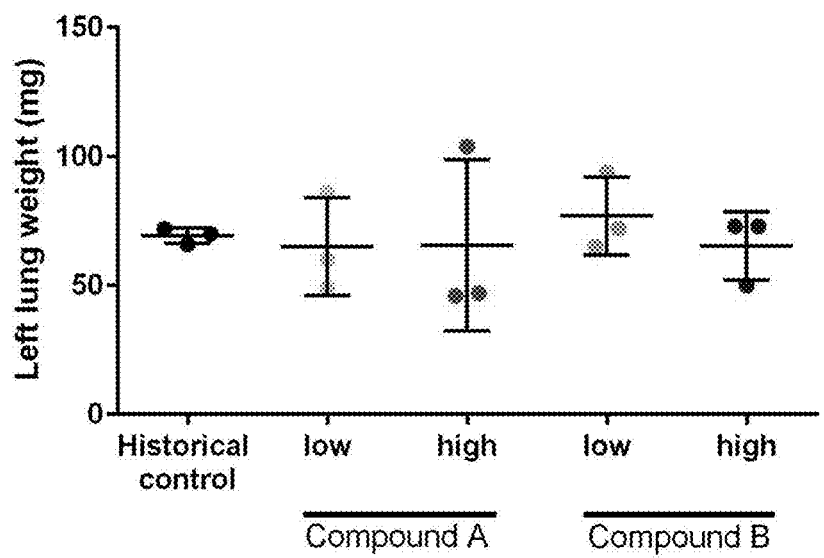
Figure 7C:
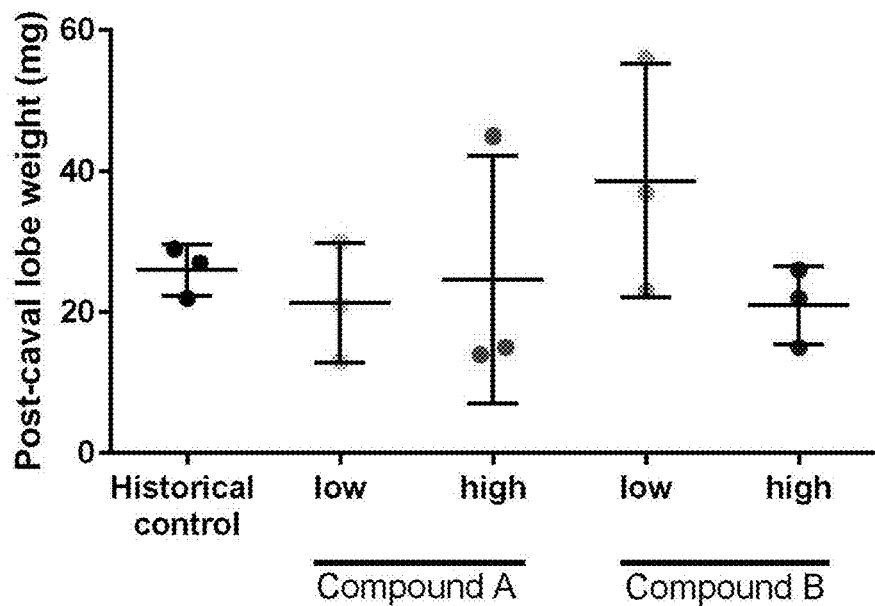
Figure 7D:
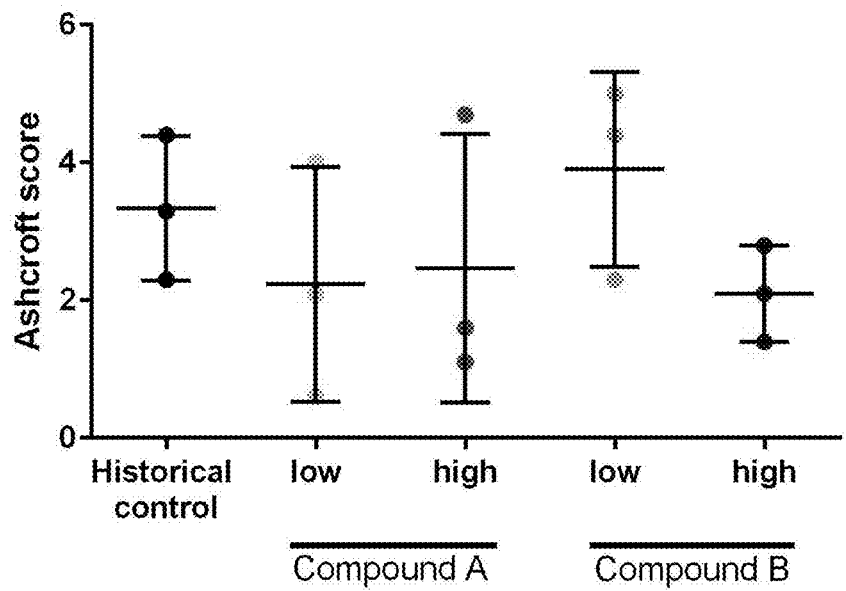
Figure 8A:
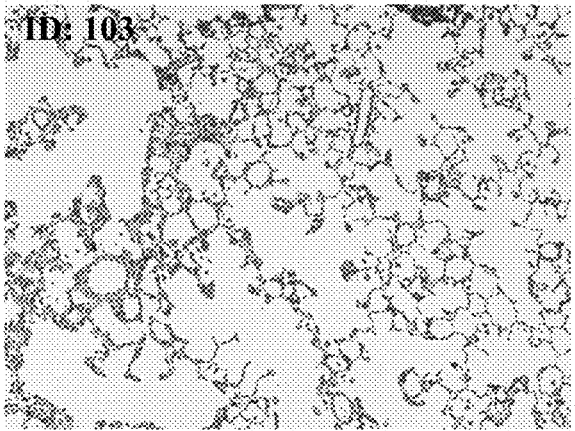
Figure 8B:
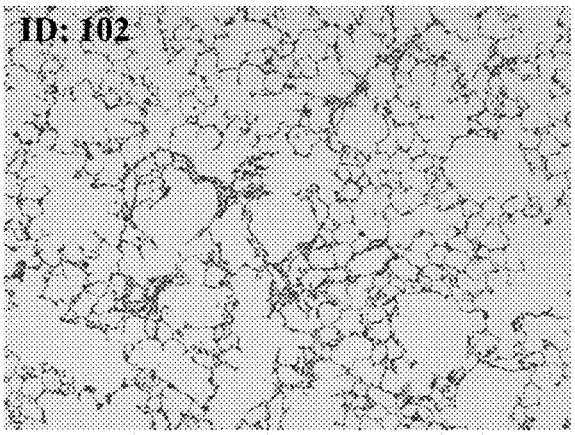
Figure 8C:
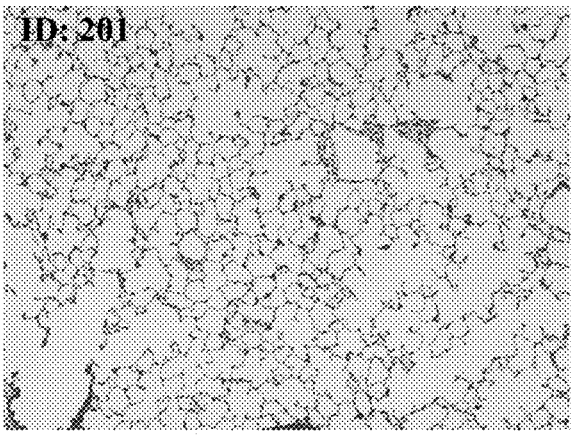
Figure 8D:
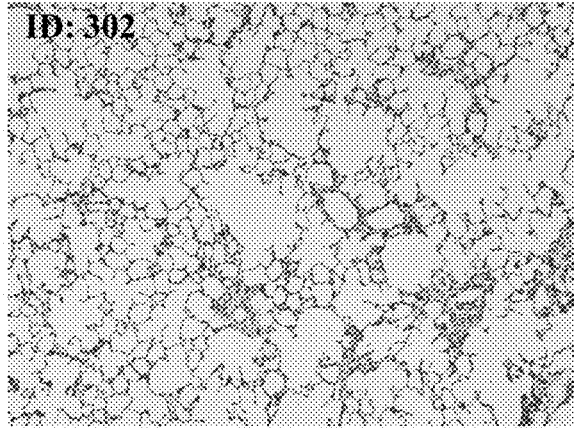
Figure 8E:
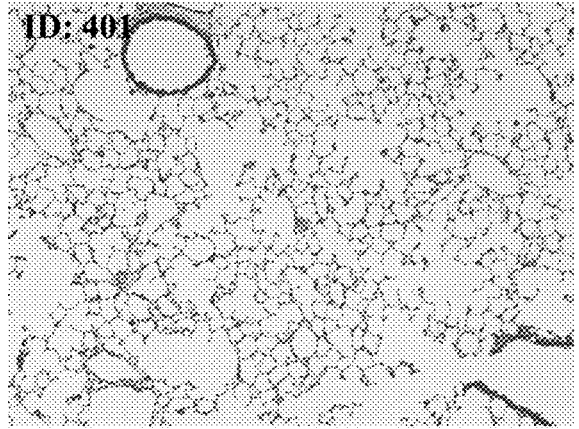

FIG. 6 shows, according to further non-limiting aspects of the present invention, that in the study of FIG. 5 all mice survived (hence the survival curves for the different treatment groups curves are superimposed; Log Rank Test), whereas historically approximately 30% of the mice die before day 21 even when treated in this bleomycin-induced pulmonary fibrosis model.

FIGS. 7A-7D show, according to further non-limiting aspects of the present invention, that in this study in FIGS. 5 and 6 there was a significant (Bonferroni Multiple Comparison Test; mean+/−SD) decrease in lung weights and in Ashcroft scores in [3+2]-120A treated and [3+2]-120B treated mice, based on histological analysis. FIGS. 7A-7D are as follows: body weight on day of sacrifice (7A); left lung weight (7B); post-caval lobe weight (7C); and Ashcroft score (7D).

FIGS. 8A-8E show, according to further non-limiting aspects of the present invention, representative histological data (photomicrographs of Masson's Trichrome-stained lung sections; original magnifications ×100) for the study of FIGS. 5-7, showing that the [3+2] series compounds are efficacious in the bleomycin-induced pulmonary fibrosis model in reducing extracellular collagen deposition. FIGS. 8A-8E are as follows: historical bleomycin only control, (8A, "ID:103"); [3+2]-120A low dose (8B, "ID:102"); [3+2]-120A high dose (8C, "ID:201"); [3+2]-120B low dose (8D, ID:302"); and [3+2]-120B high dose (8E, ID:401").

Figure 9:
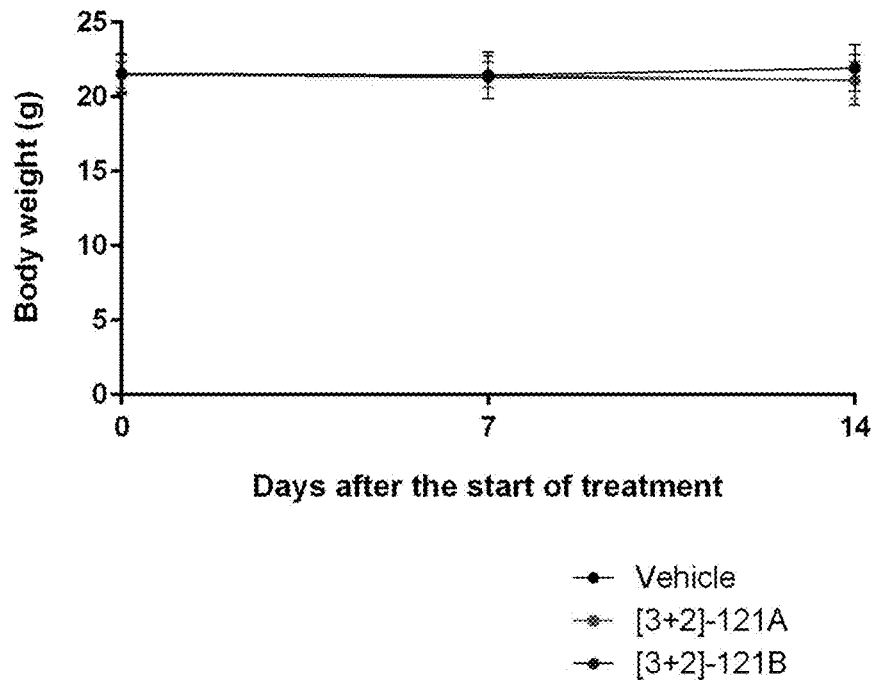

FIG. 9 shows, according to further non-limiting aspects of the present invention, that in an NG/Nga mouse model of atopic dermatitis, there were no significant differences in mean body weight at any day during the treatment period between the Vehicle group and the treatment (representative inventive compound [3+2]-121A (low dose) and [3+2]-121B) (high dose of compound [3+2]-121A)) groups, attesting to the safety of the treatment.

Figure 10:
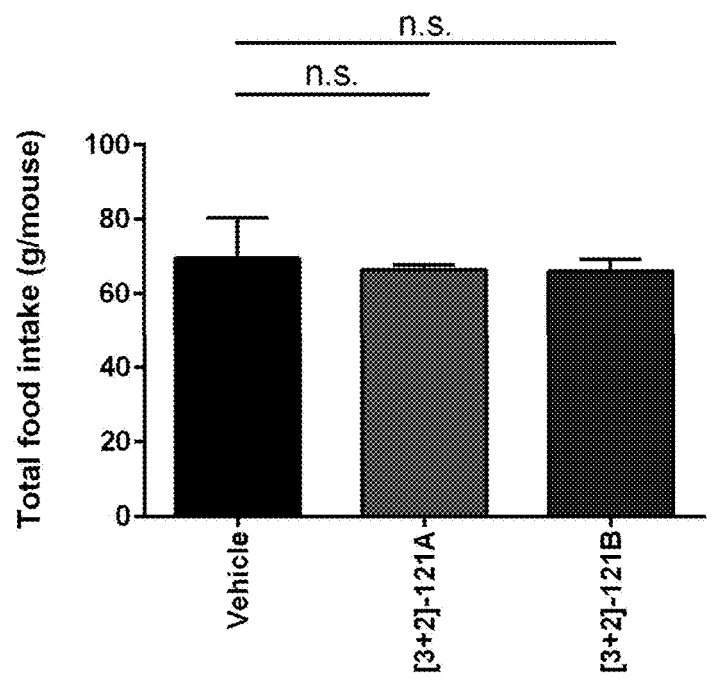

FIG. 10 shows, according to further non-limiting aspects of the present invention, that in the study of FIG. 9, there were no significant differences in the food consumption ("food intake") per mouse between the Vehicle control group and the treatment groups.

Figure 11A:
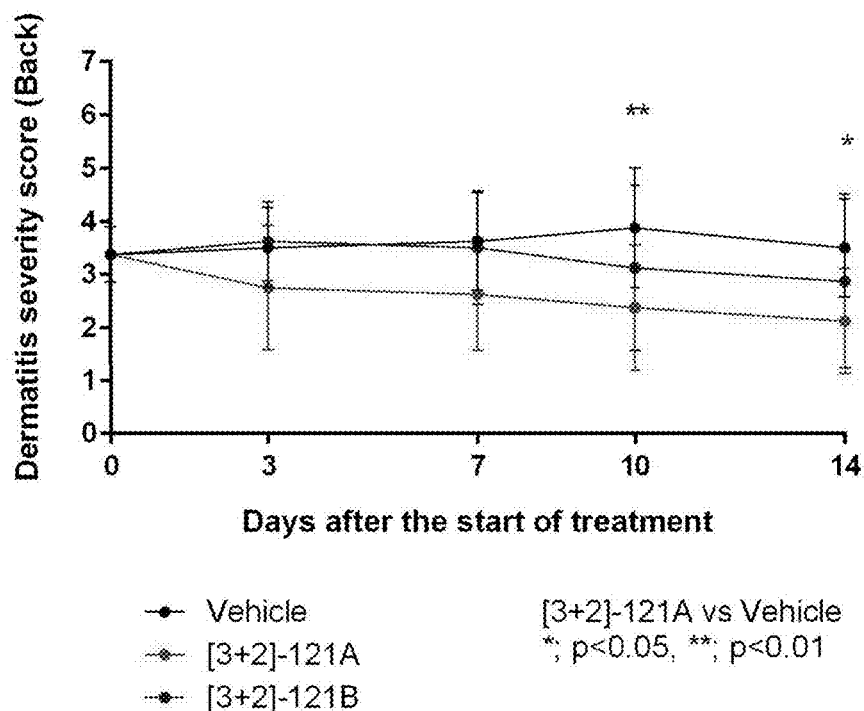
Figure 11B:
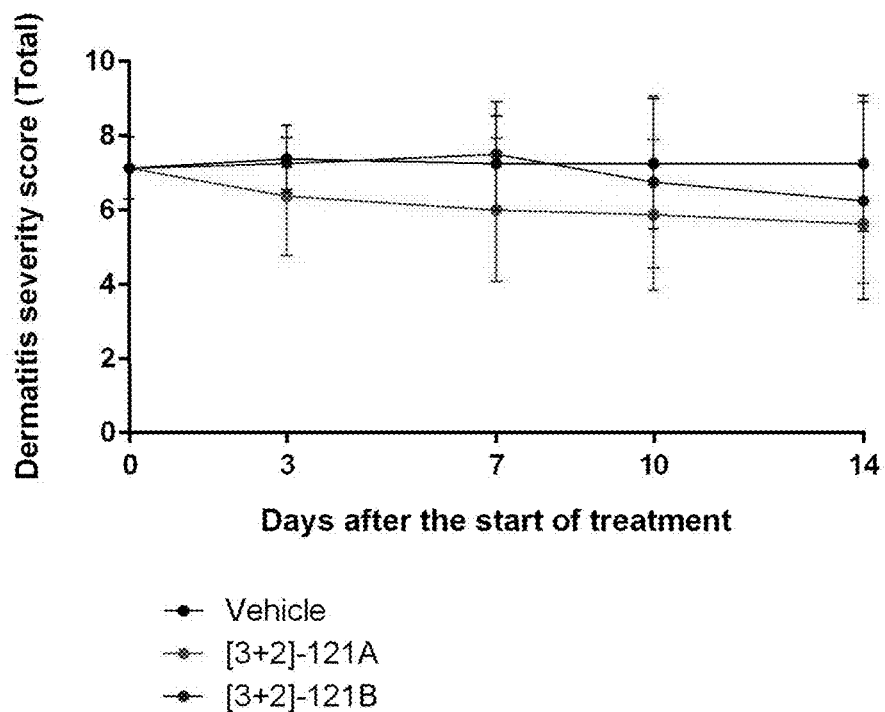

FIGS. 11A and 11B show, according to further non-limiting aspects of the present invention, that in the study of FIGS. 9 and 10, the [3+2]-121A group (low dose) showed a significant decrease in the total dermatitis severity score, primarily on the back on Days 10 and 14 compared with the Vehicle control group. FIGS. 11A and 11B are as follows: Back area (11A); and Total (Back area plus Auricle area) (11B).

Figure 12:
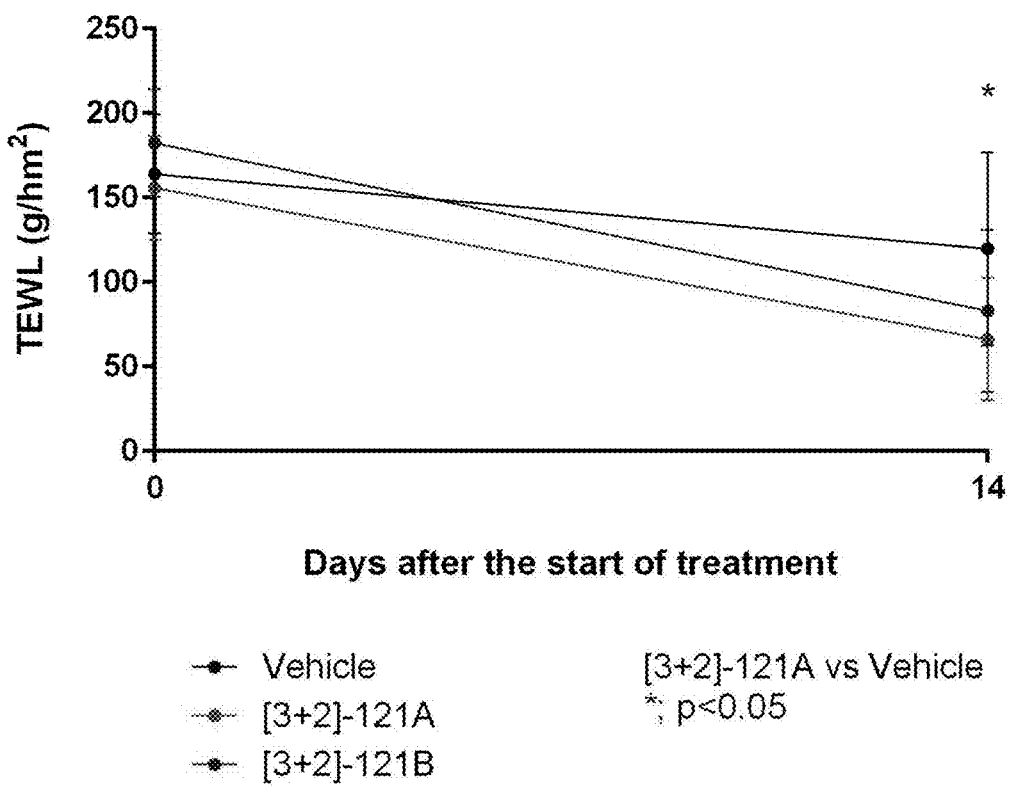

FIG. 12 shows, according to further non-limiting aspects of the present invention, that in the study of FIGS. 9-11, the [3+2]-121A and [3+2]-121B groups showed a significant decrease in the TEWL at day 14 attesting to the improvement in barrier function.

Figures 13A, 13B, 13C:
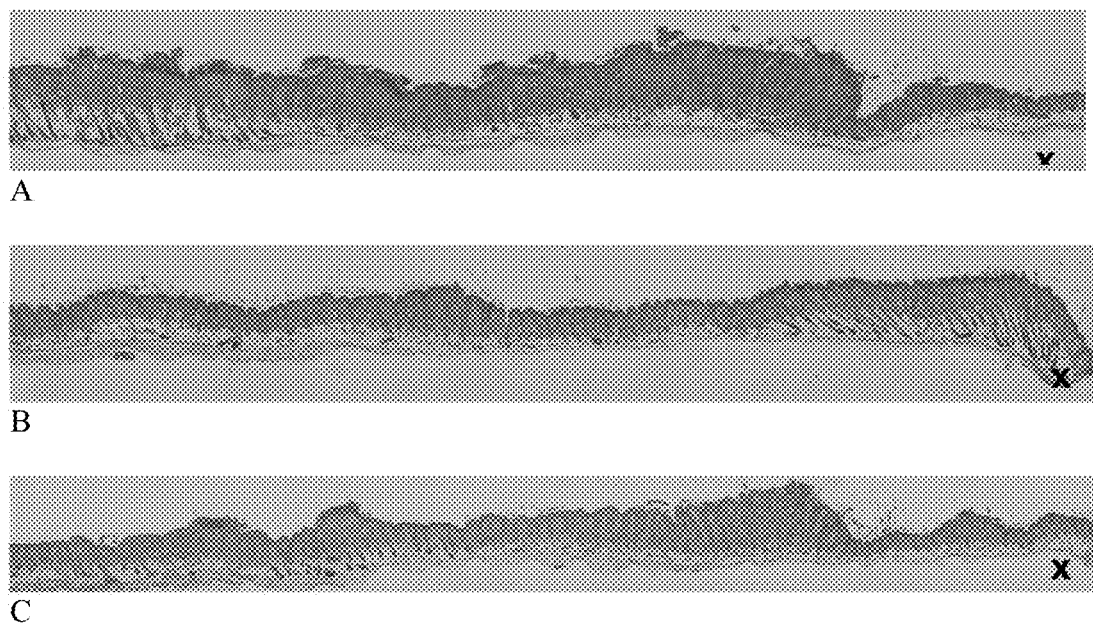

FIGS. 13A-13C show, according to further non-limiting aspects of the present invention, that representative histological sections taken in the study of FIGS. 9-12, confirm a significant reduction in inflammation and inflammatory cell influx in both the [3+2]-121A and [3+2]-121B groups, as shown in the representative photomicrographs. FIGS. 13A-13C are as follows: Vehicle control (13A); [3+2]-121A (13B); and [3+2]-121B (13C).

DETAILED DESCRIPTION

In this section we shall explain several preferred aspects of this invention with reference to the appended drawings. Whenever aspects are not clearly defined, the scope of the invention is not limited only to that shown in the drawings, which are meant merely for the purpose of illustration. Also, while numerous details are set forth, it is understood that some aspects of the invention may be practiced without these details. In other instances, well-known compositions, components and/or techniques have not been shown in detail so as not to obscure the understanding of this description.

As used herein, the singular forms "a", "an", and "the" are intended to include the plural forms as well, unless the context indicates otherwise. It will be further understood that the terms "comprises" and/or "comprising" specify the presence of stated features, steps, operations, elements, compositions and/or components, but do not preclude the presence or addition of one or more other features, steps, operations, elements, components, compositions and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in someway inherently mutually exclusive.

Provided are compounds of formula (Ia):

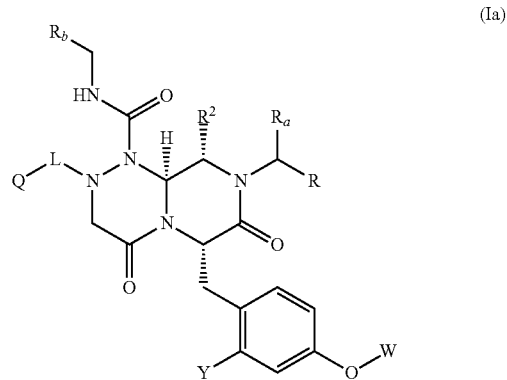

(Ia)

and stereoisomers, geometric isomers, tautomers, solvates (e.g., hydrates) metabolites, prodrugs, isotopically-labeled derivatives, and any salts including pharmaceutically acceptable salts thereof, wherein:

$R_a$ is hydrogen or —$CH_3$;

$R_b$ is a monocyclic aryl group having 5 to 7 ring members, which may have 1 to 2 heteroatoms selected from nitrogen, oxygen or sulfur, and which may have one or more substituents selected from a group consisting of halide, cyano, or lower alkyl;

R is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group; or a bicyclic aryl group, or substituted bicyclic aryl, having 8 to 11 ring members, which may have 1 to 3 heteroatoms selected from nitrogen, oxygen or sulfur, where the substituted bicyclic aryl may have one or more substituents independently selected from amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group;

$R^2$ is hydrogen, or —$CH_3$;

Y is selected from: hydrogen, deuterium, or halogen;

W is hydrogen, phosphate or phosphate salt, an ester of an alkyl acid or of a fatty acid, or X, wherein X is selected from:

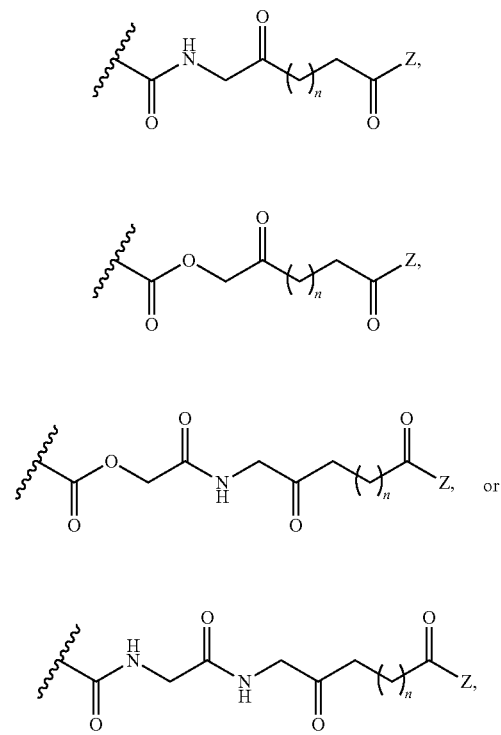

wherein Z is $OR_4$ where $R_4$ is hydrogen or $C_1$-$C_6$ alkyl, or Z is an amino acid or amino acid ester, and n is 1 or 2;

L is —$CH_2$—, —$CF_2$—, or —$C(CH_3)_2$—; and

Q is a 5- or 6-membered nitrogen-containing heteroaryl substituted by 0-2 substituents, selected from:

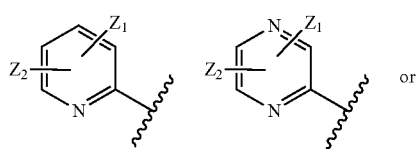

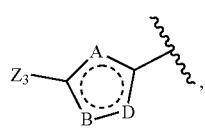

wherein A, B, and D are independently selected from O, S, N, or —CH, wherein $Z_1$, $Z_2$ are independently selected from hydrogen, deuterium, halogen, $C_1$-$C_4$ alkyl, —OH, —$OC_1$-$C_6$ alkyl, and

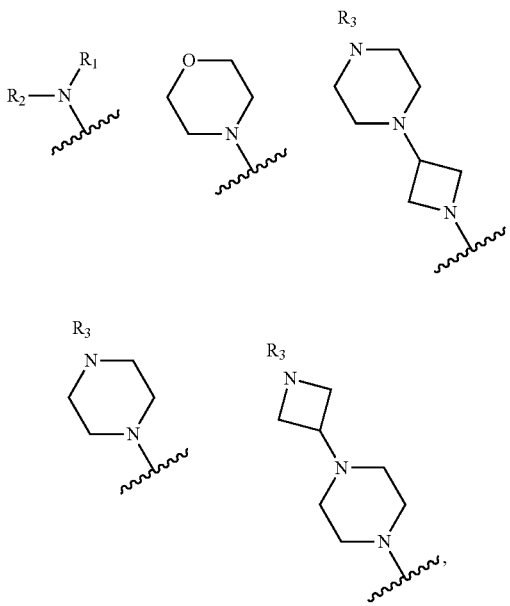

wherein $R_1$, $R_2$ and $R_3$ are independently selected from hydrogen, $C_1$-$C_6$ alkyl, or $C_1$-$C_6$ alkyl containing one or more —OH, and wherein $Z_3$ is selected from hydrogen, halogen, or a direct-bonded, or —NH-linked, —$OC_1$-$C_3$ alkyl linked, or —$NHC_1$-$C_3$ alkyl linked aryl, heteroaryl, cycloalkyl, heterocycloalkyl, or a nitrogen-bonded cycloalkyl, heterocycloalkyl, or —$NHC_1$-$C_4$ alkyl, —$N(C_1$-$C_4$ alkyl$)_2$, each of which is substituted by 0-4 substituents independently selected from hydrogen, deuterium, halogen, $C_1$-$C_4$ alkyl, $C_1$-$C_3$ haloalkyl, —OH, —$OC_1$-$C_6$ alkyl, —$OC_1$-$C_6$ alkyl-C(O)NH—OH, —$NH_2$, —C(O)NH—$C_1$-$C_6$ alkyl-heteroaryl, —NHC(O)$C_1$-$C_6$ alkyl-C(O)NH—OH, heteroaryl or cycloalkyl, heterocycloalkyl, or a nitrogen-bonded cycloalkyl or heterocycloalkyl, —$NHC_1$-$C_4$ alkyl, or —$N(C_1$-$C_4$ alkyl$)_2$.

In the compounds, the ester of the alkyl acid or of the fatty acid may be preferably selected from:

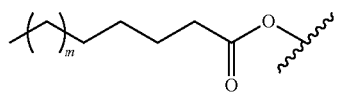

wherein m is 1 to 14,

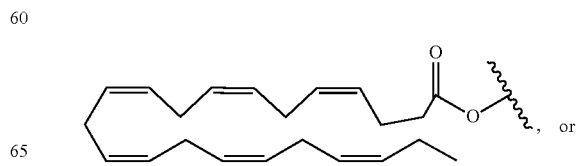

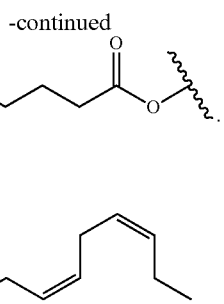

In the compounds, R may be a bicyclic aryl selected from naphthyl, quinolinyl, isoquinolinyl, quinoxaline, phthalazine, quinazoline, cinnoline, naphthyridine, or substituted variants thereof.

In the compounds, the compound may preferably be of the formula (Ib):

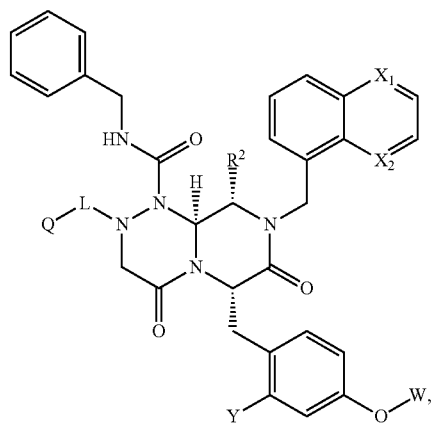

wherein $X_1$ and $X_2$ are independently selected from: N, or —CH.

In preferred aspects of the compounds:
L is —CH$_2$—;
Q is

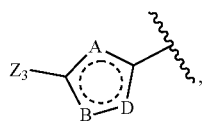

wherein A, B, and D are independently selected from O, S, N, or —CH (preferably wherein A is —CH, B is N, and D is O (Q is $Z_3$-isoxazole-), and wherein W is hydrogen, phosphate or phosphate salt, an ester of an alkyl acid or of a fatty acid, or X, wherein X is selected from:

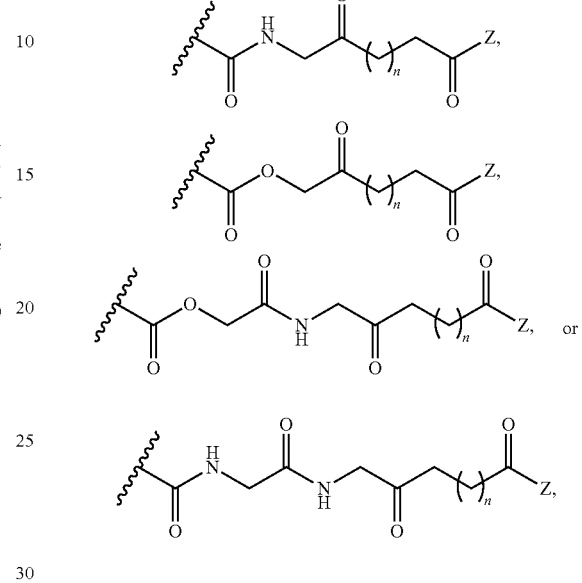

wherein Z is OR$_4$ where R$_4$ is hydrogen or $C_1$-$C_6$ alkyl, or Z is an amino acid or amino acid ester, and n is 1 or 2).

In the compounds, $Z_3$ may be selected from aryl or heteroaryl, each of which is substituted by 0-4 substituents independently selected from hydrogen, deuterium, halogen, $C_1$-$C_4$ alkyl, $C_1$-$C_3$ haloalkyl, —OH, —O$C_1$-$C_6$ alkyl, —O$C_1$-$C_6$ alkyl-C(O)NH—OH, —NH$_2$, —C(O)NH—$C_1$-$C_6$ alkyl-heteroaryl, —NHC(O)$C_1$-$C_6$ alkyl-C(O)NH—OH, or heteroaryl, cycloalkyl, heterocycloalkyl, or a nitrogen-bonded cycloalkyl or heterocycloalkyl, —NH$C_1$-$C_4$ alkyl, or —N($C_1$-$C_4$ alkyl)$_2$ (preferably, $Z_3$ is selected from aryl or heteroaryl), substituted by 0-4 substituents independently selected from hydrogen, deuterium, halogen, $C_1$-$C_4$ alkyl, $C_1$-$C_3$ haloalkyl, —OH, —O$C_1$-$C_6$ alkyl), or nitrogen-bonded heterocycloalkyl.

Particular preferred compounds are:

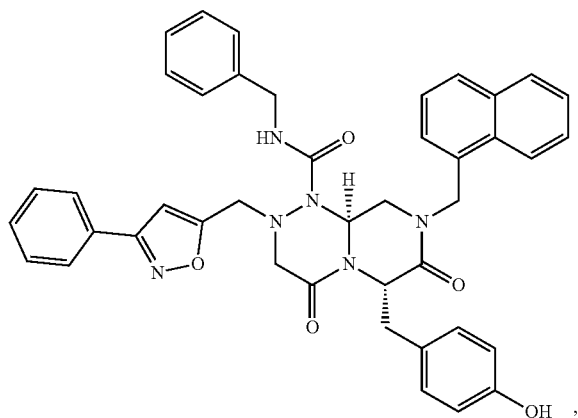

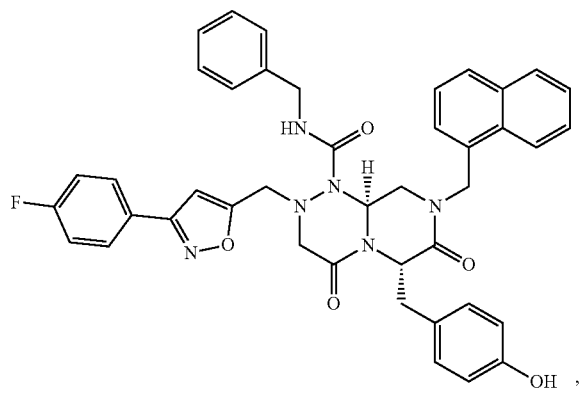

25
26
-continued
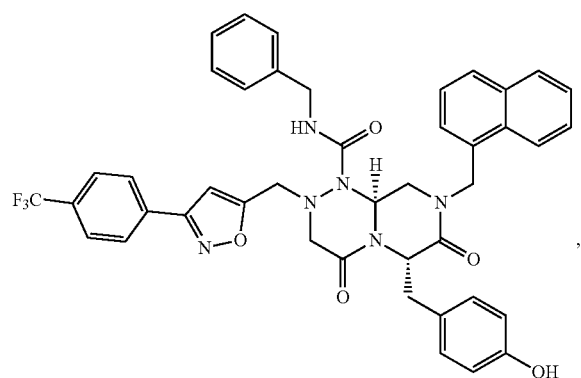
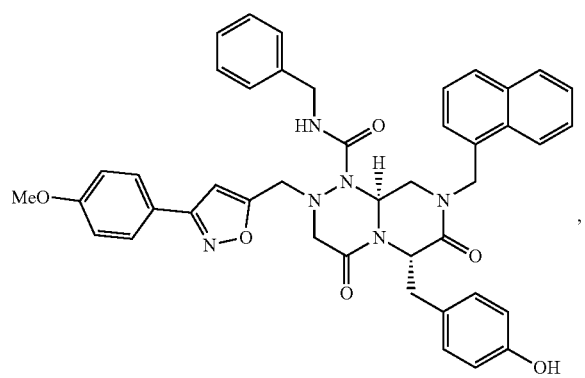
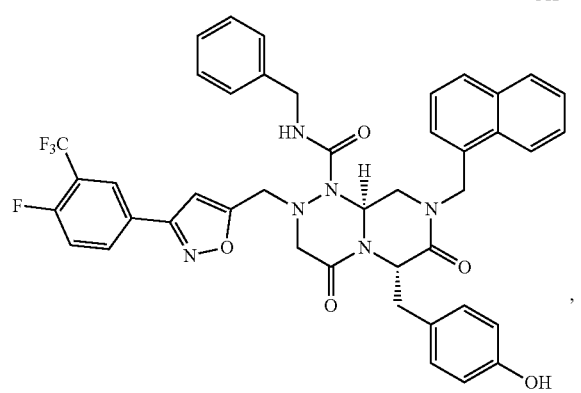
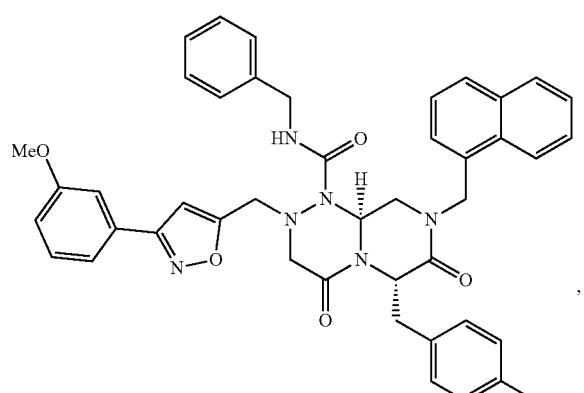
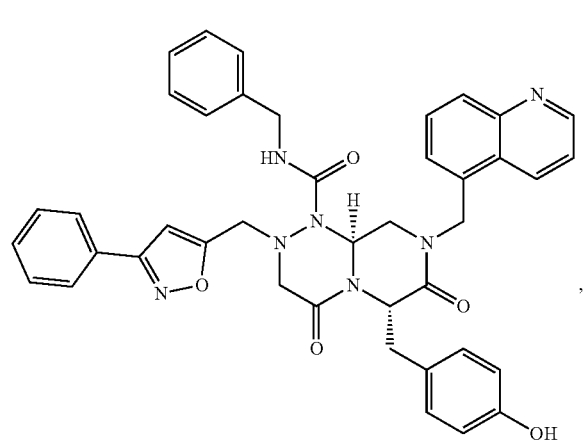
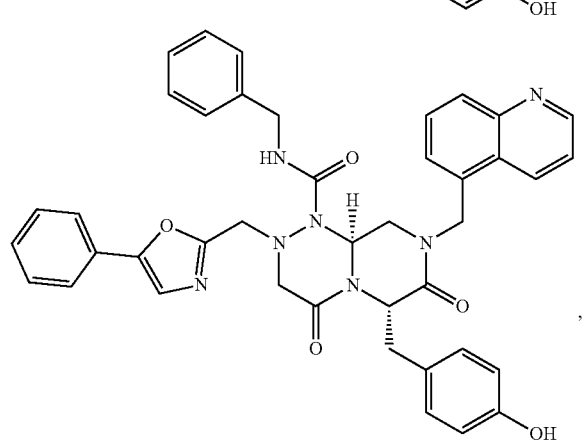
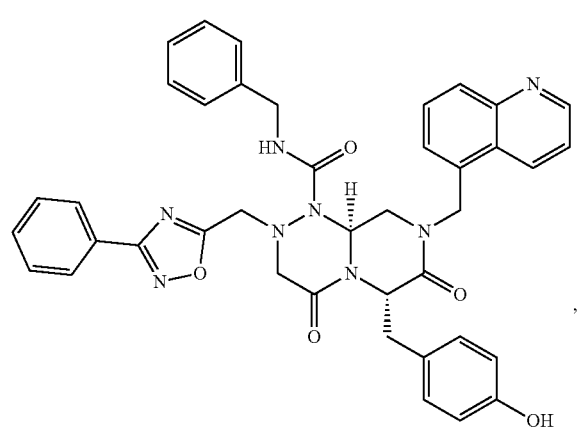
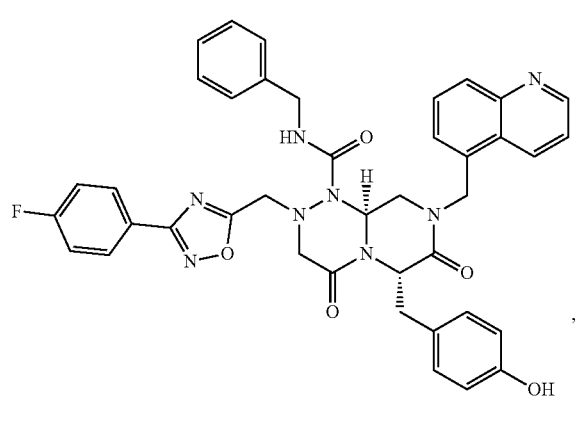

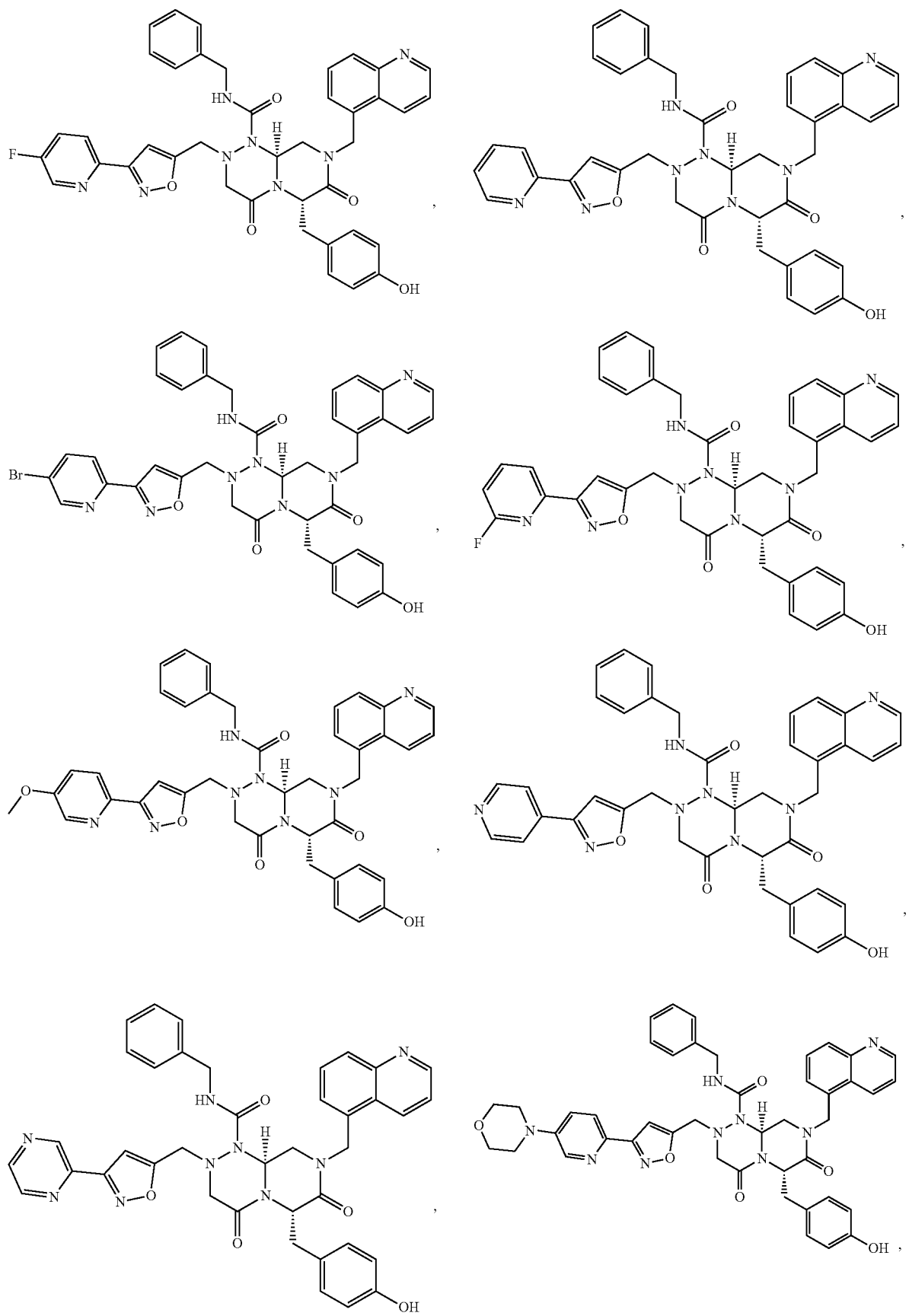

-continued
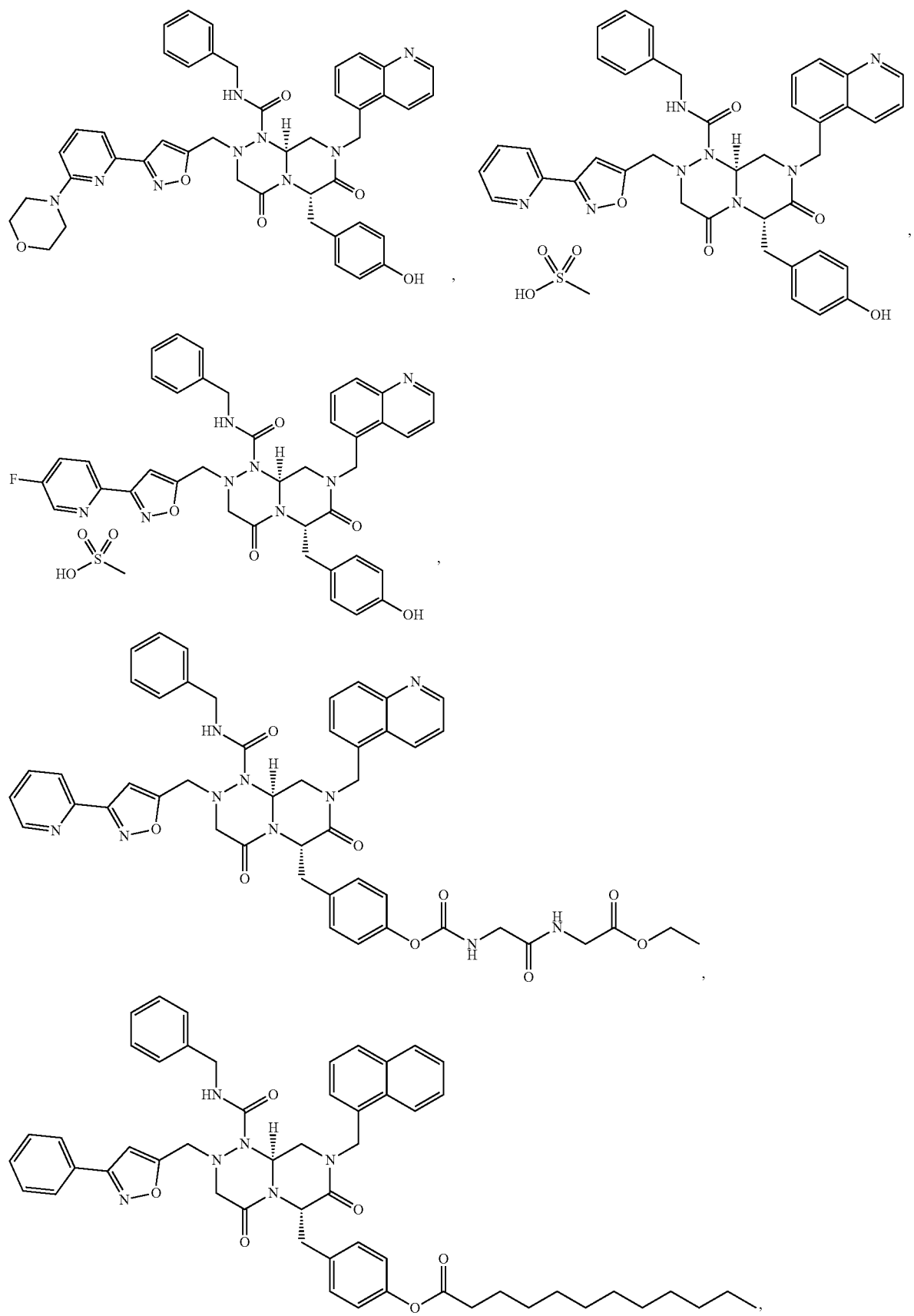

-continued

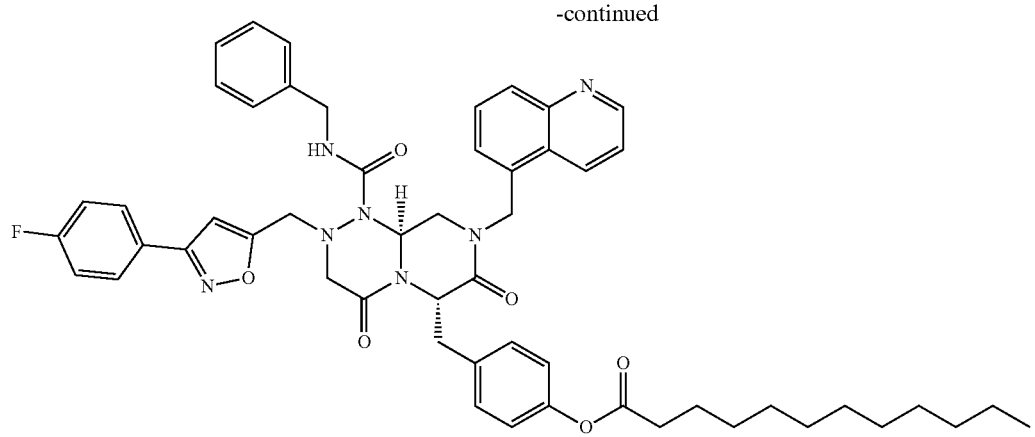

and composition or pharmaceutical composition comprising the compounds disclosed herein, and a pharmaceutically acceptable excipient or carrier.

Another aspect of the present invention provides compounds of formula (Ia), (Ib) and (IIa) that are potent modulators of the Wnt/β-catenin pathway. Provided are potent compounds that inhibit CREB binding protein (CBP)/β-catenin mediated signaling, compositions and pharmaceutical compositions comprising these compounds, and the use of these compounds for the treatment of any aberrant CBP/β-catenin mediated signaling disease or disorder, including but not limited to fibrosis, cancer, neurological disorders, metabolic disorders (including diabetes and fatty liver disease, e.g., alcoholic (ALD) and non-alcoholic hepatic steatosis (ALD and NAFLD, respectively), and including non-alcoholic steatohepatitis (NASH)), skin conditions (e.g., dermatitis, psoriasis, alopecia, skin aging, etc.) aging, and optionally further including one or more of pulmonary hypertension, congestive heart failure, chronic kidney disease, renal fibrosis, cardiac fibrosis, polycystic ovary syndrome (PCOS), endometriosis, and/or systemic fibrosis/scleroderma. Both therapeutic, and cosmetic methods are provided.

Compounds of formula (Ia), (Ib) and (IIa) of the present invention may contain chiral centers and therefore may exist in different enantiomeric and diastereomeric forms. This invention relates to all optical isomers and all stereoisomers of compounds having the structures as defined above, both as racemic mixtures and as individual enantiomers and diastereoisomers of such compounds, and mixtures thereof, and to all pharmaceutical compositions and methods of treatment defined below that contain or employ them, respectively. In some embodiments, the compounds are the (S)-enantiomer. In other embodiments, the compounds are the (R)-enantiomer.

As the compounds of the present invention may possess at least two asymmetric centers, they are capable of occurring in various stereoisomeric forms or configurations. Hence, the compounds can exist in separated (+)- and (−)-optically active forms, as well as mixtures thereof. The present invention includes all such forms within its scope. Individual isomers can be obtained by known methods, such as optical resolution, optically selective reaction, or chromatographic separation in the preparation of the final product or its intermediate.

This invention also provides pharmaceutical compositions and formulations comprising one or more of the disclosed compounds in an amount sufficient, when administered to a warm-blooded mammalian subject having a disease or disorder mediated by aberrant CREB binding protein (CBP)/β-catenin signaling, to specifically inhibit the CBP/catenin mediated signaling within a warm-blooded mammalian subject. The amount of the administered compound preferably comprises a therapeutically effective amount, and in such cases the pharmaceutical compositions and formulations may comprise a therapeutically effective amount of the compound having the structure disclosed herein or a therapeutically acceptable salt thereof and a pharmaceutically acceptable carrier, diluent, or excipient therefor. All of these forms are encompassed within the scope of the present invention.

Definitions

"Lower", unless indicated otherwise, means that the number of the carbon atoms constituting the given radicals is between one and six.

"Halogen" means fluorine, chlorine, bromine or iodine.

"Halo" means fluoro, chloro, bromo or iodo.

"Alkyl" means a linear or branched, saturated, aliphatic radical having a chain of carbon atoms.

"Alkenyl" means a linear or branched, carbon chain that contains at least one carbon-carbon double bond.

"Alkynyl" means a linear or branched, carbon chain that contains at least one carbon-carbon triple bond.

"Alkylene", unless indicated otherwise, means a linear or branched, saturated, aliphatic, polyvalent carbon chain.

"Oxy" means the radical —O—. It is noted that the oxy radical may be further substituted with a variety of substituents to form different oxy groups including hydroxy, alkoxy, aryloxy, heteroaryloxy and the like.

"Phosphate" or "Phosphate salt" means $PO_3H_2$, or $PO_3^-$ and an appropriate counterion(s) (e.g., 1-2$Na^+$, 1-2$K^+$, or $Ca^{++}$, etc.), respectively.

"Thio" means the radical —S—. It is noted that the thio radical may be further substituted with a variety of substituents to form different thio groups including mercapto, alkylthio, arylthio, heteroarylthio and the like.

"Sulfinyl" means the radical —SO—. It is noted that the sulfinyl radical may be further substituted with a variety of substituents to form different sulfinyl groups including alkylsulfinyl, arylsulfinyl, heteroarylsulfinyl and the like.

"Sulfonyl" means the radical —$SO_2$—. It is noted that the sulfonyl radical may be further substituted with a variety of substituents to form different sulfonyl groups including alkylsulfonyl, arysulfonyl, heteroarylsulfonyl and the like.

"Alkoxy" means an oxygen moiety having a further alkyl substituent.

"Heteroatom" refers to an atom that is not a carbon atom and hydrogen atom. Particular examples of heteroatoms include, but are not limited to nitrogen, oxygen, and sulfur.

"Aryl" means a monocyclic or polycyclic radical wherein each ring is aromatic or when fused with one or more rings forms an aromatic ring.

"Heteroaryl" means a monocyclic or polycyclic aromatic radical wherein at least one ring atom is a heteroatom and the remaining ring atoms are carbon. "Cycloalkyl" means a non-aromatic, saturated or partially unsaturated, monocyclic, fused bicyclic or bridged polycyclic ring radical.

"Heterocycloalkyl" means cycloalkyl, as defined in this Application, provided that one or more of the atoms forming the ring is a heteroatom selected, independently from N, O, or S.

"Fused ring" as used herein refers to a ring that is bonded to another ring to form a compound having a bicyclic structure when the ring atoms that are common to both rings are directly bound to each other.

"Bridging ring" as used herein refers to a ring that is bonded to another ring to form a compound having a bicyclic structure where two ring atoms that are common to both rings are not directly bound to each other.

"Protected derivatives" means derivatives of compound in which a reactive site or sites are blocked with protecting groups. A comprehensive list of suitable protecting groups can be found in T. W. Greene, *Protecting Groups in Organic Synthesis,* 3rd edition, John Wiley & Sons, Inc. 1999.

"Isomers" mean any compound having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Animal" includes humans, non-human mammals (e.g., mice, rats, dogs, cats, rabbits, cattle, horses, sheep, goats, swine, deer, and the like) and non-mammals (e.g., birds, and the like).

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salt" or "salt" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like. Pharmaceutically acceptable salts also include base addition salts, which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Amount effective to treat" or "therapeutically effective amount" means that amount which, when administered to an animal for treating a disease, is sufficient to effect such treatment for the disease.

"Amount effective to prevent" means that amount which, when administered to an animal for preventing a disease, is sufficient to effect such prophylaxis for the disease.

"Treatment" or "treat" means any administration of a compound of the present invention and includes: (i) preventing the disease from occurring in an animal which may be predisposed to the disease but does not yet experience or display the pathology or symptomatology of the disease; (ii) inhibiting the disease in an animal that is experiencing or displaying the pathology or symptomatology of the diseased (i.e., arresting further development of the pathology and/or symptomatology); or (iii) ameliorating the disease in an animal that is experiencing or displaying the pathology or symptomatology of the diseased (i.e., reversing the pathology and/or symptomatology).

A "cosmeceutically effective amount" is amount which, when administered (e.g., transdermal, topically) is sufficient to affect cosmetic treatment of a cosmetic condition (e.g., wrinkles, hyperpigmentation, redness, rosacea, dryness, cracking, loss of vibrance, loss of elasticity, thinning, loss of vibrance, scarring, acne, sun damage, hair loss, loss of hair coloration, reduced cuticle growth, reduced nail growth).

Therapeutic Uses and Pharmaceutical Compositions of Compounds of the Present Invention According to aspects of present invention, exemplary diseases and conditions as discussed below, may be treated by modulating the common pathway (WNT-β-catenin signaling) shared by the disease states, regardless of cause or of tissue in which it is manifested. For example, treating a disease or disorder may comprise administering to a patient or a warm-blooded mammal, having a disease or disorder mediated by aberrant CREB binding protein (CBP)/β-catenin signaling, an amount of a compound of the present invention sufficient to inhibit CBP/catenin signaling and/or enhance p300/catenin mediated signaling.

The WNT-β-catenin pathway plays a crucial role in a broad array of diseases. Given the crucial role of WNT signaling in virtually every organ system in normal homeostasis and repair after injury, it is not surprising that aberrant regulation of this signaling cascade is associated with an array of diseases (see, e.g., Kahn, M., NATURE REVIEWS-|DRUG DISCOVERY VOLUME 13|July 2014|513). Beyond having an unequivocal role in multiple malignancies, aberrant WNT signaling is implicated as an important part in various other diseases, including neurological diseases, inflammatory and fibrotic disease, and disorders of endocrine function and bone metabolism in adults.

In particular aspects, aberrant WNT signaling is implicated in: cancer (e.g., cancer stem cell involvement in minimal residual disease in both solid (e.g., colon, pancreas, lung, liver, bladder, prostate, melanoma, glioma, medulloblastoma, osteosarcoma, uterine, endometrium and breast etc.) and liquid tumors (e.g., CML, CLL, AML, ALL etc.); in multiple myeloma; autoimmune disorders including Type I diabetes, rheumatoid arthritis, inflammatory bowel disease; topical disorders (e.g., psoriasis, vitiligo and atopic dermatitis); fibrosis including cardiac, liver, lung, kidney systemic and peritoneum (endometriosis) and ocular fibrosis; osteoarthritis and osteoporosis; metabolic diseases including Type II diabetes; hypertension; familial adenomatous polyposis; myelodysplastic syndrome (MDS); myeloproliferative proliferative neoplasms (MPN); CHIP (clonal hematopoiesis of indeterminate potential); pre-fibrotic conditions (e.g., AFLD, NASH, NAFLD, cirrhosis); polycystic kidney disease; polycystic ovary syndrome (PCOS), endometriosis, metabolic diseases; type II diabetes; hypertension; lung disorders (e.g., asthma and COPD); neurological diseases including, but not limited to neurodevelopment, autism, spectrum disorders, schizophrenia, and neurodegenerative disease including ALS, Huntington's, Parkinson's, Alzheimer's, frontotemporal dementia, multiple sclerosis (MS); and even more generally aging. The involvement of WNT signaling in particular representative diseases is outlined in more detail below.

Cancer. Aberrant regulation of WNT signaling has emerged as a recurrent theme in cancer biology. Constituents of WNT signaling can basically be characterized as either positively or negatively acting components, where the negatively acting components that principally act to suppress tumorigenesis are found mutated or in a loss-of-function status in cancer, whereas the positive components are activated. The discovery in 1991 that mutations in the tumor suppressor APC were associated with the vast majority of sporadic colorectal cancers via aberrant activation of WNT signaling provided considerable impetus to attempt to therapeutically target this pathway. Germ line defects in APC cause familial adenomatous polyposis, in which affected individuals develop hundreds of polyps in the large intestine at an early age and ultimately progress to colorectal cancer with 100% penetrance. Loss of function in both alleles of APC is required for tumorigenesis and is linked to the protein's ability to regulate β-catenin protein stability as well as chromosomal stability. APC is now noted as the most frequently mutated gene overall in human cancers. Mutations affecting the WNT pathway are not limited to colon cancer. For example, loss-of-function mutations in AXIN have been found in hepatocellular carcinomas, and oncogenic β-catenin mutations that were first described in colon cancer and melanoma were subsequently found to occur in a variety of solid tumors, including hepatocellular carcinomas, thyroid tumors and ovarian endometrioid adenocarcinomas. Epigenetic silencing is also frequently observed to alter levels of expression of negative regulators of the WNT-β-catenin pathway. For example, methylation of genes that encode putative extracellular WNT antagonists, such as the secreted Frizzled-related proteins (SFRPs), has been described in colon, breast, prostate, lung and other cancers. Increased expression of WNT ligands or effector proteins, including Dishevelled (DVL), has also been described. In particular, aberrant WNT signaling is implicated in cancer stem cells involved with minimal residual disease and relapse in both solid (e.g., colon, pancreas, lung, liver, bladder, prostate, melanoma, glioma, meduloblastoma, osteosarcoma, uterine, endometrium and breast etc.) and liquid tumors (e.g., CML, CLL, AML, ALL etc.). Specific small molecule CBP/β-catenin antagonists are effective in eliminating cancer stem cells, minimal residual disease and disease relapse (e.g. Kim, et al. Exp. Hematol. 2017 doi: 10.1016/j.exphem.2017.04.010). Furthermore, pre-malignancies and syndromes such as clonal hematopoiesis of indeterminate potential (CHIP), myelodysplastic syndrome (MDS), myelofibrosis (MF) and myeloproliferative neoplasms (MPN), Barrett's Esophagus, which are driven by defective stem cells, may be prophylactically eliminated by specific small molecule CBP/β-catenin antagonists (Thomas and Kahn Cell Biol. Toxicol. 2016 doi: 10:1007/s10565-016-9318-0).

Fibrosis. Fibrosis is characterized by an excessive accumulation of extracellular matrix components, which disrupts the physiological tissue architecture, leading to the dysfunction of the affected organ Fibrosis in general has been suggested to account for approximately 45% of deaths in industrialized countries, thereby highlighting the great medical need for effective antifibrotic therapies. Activated WNT-β-catenin signaling has been implicated in fibrosis in a number of organ systems, including the lungs, which indicates that this developmental pathway can be reactivated in adult tissues following injury. Specific small-molecule WNT modulation in several murine models of fibrosis (such as lung and kidney models) has proven to be extremely effective. Specific inhibition of the CBP-β-catenin interaction was shown to not only ameliorate but also to reverse late-stage fibrotic injury in murine models of lung, kidney, liver, cardiac, systemic fibrosis and endometriosis (Sci Rep. 2019 Dec. 27; 9(1):20056. doi: 10.1038/s41598-019-56302-4; Akcora et al., Biochim Biophys Acta Mol Basis Dis. 2018 March; 1864(3):804-818. doi: 10.1016/j.b-badis.2017.12.001; Xiao et al., Biochim Biophys Acta Mol Basis Dis. 2019 Jun. 1; 1865(6): 1313-1322. doi: 10.1016/j.bbadis.2019.01.027. Epub2019 Jan. 30; Zhao et al., Sci Rep. 2018 Jun. 12; 8(1):8996. doi: 10.1038/s41598-018-27064-2; Kimura et al., EBioMedicine 2017 September; 23:79-87. doi: 10.1016/j.ebiom.2017.08.016. Epub 2017 Aug. 19. Safety, Tolerability, and Preliminary Efficacy of the Anti-Fibrotic Small Molecule PRI-724, a CBP/β-Catenin Inhibitor, in Patients with Hepatitis C Virus-related Cirrhosis: A Single-Center, Open-Label, Dose Escalation Phase 1 Trial). In this trial the CBP/β-catenin antagonist PRI-724 administered by intravenous injection to patients with HCV cirrhosis at doses of 10 and 40 mg/m²/day for 12 weeks (1 week on and 1 week off) appeared to be safe, provided dose-dependent plasma exposure of the drug, and resulted in an improvement in liver histology and Child Pugh scores in several patients.

Pulmonary fibrosis. Pulmonary fibrosis destroys the lung's ability to transport oxygen and other gases into or out of the blood. This disease modifies the delicate and elastic tissues of the lung, changing these tissues into thicker, stiff fibrous tissue. This change or replacement of the original tissue is similar to the permanent scarring that can occur to other damaged tissues. Scarring of the lung reduces the lung's ability to allow gases (i.e. oxygen, carbon dioxide) to pass into or out of the blood. Gradually, the air sacs of the lungs become replaced by fibrotic tissue. When the scar forms, the tissue becomes thicker causing an irreversible loss of the tissue's ability to transfer oxygen into the bloodstream. Symptoms include shortness of breath, particularly with exertion; chronic dry, hacking cough; fatigue and weakness; discomfort in the chest; loss of appetite; and rapid weight loss. Several causes of pulmonary fibrosis are known and they include occupational and environmental exposures. Many jobs, particularly those that involve mining or that expose workers to asbestos or metal dusts, can cause pulmonary fibrosis. Workers doing these kinds of jobs may inhale small particles (like silica dusts or asbestos fibers) that can damage the lungs, especially the small airways and air sacs, and cause the scarring associated with fibrosis. Agricultural workers also can be affected. Some organic substances, such as moldy hay, cause an allergic reaction in the lung. This reaction is called Farmer's Lung and can cause pulmonary fibrosis. Other fumes found on farms are directly toxic to the lungs. Another cause is Sarcoidosis, a disease characterized by the formation of granulomas (areas of inflammatory cells), which can attack any area of the body but most frequently affects the lungs. Certain medicines may have the undesirable side effect of causing pulmonary fibrosis, as can radiation, such as treatment for breast cancer. Connective tissue or collagen diseases such as systemic sclerosis are also associated with pulmonary fibrosis. Although genetic and familial factors may be involved, this cause is not as common as the other causes listed above. In Chronic Obstructive Pulmonary Disease (COPD), connective tissue proliferation and fibrosis can characterize severe COPD. COPD can develop as a result of smoking or chronic asthma.

Idiopathic Pulmonary Fibrosis (IPF). When all known causes of interstitial lung disease have been ruled out, the condition is called "idiopathic" (of unknown origin) pulmonary fibrosis (IPF). Over 83,000 Americans are living with IPF, and more than 31,000 new cases develop each year. This debilitating condition involves scaring of the lungs. The lungs' air sacs develop scar, or fibrotic tissue, which gradually interferes with the body's ability to transfer the oxygen into the bloodstream, preventing vital organs and tissue from obtaining enough oxygen to function normally. There are several potential causes of IPF, including viral illness e.g., SARS-CoV-2 and allergic or environmental exposure (including tobacco smoke). There is also a familial form of the disease, known as familial idiopathic pulmonary fibrosis. Patients with IPF suffer similar symptoms to those with pulmonary fibrosis when their lungs lose the ability to transfer oxygen into the bloodstream. The symptoms include shortness of breath, particularly during or after physical activity; spasmodic, dry cough; gradual, unintended weight loss; fatigue and weakness; chest discomfort; clubbing, or enlargement of the ends of the fingers (or sometimes the toes) due to a buildup of tissue. These symptoms can greatly reduce IPF patients' quality of life. Pulmonary rehabilitation, and oxygen therapy can reduce the lifestyle-altering effects of IPF, but do not provide a cure.

Diabetes and Metabolic Diseases. Wnt signaling is critically important not only in stem cell maintenance, differentiation, and migration, but also in organogenesis. WNT signaling also has crucial roles in various endocrine functions and has therefore been implicated in several endocrine disorders. WNT signaling is important in the regulation of insulin sensitivity and its dysregulation is implicated in the development of diabetes. In particular, WNT10B increases insulin sensitivity in skeletal muscle cells. Overexpression of WNT5B induces adipogenesis. Decreased expression of β-catenin-independent WNT5B, which has been demonstrated in patients with type 2 diabetes, may increase susceptibility to type 2 diabetes. β-catenin/TCF7L2-dependent Wnt signaling (the canonical pathway) is involved in pancreas development, islet function, and insulin production and secretion. Glucagon-like peptide-1 (GLP-1) and the chemokine stromal cell-derived factor-1 (SDF1) modulate canonical Wnt signaling Additionally, polymorphisms in the transcription factor TCF7L2 (also known as TCF4), are linked to increased susceptibility to type 2 diabetes. Individuals with at-risk alleles of TCF7L2 exhibit impaired insulin secretion, and TCF7L2 in pancreatic β-cells appears to have a crucial role in glucose metabolism through the regulation of pancreatic β-cell mass.

Experimental loss of TCF7L2 function in islets impairs glucose-stimulated insulin secretion, suggesting that perturbations in the Wnt signaling pathway may contribute substantially to the susceptibility for, and pathogenesis of, T2D. Interestingly, nicotine has been shown to enhance renal cell proliferation and fibronectin production under high glucose partly via activating the Wnt/β-catenin pathway. Increased Wnt/CBP/β-catenin signaling may initially induce pancreatic β-cell expansion; however, continuous Wnt driven mitogenic signaling may eventually lead to a loss of differentiation capacity and functionality.

Recently, researchers treated cadaver-derived intact human islets with conditioned medium from L-cells that constitutively produced WNT3A, R-spondin 3 and Noggin, to which inhibitors of RHO-associated protein kinase (ROCK) and RHOA were added to augment cell survival. This led to an approximately 20-fold increase in β-cell proliferation compared with glucose alone. Importantly, treatment with this conditioned medium did not impair glucose-stimulated insulin secretion or decrease the insulin content of the cells. In transcriptome-wide gene expression profiling and follow-up signaling studies, the researchers showed that the conditioned media treatment specifically promoted WNT signaling.

Neurological diseases. The importance of WNT signaling during embryonic development of the central nervous system is well established. The WNT pathway also regulates nervous system patterning and the regulation of neural plasticity. WNTs also have a role in axon guidance as well as in influencing synapse formation. Therefore, it is not surprising that aberrations in WNT signaling have been observed in neurological diseases in adulthood. For example, a Scottish family with a high incidence of schizophrenia, depression and bipolar disorder was found to carry a balanced chromosomal translocation involving the gene DISC1 (disrupted in schizophrenia 1). Subsequently, the protein product of DISC1 was found to have an important role in neural development and neural progenitor proliferation. DISC1 directly interacts with and inhibits GSK3β activity, thereby enhancing β-catenin-mediated transcription.

Neuroanatomical observations and functional magnetic resonance imaging (MRI) have indicated that a major pathological hallmark in autistic individuals may be a premature overgrowth of the cerebral cortex, hippocampus, amygdala and cerebellum. Interestingly, transgenic mice expressing a constitutively active form of β-catenin in neuronal precursor cells developed a grossly enlarged cerebral cortex, hippocampus and amygdala. Importantly, microdeletion and microduplication copy number variations of genes involved in the canonical WNT signaling pathway (for example, Frizzled 9 (FZD9), B cell lymphoma 9 (BCL9) or cadherin 8 (CDH8)) are found in patients with autism spectrum disorder. Association studies investigating WNT2, DIS1, MET, dedicator of cytokinesis protein 4 (DOCK4) or Abelson helper integration site 1 (AHI1; also known as jouberin) have provided additional evidence that the canonical WNT pathway might be affected in autism.

The WNT signaling cascade has also been implicated in Alzheimer's disease. Presenilin proteins, which have been associated with early-onset Alzheimer's disease, are negative regulators of canonical WNT signaling. Variant alleles in the WNT receptor LRP6 (low-density lipoprotein receptor-related protein 6) have been associated with Alzheimer's disease in population-based linkage analyses. This suggests that multiple mechanisms leading to aberrant WNT-mediated regulation of adult neurogenesis may be associated with Alzheimer's disease. As the underlying cause (or causes) of Alzheimer's disease have not been clearly elucidated, the mechanisms whereby aberrant WNT regulation may have a role in Alzheimer's disease are also not known. WNT signaling is involved in brain vascularization and blood-brain barrier formation, in synaptogenesis, in amyloid-β-induced neuroinflammation and neurotoxicity, as well as in neuronal degeneration. Aberrant regulation of any or all of these processes could contribute to disease initiation and progression.

Skin. The WNT signaling cascade has also been implicated in skin development and maintenance (see, e.g., STEM CELLS 2018; 36:22-35). Secreted Wnt proteins can stimulate multiple intracellular signaling pathways and act as growth factors that regulate diverse processes, including cell proliferation, differentiation, migration, and polarity. Among Wnt stimulated pathways, Wnt/β-catenin signaling is known as an important regulatory pathway that governs developmental processes and fate choices during tissue morphogenesis. Wnt signaling is one of the major cues directing skin development and maintenance. Although Wnt signaling has been mainly implicated in HF (Hair Follicle) induction during skin development, it has also been recently shown to regulate epidermal stratification. In primary human keratinocytes, Wnt5a acts as an autocrine stimulus to promote extracellular calcium-induced keratinocyte differentiation by coupling with Wnt/β-catenin pathway. Throughout life the skin epidermis is regularly renewed. Skin epidermal SCs, capable of self-renewal and differentiation, provide unlimited sources of cells to maintain tissue homeostasis, as well as to regenerate HFs and repair the epidermis after injury. Wnt signaling is critical in all of these processes and Wnt dependent signaling plays crucial roles in the maintenance, activation, and fate determination of the SC populations.

Vaccine (e.g., SARS-CoV-2 (COVID-19), Influenza, Etc.) Enhancement

Age. With age, the immune system loses some of its vigor (immunosenescence, reflected by fewer naïve T cells, and B cells), which is believed to contribute to the higher vulnerability to COVID-19 and more generally infection in older age subject groups (e.g., ≥60 yrs or ≥65 yrs, for humans). Additionally, vaccines may perform poorly in such older subject groups, which often experience chronic inflammation (inflammaging, characterized by impaired clearance of dead and dying cells from sites of immune activity, and high baseline serum concentrations of C reactive protein (CRP) and cytokines, e.g., interleukin-6 (IL-6), and IL-8)), which factors may inhibit antigen-specific (e.g., anti-viral) immunity, e.g., influenza virus (Willyard, C., *Nature* Vol. 586, 2020; Akbar & Gilroy, *Science* 369 (6501), 256-257, 2020, DOI: 10.1126/science.abb0762; A. Parmigiani et al., *PLOS ONE* 8, e79816 (2013)).

Current influenza vaccination strategies prioritizing elderly persons (55 to 75 yrs) have been found to be less effective than believed at reducing serious morbidity and mortality in this population, suggesting that supplementary strategies to boost the effectiveness of vaccination, essentially dependent on immune memory and recall, may be necessary (Anderson et al., *Ann Intern Med.* 2020; 172:445-452. doi:10.7326/M19-3075).

Likewise, SARS-CoV-2 causes severe respiratory disease (coronavirus disease 2019, COVID-19) that mostly induces mild to moderate symptoms in younger individuals, but induces devastating morbidity and mortality in older individuals. A key hallmark of severe disease is exuberant inflammation in the respiratory tract of patients (Merad & Martin, *Nat. Rev. Immunol.* 20, 355, 2020).

Memory T cells. A hallmark of the aging immune system is its failure to induce long-lived memory (Kim, Chulwoo, et al., Cell Reports 25, 2148-2162, Nov. 20, 2018). Moreover, enforcing asymmetric cell division (ACD) rates can improve long-term survival and function of T cells and open new perspectives for vaccination (Borsa, et al., *Sci. Immunol.* 4, eaav1730 (2019). It has been demonstrated that asymmetric cell division is responsible for the dichotomy between the generation of memory T cells and effector cells from a common precursor activated by antigenic recognition in the context of an antigen-presenting cell (Morrot, Alexandre, *Ann Transl Med* 2017; 5(5): 121; citing Verbist K C, Guy C S, Milasta S, et al. Metabolic maintenance of cell asymmetry following division in activated T lymphocytes (Nature 2016; 532:389-93)). Moreover, memory T cells appear to use asymmetric cell division to generate cellular heterogeneity when faced with pathogen rechallenge (Ciocca, Maria, L. et al., The Journal of Immunology, 2012, 188: 4145-4148).

Currently suggested approaches to vaccine enhancement may involve the use of vaccine adjuvants, higher doses of viral antigen, or identification of drugs that might improve vaccine responses in older population group (e.g., rejuvenating the immune system). For example, mTOR inhibitors (Mannick, J. B. et al. *Sci. Transl. Med.* 10, 449, eaaq1564, 2020) (e.g., RTB101, rapamycin, metformin) have been proposed. Anti-inflammatory drugs (e.g., losmapimod, dexamethasone), and senolytics (e.g., fisetin) have also been proposed for boosting immunity.

There is, however, yet an urgent need, for more effective compositions and methods for enhancing vaccine (e.g., anti-viral vaccines for e.g., influenza, SARS, SARS-CoV-2, HPV, HEP-A, HEP-B, Herpes Zoster, etc.) response, for example, e.g., by; metabolic maintenance of cell asymmetry following division in activated T cells in the subject; and/or enhancing antigen-specific immunity by increasing the number and/or persistence of differentiated memory T-cells; and/or enhancing the presentation of antigens to T-cells by antigen presenting cells to enhance cooperativity between the innate and acquired immune systems (Ljungberg, Johanna K. et al, Front, of Immunol. 10; 2521, 2019), particularly in elderly subjects (e.g., 55-75; ≥60 yrs; ≥65 yrs).

CBP/Cateriin inhibitors. PRI-724 (a specific CBP/β-catenin inhibitor) treatment of ART-suppressed SIVmac251-infected RMs has been shown to decrease proliferation of T memory stem cells (SCM) and central memory T-cells (CM) T-cells and modify the SCM and CM CD4+ T-cell transcriptome towards a profile of more differentiated memory T-cells, demonstrating that sternness pathways of long-lived memory CD4+ T-cells can be pharmacologically modulated in vivo, thus establishing a novel strategy to target HIV persistence (Mavigner, M. et al., J. Virol, doi: 10.1128/JVI.01094-19).

According to particular aspects of the present invention, there is a need for safe and effective methods of treatment (e.g., prophylactic and/or therapeutic) to target fundamental ageing mechanisms at around the time of "vaccination".

According to particular aspects of the present invention, the disclosed CBP/Catenin inhibitors have substantial utility for enhancing vaccination (e.g., anti-viral vaccines for e.g., influenza, SARS, SARS-CoV-2, HPV-A, HPV-B, Herpes Zoster etc.), particularly in aged individuals (e.g., 55-75; ≥60 yrs; ≥65 yrs), e.g., by: metabolic maintenance of cell asymmetry following division in activated T cells in the subject; and/or enhancing antigen-specific immunity by increasing the number and/or persistence of differentiated memory T-cells; and/or enhancing the presentation of antigens to T-cells by antigen presenting cells to enhance cooperativity between the innate and acquired immune systems, particularly in elderly subjects (e.g., 55-75; ≥60 yrs; ≥65 yrs). According to further aspects, the compounds may be administered prophylactically and/or therapeutically, including administration as a primer before vaccination, and/or co-administration with vaccination, and/or administration or co-administration (e.g., along with a vaccine booster) subsequent to initial vaccination.

According to further aspects, the compounds may be used to enhance vaccination in mammalian (e.g., human) subjects with any vaccine.

SARS-CoV-2 (COVID-19) Tissue (Lung, Liver, Kidney, Heart, Etc.) Destruction (e.g., Pulmonary Fibrosis, ARDS)

As discussed above, inflammaging has many implications for COVID-19 patients (e.g., as discussed in Akbar & Gilroy, supra). While accumulation of senescent cells in the respiratory tract of older patients may be involved in the initiation of an inflammatory cascade that could inhibit T cell responses to virally infected cells that are present, high amounts of inflammation alone do not explain the devastating tissue destruction that is observed in the lungs of COVID-19 patients with severe disease, and it may be that age-associated changes in T cells have a role in the immunopathology. T lymphocytes that are highly differentiated and exhibit senescence-like characteristics accumulate in older individuals. While these aged T cells lose the capacity to proliferate after activation and express multiple markers of senescence, including DNA damage associated proteins [e.g., phosphorylated histone H2AX (gH2AX)] and cyclin-dependent kinase inhibitors (e.g., p16INK4A), they are nonetheless highly efficient cytotoxic cells, express NKRs, and can kill different cell types that express NKR ligands, including senescent non-lymphoid cells. Another consequence of the inflammation is the induction of NKR ligand expression by cells in the lung that would make them susceptible to killing by infiltrating T cells that express NKRs (Id).

Lung Fibrosis. Almost all COVID-19-related serious consequences feature pneumonia, and many have ground glass opacities, etc., many (about 40%) developing acute respiratory distress syndrome (ARDS). There is a concern that some organs, including the lungs, might have long-term impairment following infection, inflammation and lack of resolution (e.g., pulmonary fibrosis, which is a recognized sequelae of ARDS). Mechanical ventilation is the most important supportive therapy for patients with ARDS, including COVID-19 patients, but it can induce or aggravate lung injury, referred to as ventilator-induced-lung-injury (VILI) (Slutsky and Ranieri NEJM 2013). Although the virus is eradicated in patients who have recovered from COVID-19, the removal of the cause of lung damage does not, in itself, preclude the development of progressive, fibrotic irreversible interstitial lung disease. Furthermore, even a relatively small degree of residual but non-progressive fibrosis could result in considerable morbidity and mortality in an older population of patients who had COVID-19, many of whom will have pre-existing pulmonary conditions (Bern, Reinout A; https://doi.org/10.1016/S2213-2600(20)30222-8). The description of the group in whom SARS-CoV-2 infection is most lethal is also highly representative of patients suffering with idiopathic pulmonary fibrosis (IPF). Anti-fibrotic therapies that are available or in development could have value in preventing severe COVID-19 in patients with IPF, have the potential to treat severe COVID-19 in patients without IPF, and might have a role in preventing fibrosis after SARS-CoV-2 infection (George et al, Lancet August 2020).

Acute lung injury and ARDS are the major cause of mortality in COVID-19. While conventional therapy may be possible with such agents as pirfenidone and nintedanib, pirfenidone and nintedanib are currently commercially available only in oral form and so cannot be used in patients who are intubated and mechanically ventilated, thereby restricting their use in those individuals with severe COVID-19 on the intensive care unit (ICU). Further, pirfenidone should be avoided if patients have an estimated glomerular filtration rate of less than 30 mL/min per 1.73 m$^2$. Moreover, both pirfenidone and nintedanib can be associated with hepatotoxicity, and liver dysfunction is common in patients infected with SARS-CoV-2. A further uncertainty relates to the rapidity (rate) with which antifibrotic agents act, where known agents may have little value in ventilated patients where the opportunity for effective treatment has already passed (Id).

According to particular aspects of the present invention, there is a need for safe and effective methods of treating (e.g., prophylactic and/or therapeutic) SARS-CoV-2 (COVID-19) lung tissue destruction (e.g., pulmonary fibrosis, ARDS).

As summarized above under "THERAPEUTIC USES AND PHARMACEUTICAL COMPOSITIONS OF THE PRESENT INVENTION" (pg. 29-34), the utility of CBP/β-Catenin inhibitors for treating aspects of fibrosis has been recognized.

According to particular aspects of the present invention, therefore, the disclosed CBP/Catenin inhibitors have substantial utility, particularly in aged individuals (e.g., 55-75; ≥60 yrs; ≥65 yrs), for treating SARS-CoV-2 (COVID-19) tissue (e.g., lung, liver, etc.) destruction (e.g., pulmonary fibrosis, ARDS), including both in the acute phase of the illness and in preventing long-term complications. According to further aspects, the compounds may be administered prophylactically and/or therapeutically, in either case preferably initiated before or within the first 1-3 weeks, preferably initiated before or within the first week, of ARDS onset.

Administration:

The pharmaceutical composition of the present invention is formulated to be compatible with its intended route of administration. Examples of routes of administration include parenteral, e.g., oral (e.g., in capsules or tablets), intravenous, intradermal, subcutaneous, inhalation, transdermal (topical), transmucosal, and rectal administration. Solutions or suspensions (e.g., injection) used for parenteral (particularly, intravenous), intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. In addition, pH may be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound, e.g., a compound having general formula (Ia) in the required amount, in an appropriate solvent with one or a combination of ingredients enumerated above, as required, followed by filtered sterilization. Generally, dispersions are prepared by incorporating the active compound into a sterile vehicle that contains a dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent I such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In particular embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers.

It can be advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. For instance, in certain embodiments, a pharmaceutical composition of the present invention is one suitable for oral administration in unit dosage form such as a tablet or capsule that contains from about 1 mg to about 10 g of the compound of this invention. In some other embodiments, a pharmaceutical composition of the present invention is one suitable for intravenous, subcutaneous or intramuscular injection. A patient may receive, for example, an intravenous, subcutaneous or intramuscular dose of about 1 µg/kg to about 1 g/kg of the compound of the present invention. The intravenous, subcutaneous and intramuscular dose may be given by means of a bolus injection or by continuous infusion over a period of time. Alternatively a patient will receive a daily oral dose approximately equivalent to the daily parenteral dose, the composition being administered 1 to 4 times per day.

The compounds may be administered intravenously (e.g., by continuous drip infusion or rapid intravenous administration) to mammals inclusive of human. In such case, the dose may be selected appropriately depending on various factors such as the body weight and/or age of patients, and/or the degree of the symptom and an administration route. For example, the dose of the compound for intravenous administration is generally in the range of 1 to 10000 mg/day/m$^2$ human body surface area, preferably in the range of 1 to 5000 mg/day/m$^2$ human body surface area, and more preferably 10 to 5000 mg/day/m$^2$ human body surface area by continuous drip infusion administration.

These therapeutic agents may be administered according to how often per day (one or more times per 24 hour period), including the time between doses (e.g. every 6 hours), the times when the doses are to be administered (e.g. at 8 a.m. and 4 p.m. daily) and the amount of the therapeutic agent (e.g. number of capsules) to be given at a specific time.

WORKING EXAMPLES

An illustration of the preparation of exemplary compounds of the present invention is shown in the representative examples and schemes below, wherein specific non-limiting working Examples of compounds are intended to illustrate particular exemplary embodiments of the present invention, and are not intended to limit the scope of the specification or the claims in any way. The compounds of the present invention may be prepared by the synthetic sequences shown in the non-limiting Examples and Schemes below. A skilled artisan will appreciate that other routes of synthesis may be employed as well. In particular, other routes of synthesis may in fact be applied to certain aspects of the present invention. The skilled artisan is referred to general textbooks, such as March's Advanced Organic Chemistry (Michael B. Smith & Jerry March, Wiley-Interscience, 2000), The Practice of Medicinal Chemistry (Camile G. Wermuth, Academia Press, 2003) and Protective Groups in Organic Synthesis (Theosora W. Greene & Peter G. M. Wuts; John Wiley & Sons Inc, 1999), all incorporated by reference herein for their respective teachings.

Example 1

Reagents, Synthetic Methods, and Biological Characterization Assay Used

Unless otherwise noted, all reagents, starting materials and solvents were obtained from commercial suppliers and used without further purification. Concentration or evaporation refers to evaporation under vacuum using a Buchi rotatory evaporator, and/or followed by evaporation to dryness under high vacuum. Reaction products were purified by silica-gel chromatography with the solvent system indicated, or by HPLC purification using a C18 reverse phase semi-preparative HPLC column with solvent A (0.1% of TFA in water) and solvent B (0.1% of TFA in $CH_3CN$) as eluents. All final products have at least 95% purity as determined by analytical HPLC analysis with UV detection at 210 nm and/or 254 nm. Reported yields are isolated yields.

Analytical HPLC analysis was performed on an Agilent 1100 HPLC with a Phenomenex Luna C18 (2) column (3 micron, 150×4.6 mm id) at a flow rate of 0.6 mL/min, eluting with a binary solvent system A and B using a 10%-90% B in 20 min and then 90%-95% B in 5 min gradient elution (gradient elution 1), or a 70%-95% B in 25 min and then 95%-100% B in 3 min gradient elution (gradient elution 2) (A: Milli-Q water with 0.1% TFA; B: $CH_3CN$ with 0.1% TFA) with initial operating pressure in the range of 120 to 140 bar. NMR spectra were recorded on a Bruker AV-300 or AV-301 300 MHz NMR instrument using DMSO-$d_6$ or $CDCl_3$ with TMS as an internal standard. Mass spectra data was obtained with Bruker Esquire Liquid Chromatography-Ion Trap Mass Spectrometer.

The following abbreviations are used in the synthetic examples: aq (aqueous), h (hour), min (minutes), sat'd (saturated), THF (tetrahydrofuran), rt (room temperature), Et$_3$N (triethylamine), NaCl (sodium chloride), MgSO$_4$ (magnesium sulfate), CDCl$_3$ (deuterated chloroform), H$_2$O (water), HCl (hydrochloric acid), MeOH (methanol), NaOH (sodium hydroxide), TFA (trifluoroacetic acid), Na$_2$CO$_3$ (sodium carbonate), CH$_2$Cl$_2$ (methylene chloride), EtOAC (ethyl acetate), DMF (dimethylformamide), EtOH (ethanol), DMSO (dimethyl sulfoxide), DMSO-$d_6$ (dimethyl sulfoxide-$d_6$), NaHCO$_3$ (sodium bicarbonate), HPLC (high performance liquid chromatography), ESI-MS or MS (ESI) (electrospray ionization-mass spectrometry), NMR (nuclear magnetic resonance), DIEA (diisopropylethylamine), brine (saturated aqueous NaCl solution), NH$_4$Cl (ammonium chloride), Boc$_2$O (di-tert-butyl dicarbonate), HATU (1-[Bis(dimethylamino)methylene]-1H-1,2,3-triazolo[4,5-b]pyridinium 3-oxide hexafluorophosphate), NaI (sodium iodide), KI (potassium iodide), Pd(OAc)$_2$ (Palladium(II) acetate), BINAP (2,2'-bis(diphenylphosphino)-1,1'-binaphthyl), DIEA or DIPEA (N,N-diisopropylethylamine), DCC (dicyclohexylcarbodiimide), NCS (N-chlorosuccinimide), PPTS (pyridinium p-toluenesulfonate), and other similar standard abbreviations are used herein.

Biological Characterization of Exemplary Compounds of the invention were performed in at least the following assays:

SuperTOPFLASH Cell-based Luciferase Assay. Hek-293, STF1.1 cells are maintained in DMEM, 10% FBS, Pen-Strep supplemented with 200 µg/mL G418. On the day prior to assay, cells are split into a white, opaque 96-well plate at 10,000 cells per well in 50 µL of complete medium without G418 (for screening of Wnt-signaling inhibitors, G418 can be left out during screening process). After allowing the cells to stabilize and attach overnight, 40 µL of complete medium (without G418) containing 2.5× final concentration of compound or DMSO control is added to the cells and allowed to incubate for 1 hour at 37° C., 5% CO$_2$ prior to adding 10 µL of a 100 mM LiCl solution prepared in complete medium (without G418). After 24 hours, 100 µL of BrightGlo (Promega, Cat. #: G7573) is added to each well and the plate is shaken for 5 minutes prior to reading on the Perkin-Elmer EnVision Plate Reader. For example, on the day prior to assay: cells are split into a white opaque 96-well plate at 10,000 cells per well in 50 µL of complete growth medium; the plate is incubated overnight at 37° C., 5% $CO_2$ and the cells allowed to attach; the next day inhibitors to be tested are prepared in complete growth medium at 2.5× the desired final concentration (all conditions are done in duplicates), and 40 µL of the medium containing the 2.5× concentration of compound is added to each well (include 2 wells for stimulation control, 2 wells for DMSO control, and wells for the positive control ICG-001 (e.g., 2, 5, and 10 micromolar)); once all inhibitors and controls are added, incubate the plate for 1 hour at 37° C., 5% $CO_2$ (while plate is incubating, prepare fresh 100 mM LiCl in complete growth medium); after 1 hour, the plate is removed from the incubator and 10 µL of the medium containing 100 mM LiCl are added to each well (except for the two wells of the unstimulated control, to which 50 microliters of just complete medium is added); the plate is incubated for 24 hours at 37° C., 5% $CO_2$; after 24 hours, 100 microliters of BrightGlo (Promega, Cat. #: G7573) is added to each well, the plate is shaken for 5 minutes to ensure complete lysis, and the plate is then read on a Perkin-Elmer EnVision 96-well plate reader.

Assay of Human Survivin 1 Kb-promoter-driven Luciferase Activity in Stably Transfected Cell Line, 1 Kb Hu-survivin\luc-Hek293. In brief, 1 Kb Hu-survivin\luc-Hek293 cells are maintained in DMEM, 10% FBS, Pen-Strep supplemented with 1 µg/mL puromycin. On the day prior to assay, cells are split into a white, opaque 96-well plate at 10,000 cells per well in 50 µL of complete medium without puromycin (for screening of CBP/β-catenin interaction inhibitors, puromycin can be left out during screening process). After allowing the cells to stabilize and attach overnight, 50 µL of complete medium (without G418) containing 2× final concentration of compound or DMSO control is added to the cells. After 24 hours, 100 µL of BrightGlo (Promega, Cat. #: G7573) is added to each well and the plate is shaken for 5 minutes prior to reading on the Perkin-Elmer EnVision Plate Reader. For example, on the day prior to assay, cells are split into a white opaque 96-well plate at 10,000 cells per well in 50 µL of complete growth medium; the plate is incubated overnight at 37° C., 5% $CO_2$ and the cells allowed to attach; next day the inhibitors to be tested are prepared in complete growth medium at 2× the desired final concentration (all conditions are done in duplicate), and 50 µL of the medium containing the 2× concentration of compound is added to each well (include 2 wells for stimulation control, 2 wells for DMSO control, and wells for the positive control ICG-001 (e.g., 2, 5, 10, and 20 µM), and the plate is then incubated for 24 hours at 37° C., 5% $CO_2$; after 24 hours, 100 µL of BrightGlo (Promega, Cat. #: G7573) is added to each well, the plate is shaken for 5 minutes to ensure complete lysis, and read on a Perkin-Elmer EnVision 96-well plate reader.

Example 2

Synthesis of (S)-2-amino-3-(4-tert-butoxyphenyl)-N-(2,2-diethoxyethyl)-N-(quinolin-5-ylmethyl)propanamide (1)

Compound 1 as a faint-yellow oil was prepared according to the procedures disclosed in U.S. Pat. No. 7,671,054, as shown in Scheme 1, starting from quinoline-5-carboxaldehyde. MS (ESI): m/z 494.2 (M+H)$^+$.

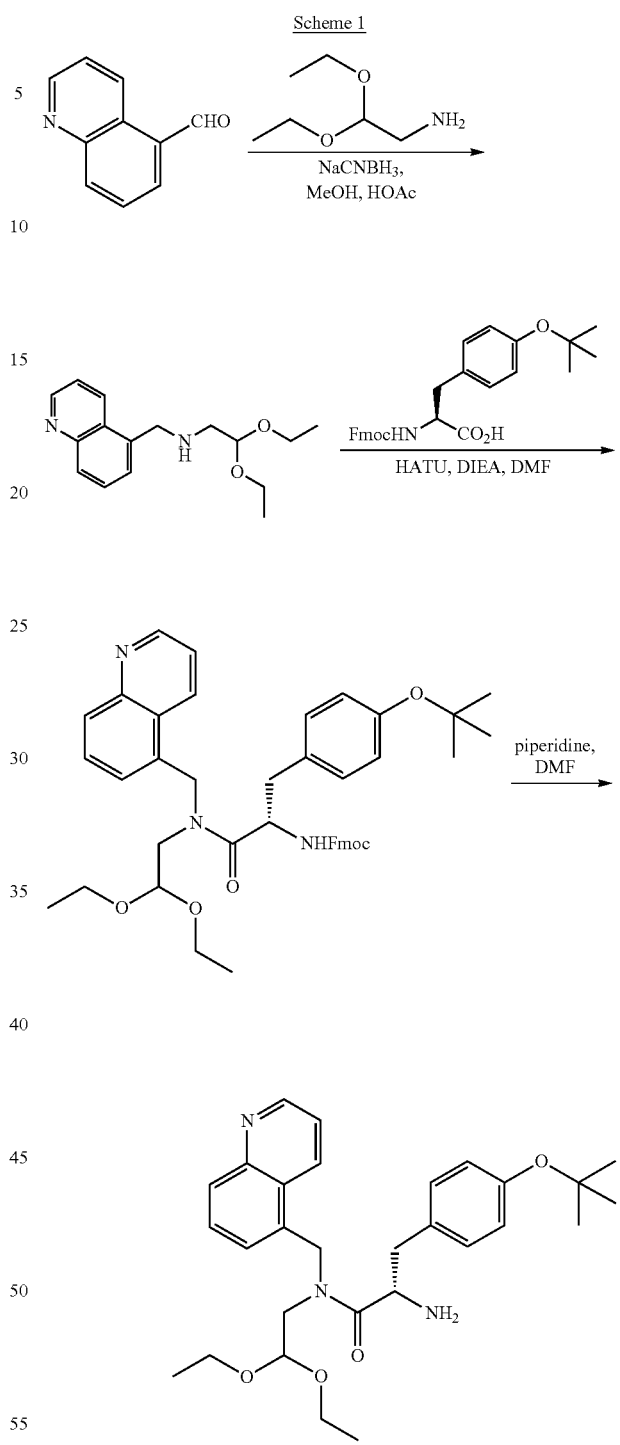

Synthesis of (S)-2-amino-3-(4-tert-butoxyphenyl)-N-(2,2-diethoxyethyl)-N-(naphthalen-1-ylmethyl)propanamide (2)

Compound 2 as a colorless oil was prepared according to the procedures disclosed in U.S. Pat. No. 7,671,054, as shown in Scheme 2, starting from 1-naphthaldehyde. MS (ESI): m/z 493.3 (M+H)$^+$.

Scheme 2

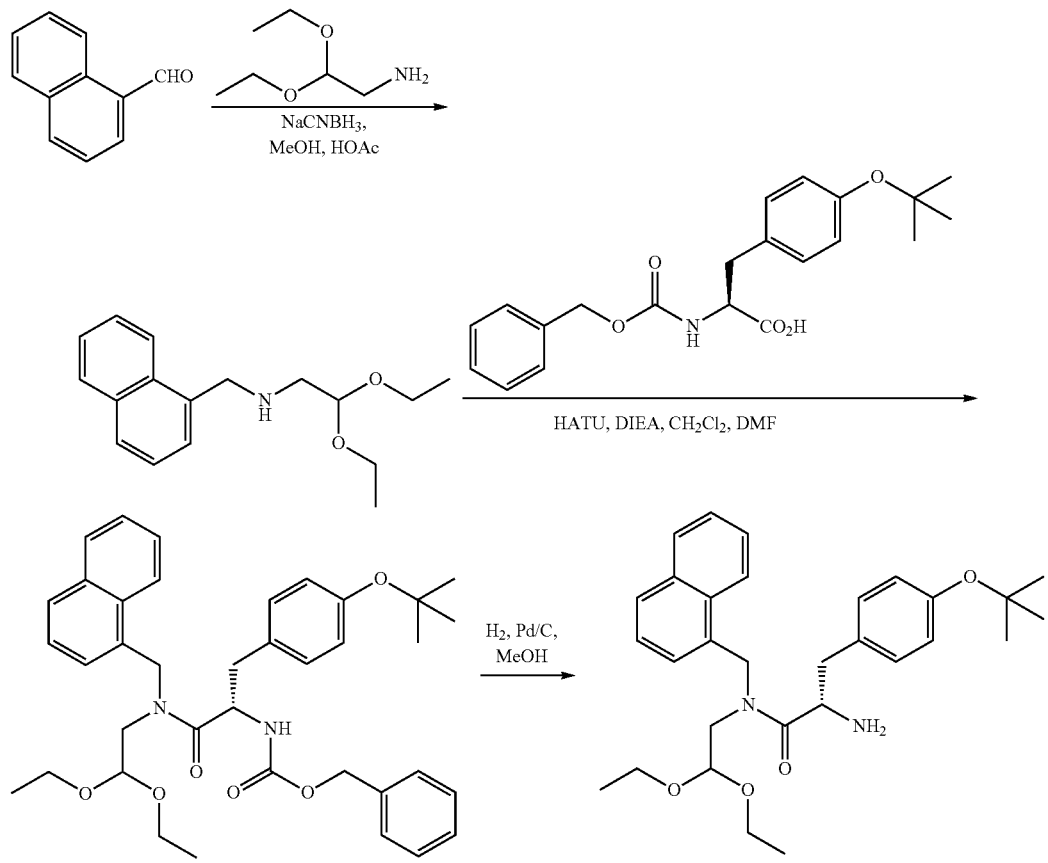

Example 4

Synthesis of tert-butyl 2-(2-(benzylcarbamoyl)hydrazinyl)acetate (3)

Compound 3 was prepared according to the procedures set forth in steps 1-3 of Scheme 3 below.

Scheme 3

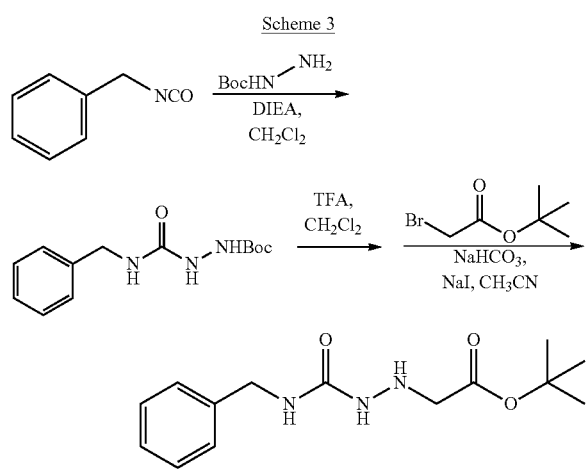

Step 1: tert-butyl 2-(benzylcarbamoyl)hydrazinecarboxylate

To a solution of tert-butyl hydrazinecarboxylate (2.5 g, 19 mmol) in dry $CH_2Cl_2$ (50 mL) at 0° C. was added DIEA, followed by dropwise addition of benzyl isocyanate (2.35 mL, 19 mmol). The reaction mixture was stirred at room temperature under argon overnight, and then taken into $CH_2Cl_2$ (150 mL) and 10% $KHSO_4$ (100 mL). The organic layer was washed with sat'd $NaHCO_3$ (100 mL), sat'd NaCl (100 mL), dried ($MgSO_4$) and evaporated to dryness. The title compound (5.4 g) as a white solid was used in the next step without further purification. $^1$H-NMR (300 MHz, DMSO-$d_6$) δ 8.54 (br s, 1H), 7.70 (s, 1H), 7.26 (m, 5H), 6.81 (brs, 1H), 4.22 (d, J=6 Hz, 2H), 1.40 (s, 9H).

Step 2: N-benzylhydrazinecarboxamide

The tert-butyl 2-(benzylcarbamoyl)hydrazinecarboxylate (5.4 g) was treated in $CH_2Cl_2$ (50 mL) and TFA (50 mL) at room temperature under argon over 3 hours. Evaporation and co-evaporation with $CHCl_3$ twice to dryness gave the title compound (TFA salt; 5.6 g) as a pale-yellow solid, which was used in the next step without further purification. $^1$H-NMR (300 MHz, DMSO-$d_6$) δ 7.24 (m, 5H), 7.03 (brs, 1H), 6.82 (brs, 1H), 4.24 (m, 4H).

Step 3: tert-butyl 2-(2-(benzylcarbamoyl)hydrazinyl)acetate

To a suspension of N-benzylhydrazinecarboxamide (5.6 g) in dry $CH_3CN$ (38 mL) was added $NaHCO_3$ (4.8 g, 57 mmol), tert-butyl 2-bromoacetate (4.2 mL, 28.5 mmol) and NaI (0.28 g). The reaction mixture was stirred at 60° C. under argon over 24 h, and taken into EtOAc (100 mL). The insoluble materials were filtered. The filtrate was washed with water (100 mL). The aqueous layers were further extracted with EtOAc. The combined organic extracts were dried (Na$_2$SO$_4$) and evaporated to dryness. Purification by silica gel chromatography using EtOAc/CH$_2$Cl$_2$ (25% and 50%) afforded the title compound (2.3 g) as a white solid. $^1$H-NMR (300 MHz, CDCl$_3$) δ 7.30 (m, 5H), 6.38 (br s, 1H), 6.29 (s, 1H), 4.43 (d, J=6 Hz, 2H), 4.11 (t, J=6 Hz, 1H), 3.42 (d, J=9 Hz, 2H), 1.47 (s, 9H).

Example 5

Synthesis of (6S,9aS)—N-benzyl-6-(4-hydroxybenzyl)-4,7-dioxo-2-(prop-2-ynyl)-8-(quinolin-5-ylmethyl)octahydro-1H-pyrazino[2,1-c][1,2,4]triazine-1-carboxamide (4)

Compound 4 was prepared according to the procedures set forth in steps 1-4 of Scheme 4 below.

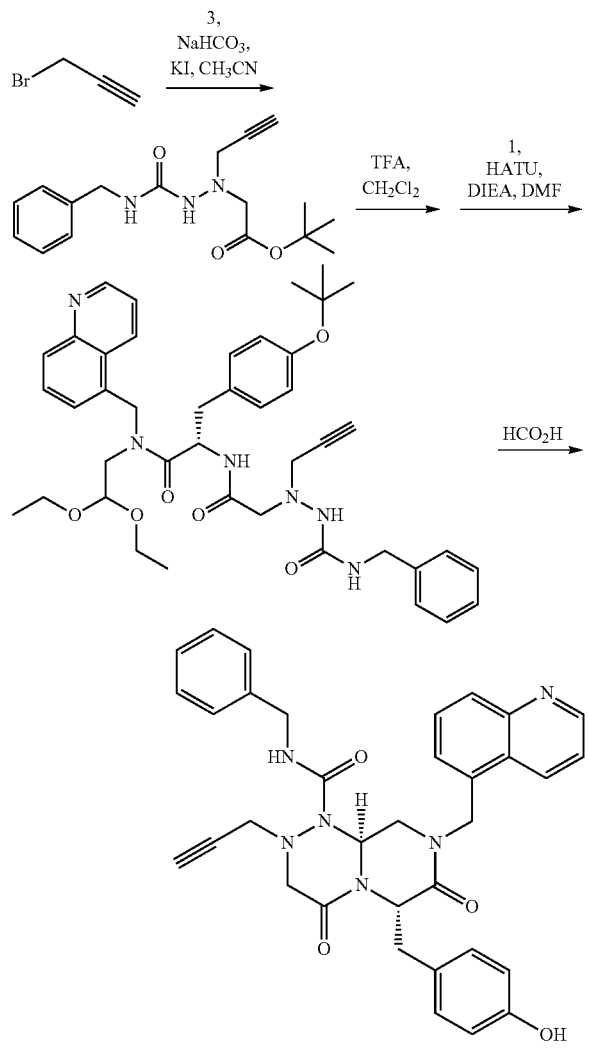

Step 1: tert-butyl 2-(2-(benzylcarbamoyl)-1-(prop-2-ynyl)hydrazinyl)acetate

A mixture of tert-butyl 2-(2-(benzylcarbamoyl)hydrazinyl)acetate (1.0 g, 3.58 mmol), propargyl bromide (0.7 mL, @ 9.2 M in toluene), NaHCO$_3$ (0.6 g, 7.14 mmol) and KI (60 mg) in dry CH$_3$CN (30 mL) was stirred at 75° C. for 3 days in a sealed tube. The reaction mixture was cooled to room temperature and filtered. The filtrates were evaporated and purified by silica gel chromatography using 50% EtOAc/hexane afforded the title compound (0.63 g) as a colorless oil. MS (ESI): m/z 318.0 (M+H)$^+$; analytical HPLC: 17.0 min.

Step 2-3: (S)—N-benzyl-2-(2-(3-(4-tert-butoxyphenyl)-1-((2,2-diethoxyethyl)(quinolin-5-ylmethyl)amino)-1-oxopropan-2-ylamino)-2-oxoethyl)-2-(prop-2-ynyl)hydrazinecarboxamide tert-butyl 2-(2-(benzylcarbamoyl)-1-(prop-2-ynyl)hydrazinyl)acetate (0.31 g, 0.98 mmol) was treated in CH$_2$Cl$_2$ (10 mL) and TFA (10 mL) at room temperature under argon over 2 hours. Evaporation and co-evaporation with CHCl$_3$ twice to dryness gave 2-(2-(benzylcarbamoyl)-1-(prop-2-ynyl)hydrazinyl)acetic acid (TFA salt) as a yellow oil, which was used in the next step without further purification. MS (ESI): m/z 261.9 (M+H)$^+$; analytical HPLC: 12.1 min.

To a solution of (S)-2-amino-3-(4-tert-butoxyphenyl)-N-(2,2-diethoxyethyl)-N-(quinolin-5-ylmethyl)propanamide (0.48 g, 0.98 mmol) in DMF (7 mL) was added DIEA (0.51 mL, 2.93 mmol) and 2-(2-(benzylcarbamoyl)-1-(prop-2-ynyl)hydrazinyl)acetic acid (TFA salt) prepared above. After cooled to 0° C., HATU (0.37 g, 0.98 mmol) was added. The reaction mixture was stirred under argon at 0° C. for 0.5 hour and at room temperature overnight, and then taken into ethyl acetate (50 mL) and water (50 mL). The aqueous layer was extracted with ethyl acetate (25 mL×2), and the combined organic extracts were washed with brine (25 mL), dried (Na$_2$SO$_4$) and evaporated. Purification by silica-gel chromatography using 5% MeOH/CH$_2$Cl$_2$ gave the desired product (0.79 g) as a faint-yellow foam. MS (ESI): m/z 737.4 (M+H)$^+$; analytical HPLC: 16.1 min.

Step 4: (6S,9aS)—N-benzyl-6-(4-hydroxybenzyl)-4,7-dioxo-2-(prop-2-ynyl)-8-(quinolin-5-ylmethyl)octahydro-1H-pyrazino[2,1-c][1,2,4]triazine-1-carboxamide A solution of (S)—N-benzyl-2-(2-(3-(4-tert-butoxyphenyl)-1-((2,2-diethoxyethyl)(quinolin-5-ylmethyl)amino)-1-oxopropan-2-ylamino)-2-oxoethyl)-2-(prop-2-ynyl)hydrazinecarboxamide (0.79 g, 1.07 mmol) in formic acid (25 mL) was stirred at room temperature over 20 hours. The solvent was removed, and the resulting residues were taken into EtOAc (25 mL) and sat'd NaHCO$_3$ (25 mL). The aqueous layers were further extracted with EtOAc (25 mL×1). The combined organic extracts were dried (MgSO$_4$) and evaporated. The crude material was purified by silica-gel chromatography using EtOAc to give the desired product (0.36 g) as a faint-yellow foam. MS (ESI): m/z 589.2 (M+H)$^+$; analytical HPLC: 12.5 min.

Example 6

Synthesis of (6S,9aS)—N-benzyl-6-(4-hydroxybenzyl)-4,7-dioxo-2-((3-phenylisoxazol-5-yl)methyl)-8-(quinolin-5-ylmethyl)octahydro-1H-pyrazino[2,1-c][1,2,4]triazine-1-carboxamide (5)

Compound 5 was prepared according to the procedures set forth in steps 1-6 of Scheme 5 below.

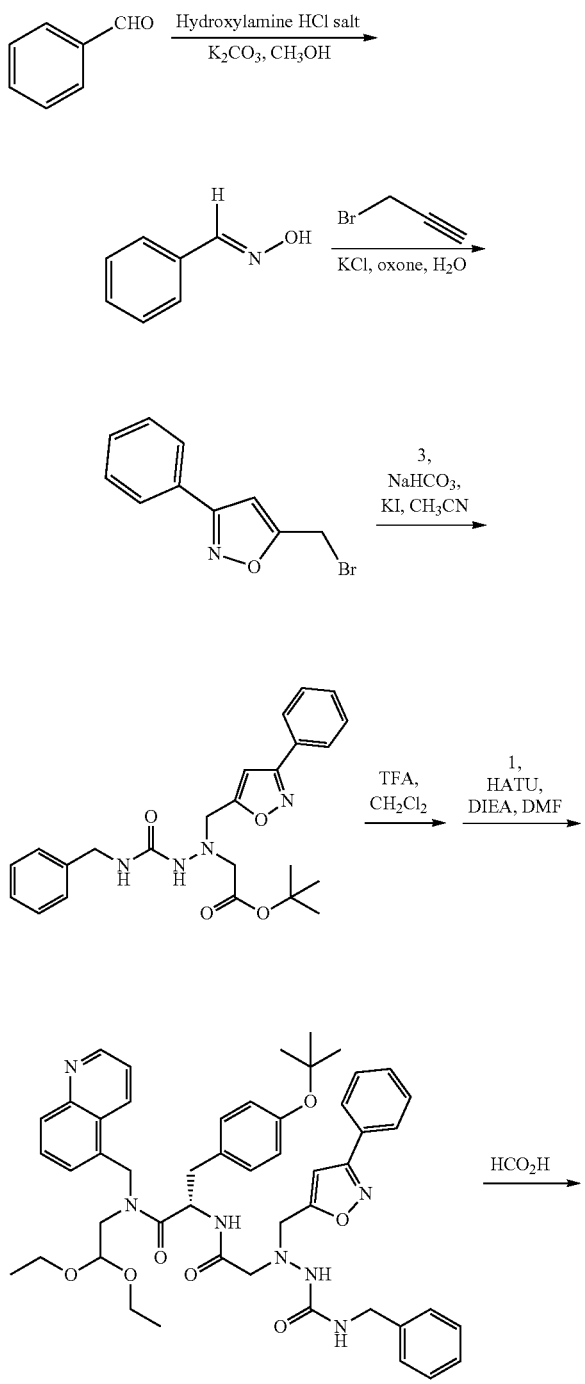

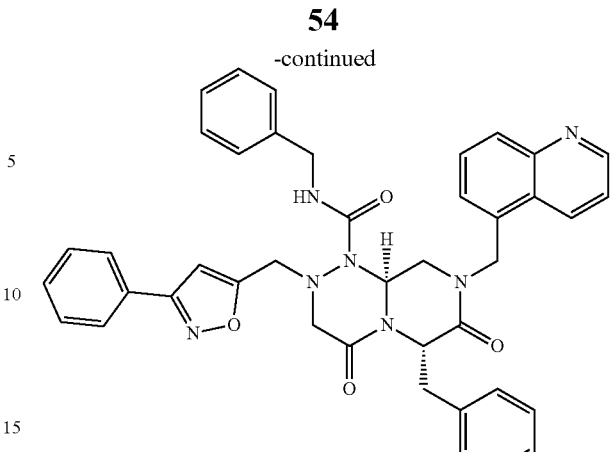

Step 1-2: 5-(bromomethyl)-3-phenylisoxazole

To a solution of benzaldehyde (2.0 g, 18.8 mmol) in MeOH (18 mL) was added hydroxylamine hydrochloride (1.6 g, 22.6 mmol) and $K_2CO_3$ (3.1 g, 22.6 mmol). The reaction mixture was stirred at room temperature overnight, diluted with water (50 mL) and extracted with EtOAc (50 mL×1, 25 mL×2). The organic extracts were dried ($Na_2SO_4$) and evaporated to dryness. Benzaldehyde oxime obtained (2.4 g) as a colorless liquid was used in the next step without further purification.

To a mixture of benzaldehyde oxime (2.4 g, 19.4 mmol) in water (60 mL) at room temperature was added KCl (1.5 g, 20.1 mmol) and propargyl bromide (5.6 mL, @ 9.2 M in toluene). The resulting mixture was cooled to 0° C., and oxone (9.2 g, 15 mmol) was added in small portions. The reaction mixture was stirred at 0° C. for 1 h and at room temperature overnight, extracted with EtOAc (50 mL×2). The organic extracts were washed with sat'd NaCl (25 mL), dried ($MgSO_4$) and evaporated to dryness. The title compound (4.2 g) as a faint-yellow solid was obtained and used in the next step without further purification. $^1$H-NMR (300 MHz, $CDCl_3$) δ 7.80 (m, 2H), 7.47 (m, 3H), 6.63 (s, 1H), 4.52 (s, 2H).

Step 3: tert-butyl 2-(2-(benzylcarbamoyl)-1-((3-phenylisoxazol-5-yl)methyl)hydrazinyl)acetate A mixture of 5-(bromomethyl)-3-phenylisoxazole (56 mg, 0.24 mmol), tert-butyl 2-(2-(benzylcarbamoyl)hydrazinyl)acetate (60 mg, 0.22 mmol), $NaHCO_3$ (36 mg, 0.43 mmol) and KI (3.7 mg) in dry $CH_3CN$ (1.5 mL) was stirred at 65° C. for 20 h. The reaction mixture was cooled to room temperature and filtered. The filtrates were evaporated and the resulting residues were purified by silica gel chromatography using EtOAc/hexane (ratio: 1:1 to 2:1) afforded the title compound (61 mg) as a white solid. MS (ESI): m/z 437.2 (M+H)$^+$.

Step 4: 2-(2-(benzylcarbamoyl)-1-((3-phenylisoxazol-5-yl)methyl)hydrazinyl)acetic acid The tert-butyl 2-(2-(benzylcarbamoyl)-1-((3-phenylisoxazol-5-yl)methyl)hydrazinyl)acetate (61 mg, 0.14 mmol) was treated in $CH_2Cl_2$ (1.5 mL) and TFA (1.5 mL) at room temperature under argon over 3 hours. Evaporation and co-evaporation with $CHCl_2$ twice to dryness gave the title compound (TFA salt) as an off-white solid, which was used in the next step without further purification. $^1$H-NMR (300 MHz, DMSO-de) δ 7.82 (m, 2H), 7.53 (m, 3H), 7.37 (s, 1H), 7.13 (s, 5H), 7.05 (s, 1H), 6.94 (t, J=6 Hz, 1H), 4.20 (s, 2H), 4.17 (d, J=6 Hz, 2H), 3.67 (s, 2H).

Step 5: (S)—N-benzyl-2-(2-(3-(4-tert-butoxyphenyl)-1-((2,2-diethoxyethyl)(quinolin-5-ylmethyl)amino)-1-oxopropan-2-ylamino)-2-oxoethyl)-2-((3-phenylisoxazol-5-yl)methyl)hydrazinecarboxamide To a solution of (S)-2-amino-3-(4-tert-butoxyphenyl)-N-(2,2-diethoxyethyl)-N-(quinolin-5-ylmethyl)propanamide (69 mg, 0.14 mmol) in DMF (1 mL) was added DIEA (73 μL, 0.42 mmol) and 2-(2-(benzylcarbamoyl)-1-((3-phenylisoxazol-5-yl)methyl)hydrazinyl)acetic acid (TFA salt; prepared in step 4). After cooled to 0° C., HATU (53 mg, 0.14 mmol) was added. The reaction mixture was stirred under argon at 0° C. for 0.5 hour and at room temperature overnight, and then taken into ethyl acetate (10 mL) and water (10 mL). The aqueous layer was extracted with ethyl acetate (10 mL×2), and the combined organic extracts were washed with brine (10 mL), dried (Na$_2$SO$_4$) and evaporated. Purification by silica-gel chromatography using MeOH/CH$_2$Cl$_2$ (5% and 10%) gave the desired product (104 mg) as a white foam. MS (ESI): m/z 856.7 (M+H)$^+$; analytical HPLC: 18.0 min.

Step 6: (6S,9aS)—N-benzyl-6-(4-hydroxybenzyl)-4,7-dioxo-2-((3-phenylisoxazol-5-yl)methyl)-8-(quinolin-5-ylmethyl)octahydro-1H-pyrazino[2,1-c][1,2,4]triazine-1-carboxamide A solution of (S)—N-benzyl-2-(2-(3-(4-tert-butoxyphenyl)-1-((2,2-diethoxyethyl)(quinolin-5-ylmethyl)amino)-1-oxopropan-2-ylamino)-2-oxoethyl)-2-((3-phenylisoxazol-5-yl)methyl)hydrazinecarboxamide (100 mg) in formic acid (5 mL) was stirred at room temperature over 20 hours. Evaporation to dryness, purification by silica-gel chromatography (CH$_2$Cl$_2$/CH$_3$OH/NH$_4$OH: 270:9:1 and 180:9:1) and lyophilization gave the desired product (67 mg) as a white solid. MS (ESI): m/z 708.3 (M+H)$^+$; analytical HPLC: 14.9 min (>99% pure).

Example 7

Synthesis of (6S,9aS)—N-benzyl-6-(4-hydroxybenzyl)-2-((3-(6-morpholinopyridin-2-yl)isoxazol-5-yl)methyl)-4,7-dioxo-8-(quinolin-5-ylmethyl)octahydro-1H-pyrazino[2,1-c][1,2,4]triazine-1-carboxamide (6)

Compound 6 was prepared according to the procedures set forth in steps 1-9 of Scheme 6 below.

Scheme 6

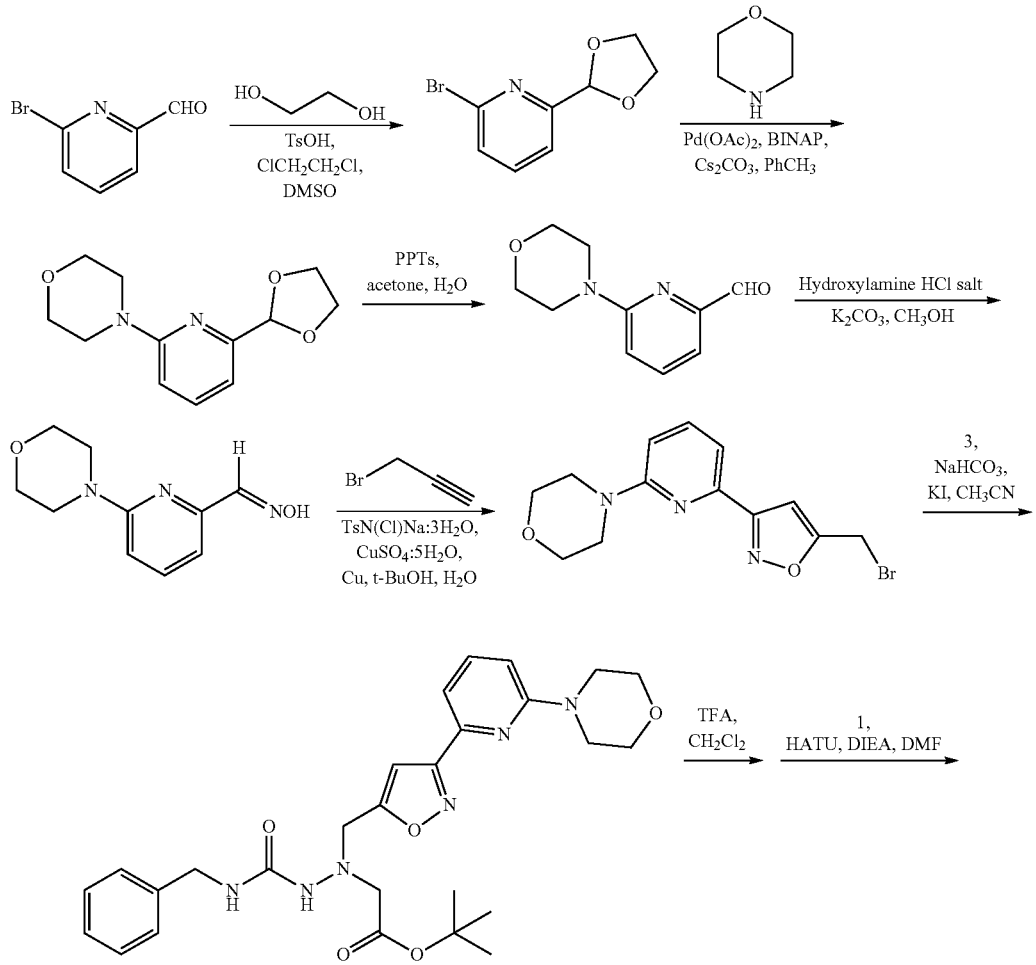

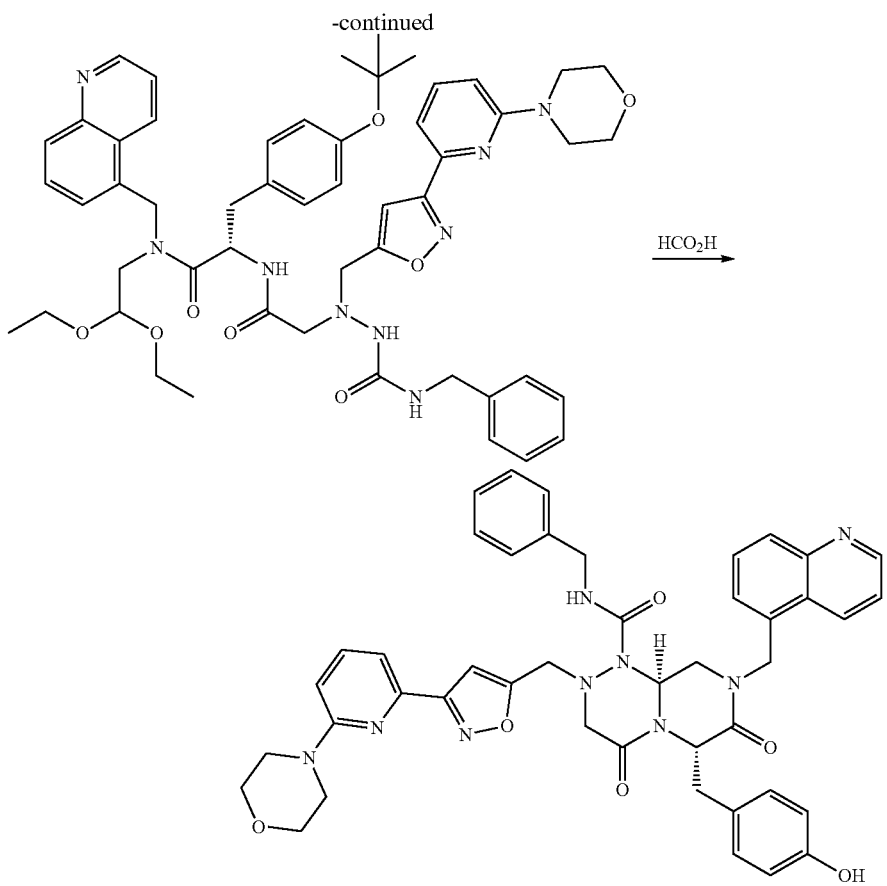

Step 1: 2-bromo-6-(1,3-dioxolan-2-yl)pyridine

The reaction mixture of 6-bromopicolinaldehyde (0.4 g, 2.15 mmol), ethylene glycol (0.62 mL, 11.1 mmol), p-toluenesulfonic acid monohydrate (0.46 g, 2.67 mmol) in 1,2-dichloroethane (14.4 mL) and DMSO (0.32 mL) was stirred at 95° C. under argon overnight and evaporated to dryness after cooled to room temperature. The resulting residues were diluted with EtOAc (25 mL) and washed with 0.5 N NaOH (20 mL), sat'd NaCl (15 mL), dried ($Na_2SO_4$) and evaporated. The crude material was purified by silica-gel chromatography (25% EtOAc/hexane) to give the desired product (0.32 g) as a colorless oil. $^1$H-NMR (300 MHz, $CDCl_3$) δ 7.61 (t, J=4 Hz, 1H), 7.51 (m, 2H), 5.83 (s, 1H), 4.21-4.07 (m, 4H).

Step 2: 4-(6-(1,3-dioxolan-2-yl)pyridin-2-yl)morpholine

A mixture of 2-bromo-6-(1,3-dioxolan-2-yl)pyridine (0.32 g, 1.38 mmol), morpholine (0.14 mL, 1.65 mmol), $Pd(OAc)_2$ (40 mg), BINAP (104 mg), $Cs_2CO_3$ (0.62 g) in toluene (14 mL) was purged with argon for 2 minutes, and then stirred at 100° C. over 22 hours in a sealed tube. The reaction mixture was filtered via Celite and evaporated. Purification by silica-gel chromatography with 25% and 50% EtOAc/hexane gave the title compound (0.26 g) as a brown solid. $^1$H-NMR (300 MHz, $CDCl_3$) δ 7.53 (t, J=4 Hz, 1H), 6.88 (d, J=4 Hz, 1H), 6.61 (d, J=6 Hz, 1H), 5.72 (s, 1H), 4.19-4.05 (m, 4H), 3.81 (t, J=4 Hz, 4H), 3.52 (t, H=4 Hz, 4H).

Step 3: 6-morpholinopicolinaldehyde

To a suspension of 4-(6-(1,3-dioxolan-2-yl)pyridin-2-yl)morpholine (0.26 g, 1.10 mmol) in acetone (7 mL) and water (7 mL) was added pyridinium tosylate (83 mg). The reaction mixture was refluxed overnight and concentrated in vacuo. EtOAc (30 mL) was added, and the mixture was washed with sat'd $NaHCO_3$ (15 mL), sat'd NaCl (15 mL) and dried ($Na_2SO_4$). Evaporation and purification by silica-gel chromatography (25% EtOAc/hexane) gave the desired product (0.19 g) as a faint-yellow solid. $^1$H-NMR (300 MHz, $CDCl_3$) δ 10.1 (s, 1H), 7.71 (t, J=9, and 4 Hz, 1H), 7.37 (d, J=9 Hz, 1H), 6.93 (d, J=6 Hz, 1H), 3.89 (t, J=4.5 Hz, 4H), 3.68 (t, H=4.5 Hz, 4H).

Step 4: 6-morpholinopicolinaldehyde oxime

To a solution of 6-morpholinopicolinaldehyde (0.19 g, 0.99 mmol) in MeOH (18 mL) was added hydroxylamine hydrochloride (81 mg, 1.17 mmol) and $K_2CO_3$ (0.16 g, 1.16 mmol). The reaction mixture was stirred at room temperature overnight, diluted with water (15 mL) and extracted with EtOAc (10 mL×3). The organic extracts were dried ($Na_2SO_4$) and evaporated to dryness. Purification by silica-gel chromatography (30% EtOAc/hexane) gave the desired product (0.18 g) as a white solid. $^1$H-NMR (300 MHz, DMSO-$d_6$) δ 11.5 (s, 1H), 7.90 (s, 1H), 7.58 (d, J=9, and 4 Hz, 1H), 7.08 (d, J=6 Hz, 1H), 6.81 (d, J=6 Hz, 1H), 3.70 (t, J=4.5 Hz, 4H), 3.46 (t, H=4.5 Hz, 4H).

Step 5: 4-(6-(5-(bromomethyl)isoxazol-3-yl)pyridin-2-yl)morpholine

To a suspension of 6-morpholinopicolinaldehyde oxime (62 mg, 0.30 mmol) in 50% t-BuOH/water (2 mL) was added chloramine-T trihydrate (88.5 mg, 0.31 mmol), Copper(II) sulfate pentahydrate (3 mg), copper turnings (1 mg), and followed by addition of propargyl bromide (35.9 µL, @ 9.2 M in toluene). The reaction mixture was stirred at room temperature overnight, and taken into EtOAc (10 mL) and water (10 mL). The aqueous layers were extracted with EtOAc (10 mL×2). The combined organic extracts were washed with sat'd NaCl (10 mL) and dried (Na$_2$SO$_4$). Evaporation and purification by silica-gel chromatography (25% EtOAc/hexane) gave the title compound (34 mg) as a white solid. MS (ESI): m/z 324.0, 326.0 (M+H)$^+$; analytical HPLC: 17.8 min.

Step 6-9: (6S,9aS)—N-benzyl-6-(4-hydroxybenzyl)-2-((3-(6-morpholinopyridin-2-yl)isoxazol-5-yl)methyl)-4,7-dioxo-8-(quinolin-5-ylmethyl)octahydro-1H-pyrazino[2,1-c][1,2,4]triazine-1-carboxamide The title compound 6 was obtained, according to the procedures described in steps 3-6 of Example 6. MS (ESI): m/z 794.4 (M+H)$^+$; analytical HPLC: 14.1 min (>99% pure).

Example 8

Synthesis of (6S,9aS)—N-benzyl-2-((3-(5-fluoropyridin-2-yl)isoxazol-5-yl)methyl)-6-(4-hydroxybenzyl)-4,7-dioxo-8-(quinolin-5-ylmethyl)octahydro-1H-pyrazino[2,1-c][1,2,4]triazine-1-carboxamide methanesulfonate (7)

Compound 7 was prepared according to the procedures set forth in steps 1-5 of Scheme 7 below.

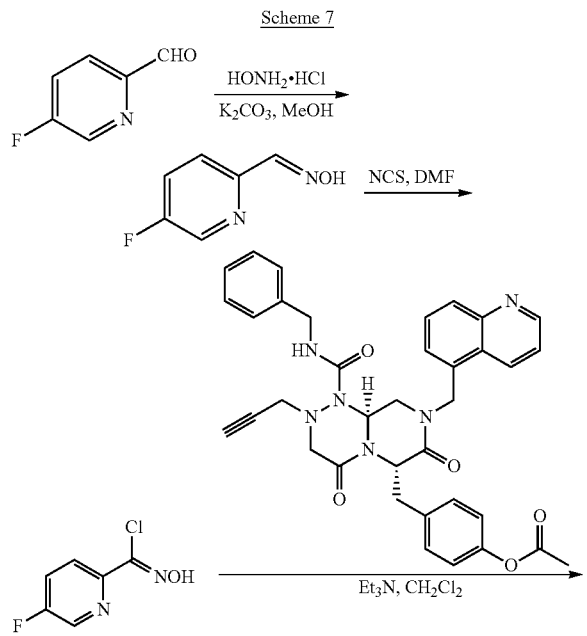

Scheme 7

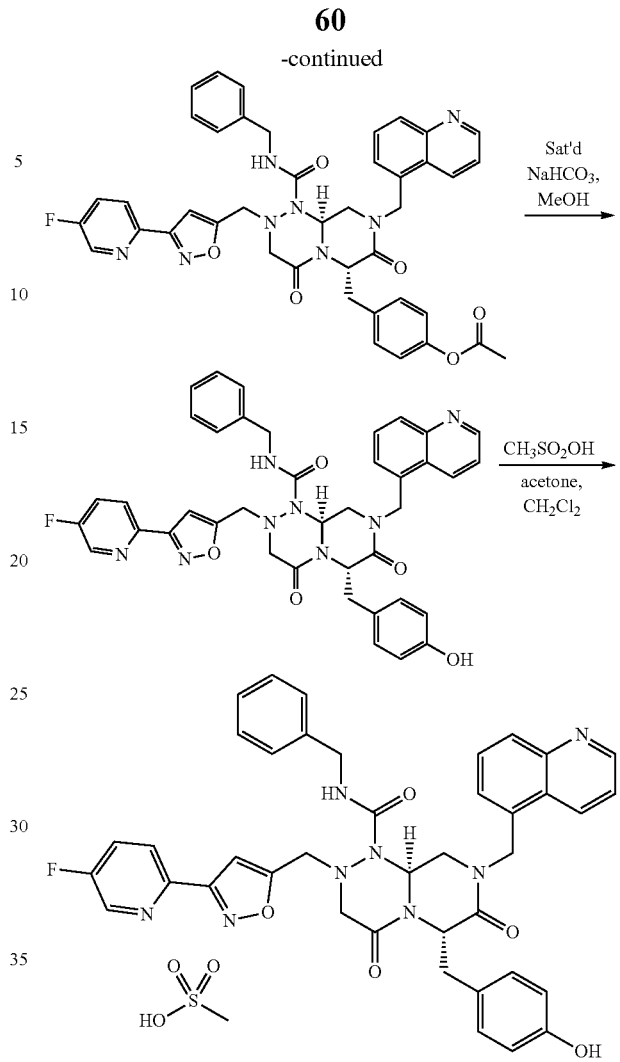

Step 1: 5-fluoropicolinaldehyde oxime

To a solution of 5-fluoropicolinaldehyde (0.5 g, 4.0 mmol) in MeOH (4 mL) was added hydroxylamine hydrochloride (0.33 g, 4.8 mmol) and K$_2$CO$_3$ (0.67 g, 4.8 mmol). The reaction mixture was stirred at room temperature overnight, diluted with water (10 mL) and extracted with EtOAc (10 mL×3). The organic extracts were dried (Na$_2$SO$_4$) and evaporated to dryness. The title compound (0.52 g) as a white solid was used in the next step without further purification. $^1$H-NMR (300 MHz, DMSO-d$_6$) δ 11.7 (s, 1H), 8.59 (d, J=3 Hz, 1H), 8.09 (s, 1H), 7.87 (m, 1H), 7.77 (m, 1H).

Step 2: 5-fluoro-N-hydroxypicolinimidoyl chloride

To a solution of 5-fluoropicolinaldehyde oxime (0.4 g, 2.85 mmol) in DMF (3 mL) was added N-chlorosuccinimide (0.42 g, 3.14 mmol). The reaction mixture was stirred under argon at 50° C. overnight, cooled to room temperature and poured into Et$_2$O (15 mL) and water (15 mL). The aqueous layers were extracted with Et$_2$O (15 mL×2). The organic extracts were washed with water (10 mL), sat'd NH$_4$Cl (10 mL) and sat'd NaCl (10 mL), dried (Na$_2$SO$_4$) and evaporated to dryness. The title compound (0.49 g) as a white solid was used in the next step without further purification.

$^1$H-NMR (300 MHz, DMSO-d$_6$) δ 12.7 (s, 1H), 8.68 (d, J=2.8 Hz, 1H), 7.96 (m, 1H), 7.84 (m, 1H).

Step 3: 4-(((6S,9aS)-1-(benzylcarbamoyl)-2-((3-(5-fluoropyridin-2-yl)isoxazol-5-yl)methyl)-4,7-dioxo-8-(quinolin-5-ylmethyl)octahydro-1H-pyrazino[2,1-c][1,2,4]triazin-6-yl)methyl)phenyl acetate To a solution of 4-(((6S,9aS)-1-(benzylcarbamoyl)-4,7-dioxo-2-(prop-2-ynyl)-8-(quinolin-5-ylmethyl)octahydro-1H-pyrazino[2,1-c][1,2,4]triazin-6-yl)methyl)phenyl acetate (0.60 g, 0.95 mmol; prepared according to the procedure disclosed in Example 11, using acetyl chloride instead) in dry CH$_2$Cl$_2$ (27 mL) at 0° C. was added 5-fluoro-N-hydroxypicolinimidoyl chloride (0.16 g, 0.90 mmol), followed by dropwise addition of Et$_3$N (0.25 mL, 1.80 mmol) in CH$_2$Cl$_2$ (1 mL). The reaction mixture was stirred under argon at 0° C. for 1 hour and at room temperature over 24 hours. Evaporation to dryness and purification by silica-gel chromatography with CH$_3$OH/CH$_2$Cl$_2$ yielded a partially purified title compound (0.54 g) as an oily residue. MS (ESI): m/z 769.3 (M+H)$^+$; analytical HPLC: 14.9 min.

Step 4: (6S,9aS)—N-benzyl-2-((3-(5-fluoropyridin-2-yl)isoxazol-5-yl)methyl)-6-(4-hydroxybenzyl)-4,7-dioxo-8-(quinolin-5-ylmethyl)octahydro-1H-pyrazino[2,1-c][1,2,4]triazine-1-carboxamide To a solution of 4-(((6S,9aS)-1-(benzylcarbamoyl)-2-((3-(5-fluoropyridin-2-yl)isoxazol-5-yl)methyl)-4,7-dioxo-8-(quinolin-5-ylmethyl)octahydro-1H-pyrazino[2,1-c][1,2,4]triazin-6-yl)methyl)phenyl acetate (0.54 g; prepared as shown in step 3 above) in CH$_3$OH (16 mL) was added dropwise sat'd NaHCO$_3$ (5.3 mL). The reaction mixture was stirred at room temperature for 3 hours, evaporated in vacuo and taken into EtOAc (15 mL) and water (15 mL). The aqueous layers were extracted with EtOAc (15 mL×2). The organic extracts were washed with sat'd NaCl (15 mL), dried (Na$_2$SO$_4$) and evaporated to dryness. Purification by silica-gel chromatography with EtOAc/CH$_2$Cl$_2$ gave the title compound (0.26 g) as a white solid. MS (ESI): m/z 727.3 (M+H)$^+$; analytical HPLC: 13.8 min (>96% pure).

Step 5: (6S,9aS)—N-benzyl-2-((3-(5-fluoropyridin-2-yl)isoxazol-5-yl)methyl)-6-(4-hydroxybenzyl)-4,7-dioxo-8-(quinolin-5-ylmethyl)octahydro-1H-pyrazino[2,1-c][1,2,4]triazine-1-carboxamide methanesulfonate To a solution (6S,9aS)—N-benzyl-2-((3-(5-fluoropyridin-2-yl)isoxazol-5-yl)methyl)-6-(4-hydroxybenzyl)-4,7-dioxo-8-(quinolin-5-ylmethyl)octahydro-1H-pyrazino[2,1-c][1,2,4]triazine-1-carboxamide (176 mg, 0.24 mmol) in CH$_2$Cl$_2$ (6 mL) was added slowly a solution of methanesulfonic acid (23.3 mg, 0.24 mmol) in acetone and CH$_2$Cl$_2$. After stirring at room temperature for a few minutes, hexane (ca. 10 mL) was added slowly.

The white precipitate formed was collected via filtration and washed with hexane and EtOAc. Air dry and lyophilization with Milli-Q water gave the desired product (173 mg) as a pale-yellow solid. MS (ESI): m/z 727.2 (M+H)$^+$; analytical HPLC: 13.8 min (>97% pure).

Example 9

Synthesis of (6S,9aS)—N-benzyl-6-(4-hydroxybenzyl)-4,7-dioxo-2-((3-(pyrazin-2-yl)isoxazol-5-yl)methyl)-8-(quinolin-5-ylmethyl)octahydro-1H-pyrazino[2,1-c][1,2,4]triazine-1-carboxamide (8)

Compound 8 was prepared according to the procedures set forth in steps 1-2 of Scheme 8 below.

Scheme 8

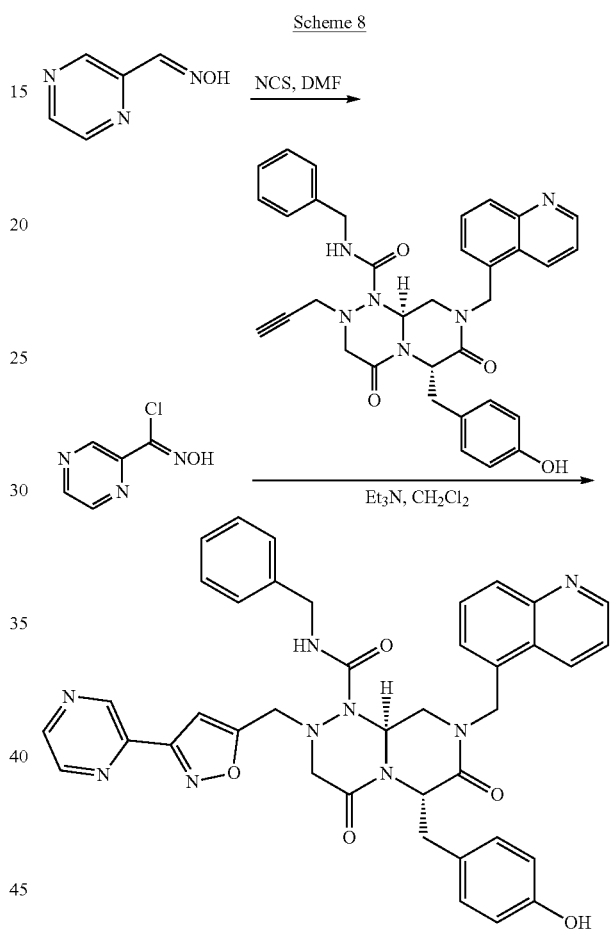

Step 1: N-hydroxypyrazine-2-carbimidoyl chloride

The title compound as a pale-yellow solid was obtained, according to the procedure described in step 2 of Example 8. $^1$H-NMR (300 MHz, DMSO-d$_6$) δ 9.10 (s, 1H), 8.77-8.73 (m, 3H).

Step 2: (6S,9aS)—N-benzyl-6-(4-hydroxybenzyl)-4,7-dioxo-2-((3-(pyrazin-2-yl)isoxazol-5-yl)methyl)-8-(quinolin-5-ylmethyl)octahydro-1H-pyrazino[2,1-c][1,2,4]triazine-1-carboxamide To a solution of 4-(((6S,9aS)-1-(benzylcarbamoyl)-4,7-dioxo-2-(prop-2-ynyl)-8-(quinolin-5-ylmethyl)octahydro-1H-pyrazino[2,1-c][1,2,4]triazin-6-yl)methyl)phenyl acetate (0.30 g, 0.51 mmol) in dry CH$_2$Cl$_2$ (15 mL) at 0° C. was added N-hydroxypyrazine-2-carbimidoyl chloride (76.1 mg, 0.48 mmol), followed by dropwise addition of Et$_3$N (134 μL, 0.97 mmol). The reaction mixture was stirred under argon at 0° C. for 1 hour and at room temperature over 20 hours. Evaporation to dryness, purification by silica-gel chromatography with CH₃OH/EtOAc and lyophilization in CH₃CN and Milli-Q water gave the title compound (0.12 g) as a white solid. MS (ESI): m/z 710.3 (M+H)⁺; analytical HPLC: 12.6 min (>95% pure).

Example 10

Synthesis of (6S,9aS)—N-benzyl-6-(4-hydroxybenzyl)-4,7-dioxo-2-((3-(pyrrolidin-2-yl)isoxazol-5-yl)methyl)-8-(quinolin-5-ylmethyl)octahydro-1H-pyrazino[2,1-c][1,2,4]triazine-1-carboxamide (9)

Compound 9 was prepared according to the procedures set forth in steps 1-4 of Scheme 9 below.

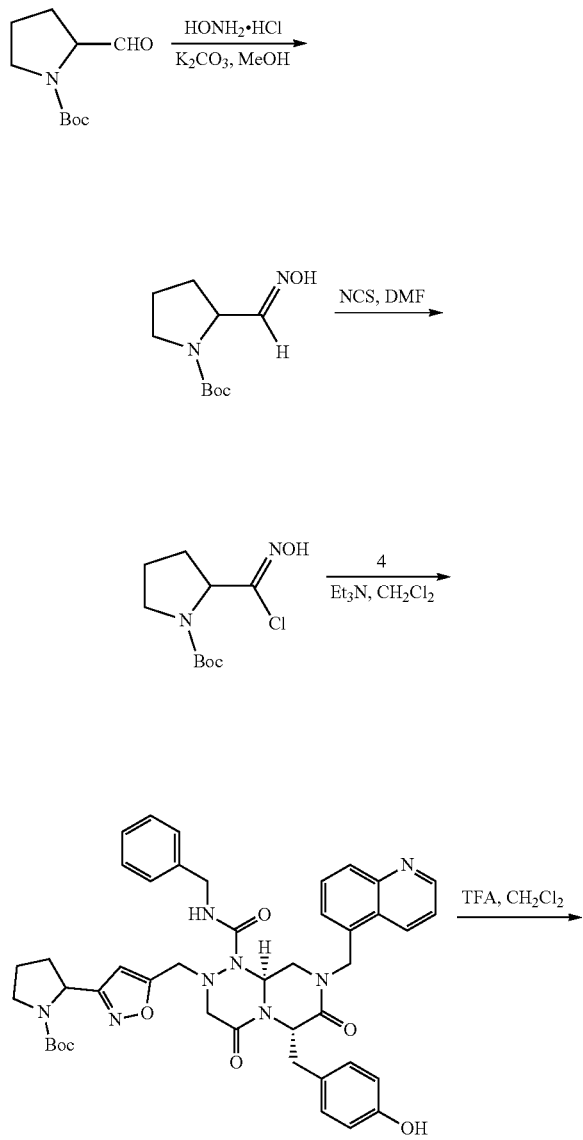

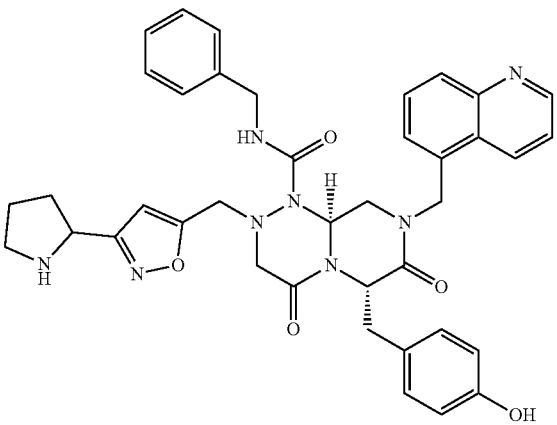

Step 1-2: tert-butyl 2-(chloro(hydroxyimino)methyl)pyrrolidine-1-carboxylate

The title compound was obtained, according to the procedures described in steps 1-2 of Example 8. analytical HPLC: 15.4 min (>97% pure).

Step 3: tert-butyl 2-(5-(((6S,9aS)-1-(benzylcarbamoyl)-6-(4-hydroxybenzyl)-4,7-dioxo-8-(quinolin-5-ylmethyl)dihydro-1H-pyrazino[2,1-c][1,2,4]triazin-2(6H,7H,8H,9H,9aH)-yl)methyl)isoxazol-3-yl)pyrrolidine-1-carboxylate To a solution of (6S,9aS)—N-benzyl-6-(4-hydroxybenzyl)-4,7-dioxo-2-(prop-2-ynyl)-8-(quinolin-5-ylmethyl)octahydro-1H-pyrazino[2,1-c][1,2,4]triazine-1-carboxamide (70 mg, 0.12 mmol) in dry CH₂Cl₂ (5 mL) was added tert-butyl 2-(chloro(hydroxyimino)methyl)pyrrolidine-1-carboxylate (118 mg, 0.48 mmol), followed by dropwise addition of Et₃N (0.13 mL, 0.93 mmol). The reaction mixture was stirred under argon at 40° C. for 2 days. Evaporation to dryness and purification by silica-gel chromatography with EtOAc gave the title compound (26 mg) as a white residue. MS (ESI): m/z 801.5 (M+H)⁺; analytical HPLC: 14.7 min (94% pure).

Step 4: (6S,9aS)—N-benzyl-6-(4-hydroxybenzyl)-4,7-dioxo-2-((3-(pyrrolidin-2-yl)isoxazol-5-yl)methyl)-8-(quinolin-5-ylmethyl)octahydro-1H-pyrazino[2,1-c][1,2,4]triazine-1-carboxamide tert-butyl 2-(5-(((6S,9aS)-1-(benzylcarbamoyl)-6-(4-hydroxybenzyl)-4,7-dioxo-8-(quinolin-5-ylmethyl)dihydro-1H-pyrazino[2,1-c][1,2,4]triazin-2(6H,7H,8H,9H,9aH)-yl)methyl)isoxazol-3-yl)pyrrolidine-1-carboxylate (26 mg, 0.032 mmol) was stirred in CH₂Cl₂ (1 mL) and TFA (1 mL) at room temperature under argon over 2 hours. Evaporation and co-evaporation with CHCl₃ twice to dryness, purification by silica-gel chromatography (CH₂Cl₂/CH₃OH/NH₄OH: 180:9:1 and 90:9:1) and followed by lyophilization with CH₃CN and Milli-Q water gave the desired product (14 mg) as a white powder. MS (ESI): m/z 701.3 (M+H)⁺; analytical HPLC: 10.6 min (>99% pure).

Example 11

Synthesis of 4-((((6S,9aS)-1-(benzylcarbamoyl)-2-((3-(4-fluorophenyl)isoxazol-5-yl)methyl)-4,7-dioxo-8-(quinolin-5-ylmethyl)octahydro-1H-pyrazino[2,1-c][1,2,4]triazin-6-yl)methyl)phenyl dodecanoate (10)

Compound 10 was prepared according to Scheme 10 using the procedure disclosed below.

Scheme 10

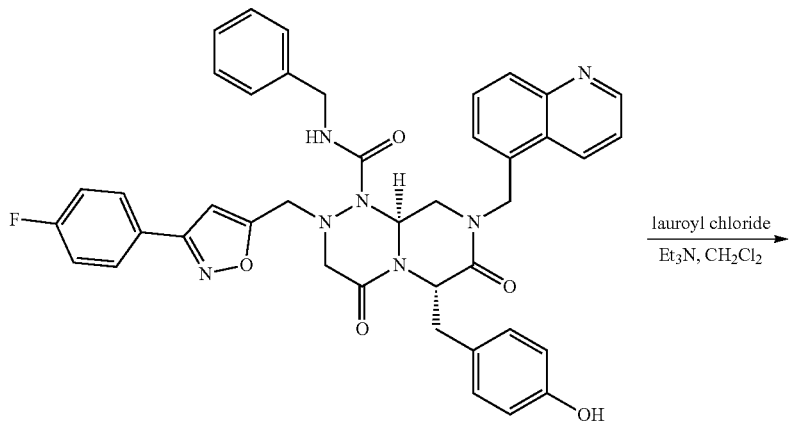

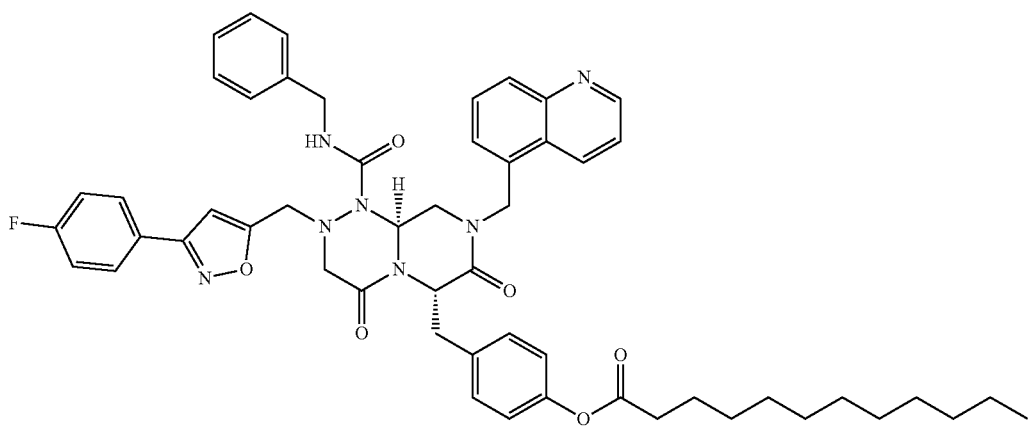

To a solution of (6S,9aS)—N-benzyl-2-((3-(4-fluorophenyl)isoxazol-5-yl)methyl)-6-(4-hydroxybenzyl)-4,7-dioxo-8-(quinolin-5-ylmethyl)octahydro-1H-pyrazino[2,1-c][1,2,4]triazine-1-carboxamide (1.2 g, 1.67 mmol) in dry $CH_2Cl_2$ (47 mL) at 0° C. was added $Et_3N$ (0.47 mL, 3.34 mmol), followed by slow addition of lauroyl chloride (0.58 mL, 2.51 mmol). The reaction mixture was stirred under argon at 0° C. for 1 hour and at room temperature overnight, and evaporated to dryness. The resulting residues were taken into EtOAc (100 mL) and sat'd $NaHCO_3$ (50 mL), and the organic layers were washed with sat'd NaCl (50 mL) and dried ($MgSO_4$). Evaporation, purification by silica-gel chromatography using EtOAc/$CH_2Cl_2$ and lyophilization gave the title product (1.1 g) as a white foam. MS (ESI): m/z 908.7 $(M+H)^+$.

Example 12

Synthesis of ethyl 2-(2-((4-((((6S,9aS)-1-(benzylcarbamoyl)-4,7-dioxo-2-((3-(pyridin-2-yl)isoxazol-5-yl)methyl)-8-(quinolin-5-ylmethyl)octahydro-1H-pyrazino[2,1-c][1,2,4]triazin-6-yl)methyl)phenoxy)carbonylamino)acetamido)acetate (11)

Compound 11 was prepared according to Scheme 11 using the procedures disclosed below.

mixture was stirred at room temperature under argon overnight and filtered. The filtrate was diluted with $CH_2Cl_2$ (25 mL) and washed with water (25 mL) and 10% $KHSO_4$ (25 mL), dried ($MgSO_4$) and evaporated. The crude material was purified by silica-gel chromatography using EtOAc/hexane to yield the title product (0.53 g) as a white oily residue. $^1$H-NMR (300 MHz, DMSO-$d_6$) δ 8.17 (t, J=6 Hz, 1H), 7.0 (t, J=6 Hz, 1H), 4.09 (q, J=6 Hz, 2H), 3.82 (d, J=6 Hz, 2H), 3.56 (d, J=6 Hz, 2H), 1.38 (s, 9H), 1.16 (t, J=6 Hz, 3H).

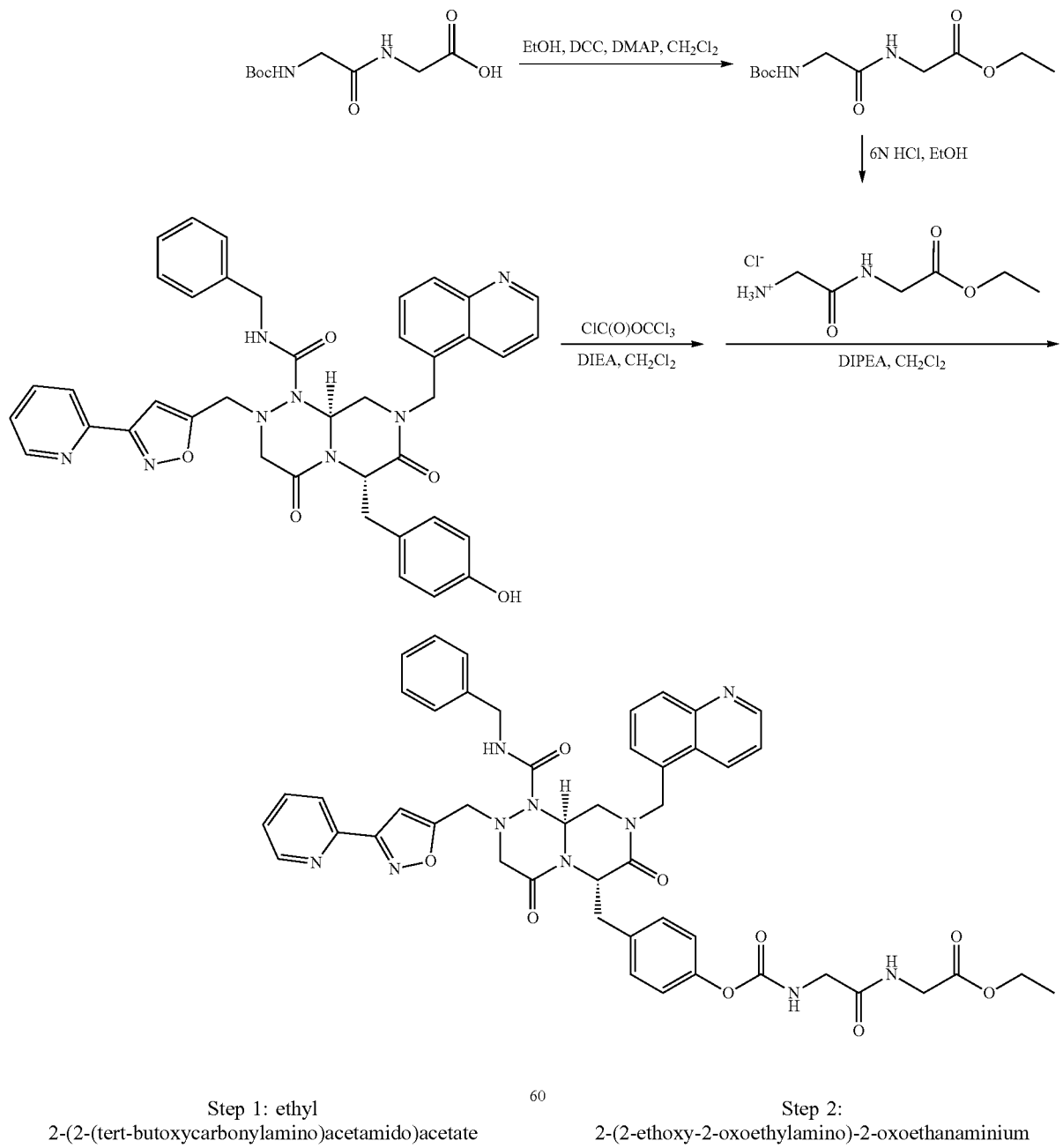

Scheme 11

Step 1: ethyl 2-(2-(tert-butoxycarbonylamino)acetamido)acetate

Step 2: 2-(2-ethoxy-2-oxoethylamino)-2-oxoethanaminium chloride

To a suspension of 2-(2-(tert-butoxycarbonylamino)acetamido)acetic acid (0.5 g, 2.15 mmol) in $CH_2Cl_2$ (8 mL) was added EtOH (0.14 mL, 2.37 mmol), DCC (0.49 g, 2.37 mmol) and DMAP (29 mg, 0.24 mmol). The reaction Ethyl 2-(2-(tert-butoxycarbonylamino)acetamido)acetate (0.53 g, 2.04 mmol) was treated with 6N HCl (5 mL) in EtOH (5 mL) at room temperature overnight. Evaporation to remove all volatiles gave the desired product (0.36 g) as a white solid. ¹H-NMR (300 MHz, DMSO-d₆) δ 8.84 (br s, 3H), 8.71 (br s, 1H), 4.11 (q, J=6 Hz, 2H), 3.94 (d, J=6 Hz, 2H), 3.6 (d, J=3 Hz, 2H), 1.20 (t, J=7.5 Hz, 3H).

Step 3: ethyl 2-(2-((4-((((6S,9aS)-1-(benzylcarbamoyl)-4,7-dioxo-2-((3-(pyridin-2-yl)isoxazol-5-yl)methyl)-8-(quinolin-5-ylmethyl)octahydro-1H-pyrazino[2,1-c][1,2,4]triazin-6-yl)methyl)phenoxy)carbonylamino)acetamido)acetate To a solution of (6S,9aS)—N-benzyl-6-(4-hydroxybenzyl)-4,7-dioxo-2-((3-(pyridin-2-yl)isoxazol-5-yl)methyl)-8-(quinolin-5-ylmethyl)octahydro-1H-pyrazino[2,1-c][1,2,4]triazine-1-carboxamide (0.13 g, 0.18 mmol) in CH₂Cl₂ at −15° C. under argon was added diphosgene (31 μL, 0.26 mmol) and DIEA (44.6 μL, 0.26 mmol). The reaction mixture was stirred at room temperature under argon for 2 hours. To this reaction mixture at −5° C. was added 2-(2-ethoxy-2-oxoethylamino)-2-oxoethanaminium chloride (0.22, 1.13 mmol), DIEA (0.29 mL, 1.67 mmol) and CH₂Cl₂ (2.3 mL). The reaction mixture was continued to stir under argon at room temperature for another 2 hours prior to adding Et₂O (5 mL). The insoluble material was removed via filtration. Evaporation to dryness and purification by silica-gel chromatography using EtOAc/CH₃OH gave the title product (116 mg) as a white solid. MS (ESI): m/z 895.3 (M+H)⁺.

Example 13

Compounds 12-34 listed in Table 1 were prepared based on the procedures analogs to that used in Example 6-12, using compounds 1-4 exemplified in Examples 2-5 and the starting materials listed in Table 2, accordingly.

TABLE 1

| Compound | Structure | Analytical HPLC purity | MS (ESI) [m/z (M + H)⁺] |
|---|---|---|---|
| 12 | 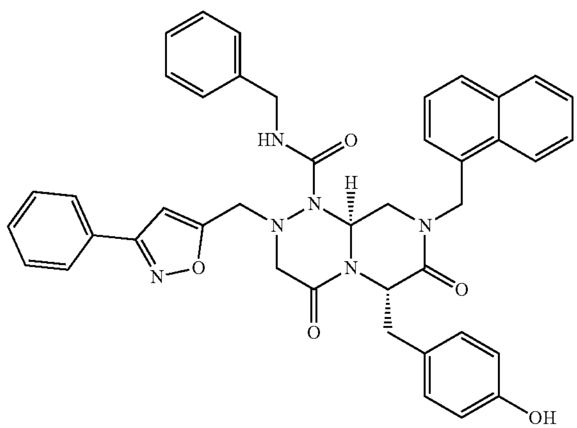 [SMILES: O=C1[C@H](Cc2ccc(O)cc2)N2C(=O)CN(Cc3cc(-c4ccccc4)no3)N(C(=O)NCc3ccccc3)[C@H]2CN1Cc1cccc2ccccc12] | 99% | 707.3 |
| 13 | 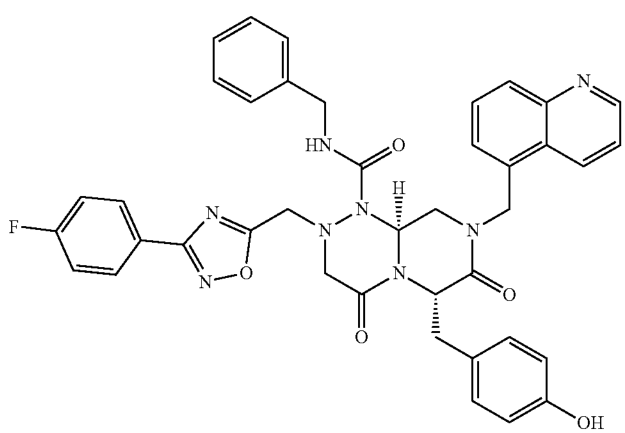 [SMILES: O=C1[C@H](Cc2ccc(O)cc2)N2C(=O)CN(Cc3nc(-c4ccc(F)cc4)no3)N(C(=O)NCc3ccccc3)[C@H]2CN1Cc1cccc2ncccc12] | 98% | 727.3 |

TABLE 1-continued

| Compound | Structure | Analytical HPLC purity | MS (ESI) [m/z (M + H)+] |
|---|---|---|---|
| 14 | 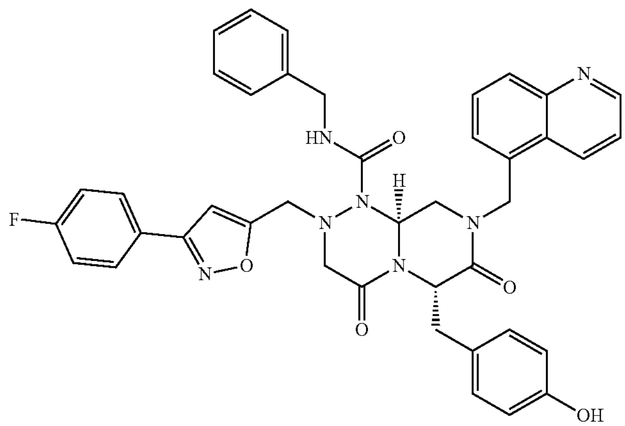 [SMILES: O=C1[C@H](Cc2ccc(O)cc2)N2C(=O)CN(Cc3cc(-c4ccc(F)cc4)no3)N(C(=O)NCc3ccccc3)[C@H]2CN1Cc1cccc2ncccc12] | >99% | 726.4 |
| 15 | 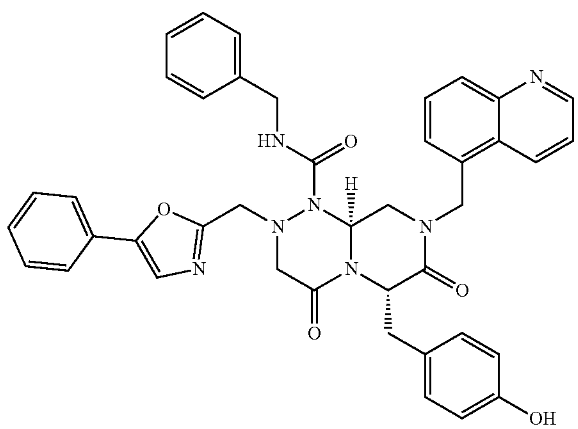 [SMILES: O=C1[C@H](Cc2ccc(O)cc2)N2C(=O)CN(Cc3ncc(-c4ccccc4)o3)N(C(=O)NCc3ccccc3)[C@H]2CN1Cc1cccc2ncccc12] | >99% | 708.2 |
| 16 | 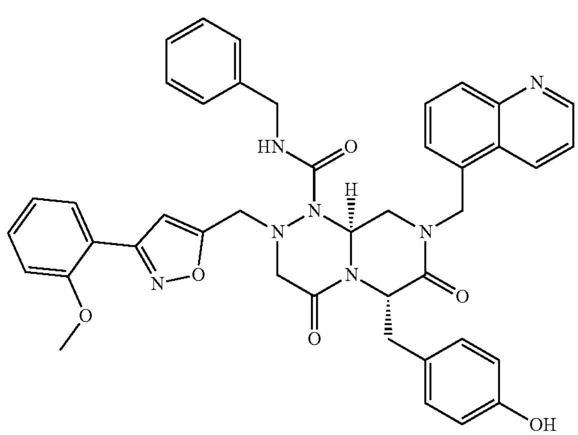 [SMILES: COc1ccccc1-c1cc(CN2CC(=O)N3[C@@H](Cc4ccc(O)cc4)C(=O)N(Cc4cccc5ncccc45)C[C@@H]3N2C(=O)NCc2ccccc2)on1] | >99% | 738.4 |

TABLE 1-continued

| Compound | Structure | Analytical HPLC purity | MS (ESI) [m/z (M + H)+] |
|---|---|---|---|
| 17 | 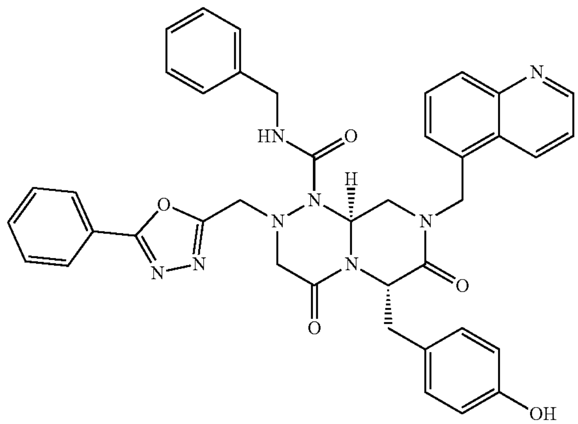 [SMILES: O=C1[C@H](Cc2ccc(O)cc2)N2C(=O)CN(Cc3nnc(-c4ccccc4)o3)N(C(=O)NCc3ccccc3)[C@H]2CN1Cc1cccc2ncccc12] | >99% | 709.3 |
| 18 | 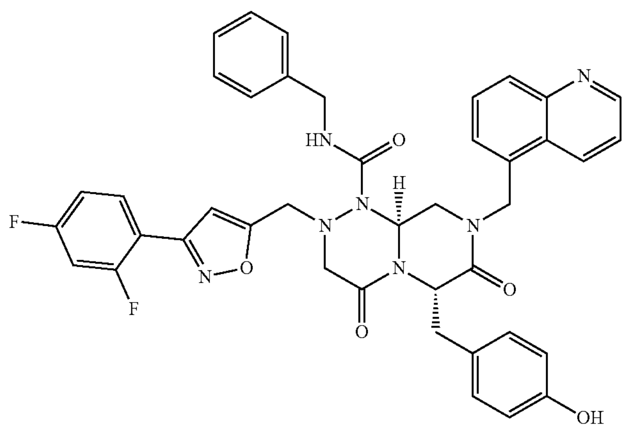 [SMILES: O=C1[C@H](Cc2ccc(O)cc2)N2C(=O)CN(Cc3cc(-c4ccc(F)cc4F)no3)N(C(=O)NCc3ccccc3)[C@H]2CN1Cc1cccc2ncccc12] | 99% | 744.4 |
| 19 | 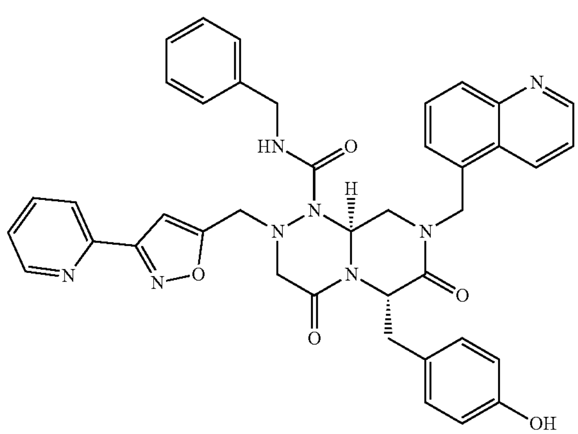 [SMILES: O=C1[C@H](Cc2ccc(O)cc2)N2C(=O)CN(Cc3cc(-c4ccccn4)no3)N(C(=O)NCc3ccccc3)[C@H]2CN1Cc1cccc2ncccc12] | >97% | 709.3 |

TABLE 1-continued

| Compound | Structure | Analytical HPLC purity | MS (ESI) [m/z (M + H)+] |
|---|---|---|---|
| 20 | 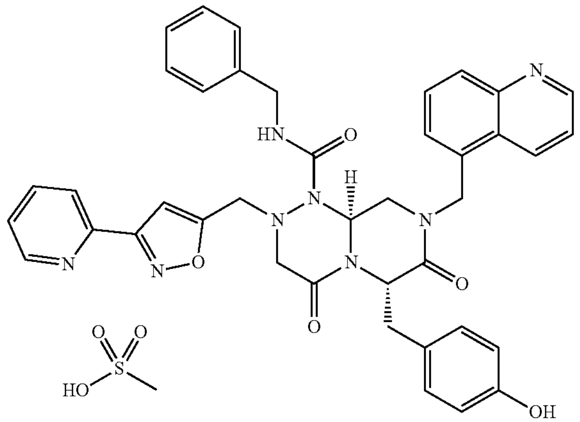 | 98% | 709.2 |
| 21 | 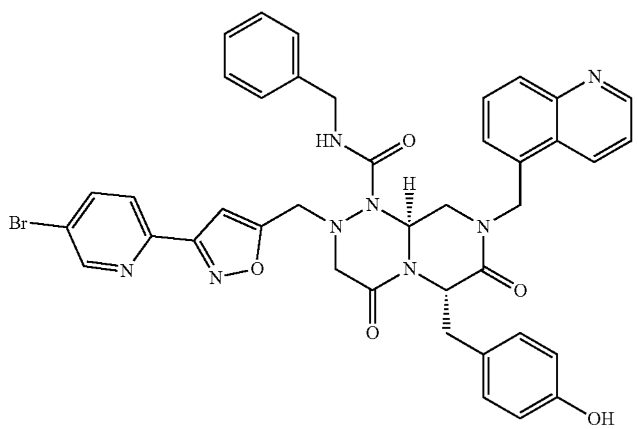 [SMILES: O=C1[C@H](Cc2ccc(O)cc2)N2C(=O)CN(Cc3cc(-c4ccc(Br)cn4)no3)N(C(=O)NCc3ccccc3)[C@H]2CN1Cc1cccc2ncccc12] | 98% | 787.4, 789.2 |
| 22 | 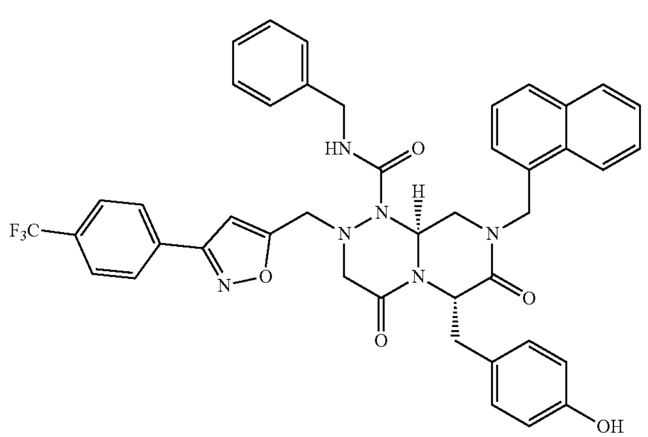 [SMILES: O=C1[C@H](Cc2ccc(O)cc2)N2C(=O)CN(Cc3cc(-c4ccc(C(F)(F)F)cc4)no3)N(C(=O)NCc3ccccc3)[C@H]2CN1Cc1cccc2ccccc12] | 95% | 775.2 |

TABLE 1-continued

| Compound | Structure | Analytical HPLC purity | MS (ESI) [m/z (M + H)+] |
|---|---|---|---|
| 23 | 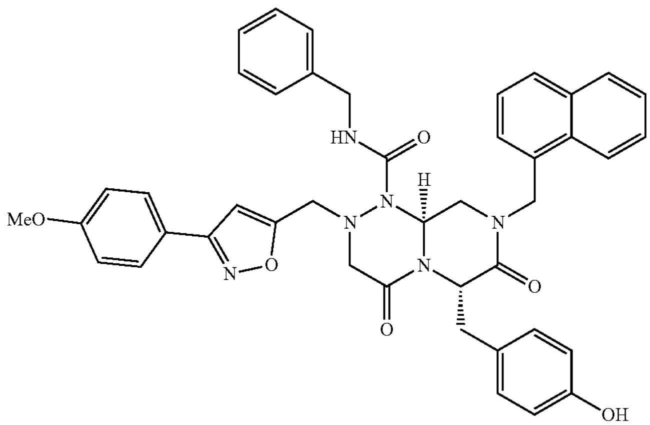 [SMILES: COc1ccc(-c2cc(CN3CC(=O)N4[C@@H](Cc5ccc(O)cc5)C(=O)N(Cc5cccc6ccccc56)C[C@@H]4N3C(=O)NCc3ccccc3)on2)cc1] | 96% | 737.2 |
| 24 | 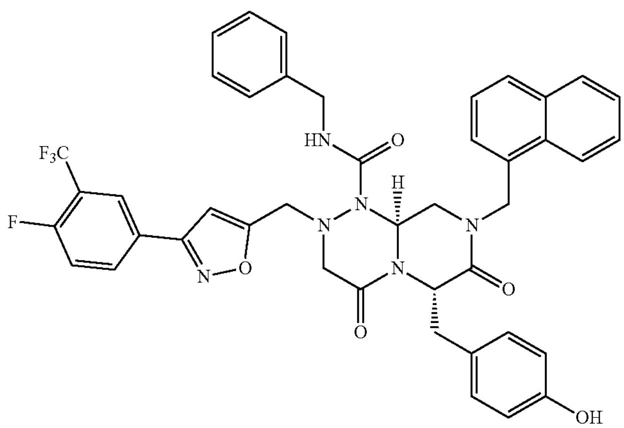 [SMILES: O=C1[C@H](Cc2ccc(O)cc2)N2C(=O)CN(Cc3cc(-c4ccc(F)c(C(F)(F)F)c4)no3)N(C(=O)NCc3ccccc3)[C@H]2CN1Cc1cccc2ccccc12] | 98% | 793.4 |
| 25 | 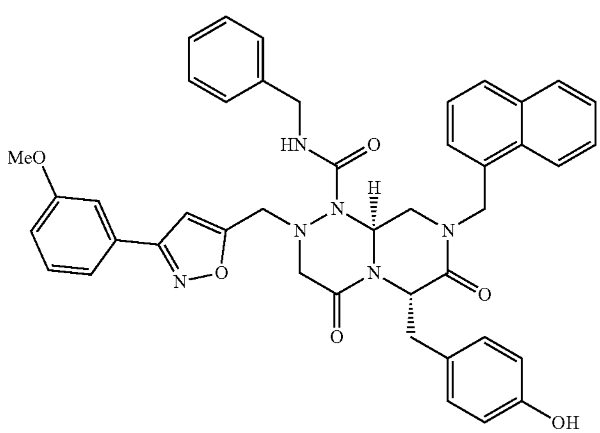 [SMILES: COc1cccc(-c2cc(CN3CC(=O)N4[C@@H](Cc5ccc(O)cc5)C(=O)N(Cc5cccc6ccccc56)C[C@@H]4N3C(=O)NCc3ccccc3)on2)c1] | 94% | 737.2 |

TABLE 1-continued

| Compound | Structure | Analytical HPLC purity | MS (ESI) [m/z (M + H)+] |
|---|---|---|---|
| 26 | 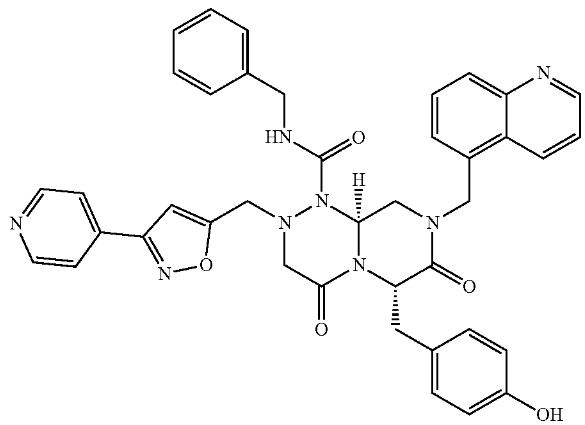 [SMILES: O=C1[C@H](Cc2ccc(O)cc2)N2C(=O)CN(Cc3cc(-c4ccncc4)no3)N(C(=O)NCc3ccccc3)[C@H]2CN1Cc1cccc2ncccc12] | 100% | 709.3 |
| 27 | 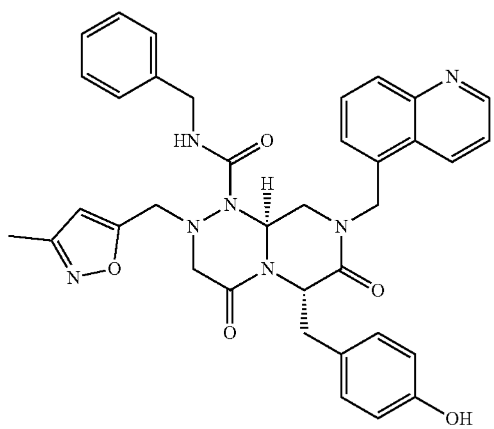 [SMILES: Cc1cc(CN2CC(=O)N3[C@@H](Cc4ccc(O)cc4)C(=O)N(Cc4cccc5ncccc45)C[C@@H]3N2C(=O)NCc2ccccc2)on1] | >98% | 646.3 |
| 28 | 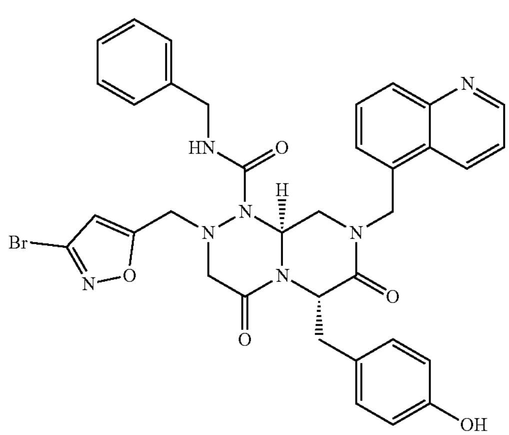 [SMILES: O=C1[C@H](Cc2ccc(O)cc2)N2C(=O)CN(Cc3cc(Br)no3)N(C(=O)NCc3ccccc3)[C@H]2CN1Cc1cccc2ncccc12] | 99% | 710.3, 712.2 |

TABLE 1-continued

| Compound | Structure | Analytical HPLC purity | MS (ESI) [m/z (M + H)+] |
|---|---|---|---|
| 29 | 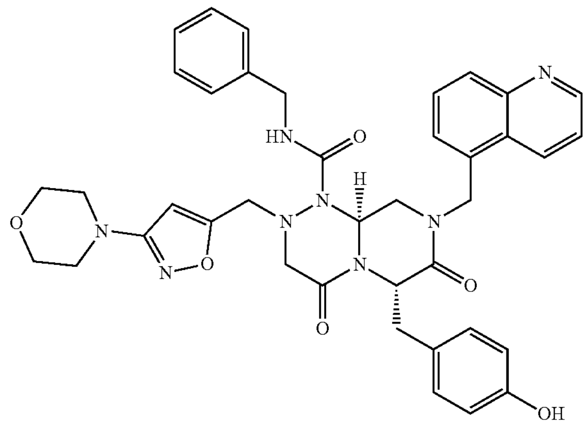 [SMILES: O=C1[C@H](Cc2ccc(O)cc2)N2C(=O)CN(Cc3cc(N4CCOCC4)no3)N(C(=O)NCc3ccccc3)[C@H]2CN1Cc1cccc2ncccc12] | 98% | 716.5 |
| 30 | 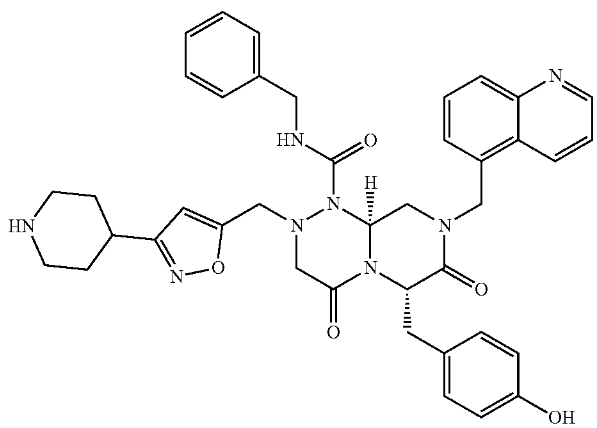 [SMILES: O=C1[C@H](Cc2ccc(O)cc2)N2C(=O)CN(Cc3cc(C4CCNCC4)no3)N(C(=O)NCc3ccccc3)[C@H]2CN1Cc1cccc2ncccc12] | 99% | 715.3 |
| 31 | 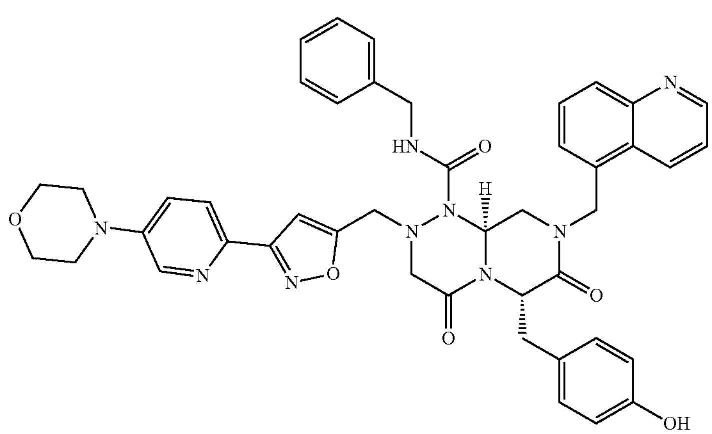 [SMILES: O=C1[C@H](Cc2ccc(O)cc2)N2C(=O)CN(Cc3cc(-c4ccc(N5CCOCC5)cn4)no3)N(C(=O)NCc3ccccc3)[C@H]2CN1Cc1cccc2ncccc12] | 100% | 794.4 |

TABLE 1-continued

| Compound | Structure | Analytical HPLC purity | MS (ESI) [m/z (M + H)+] |
|---|---|---|---|
| 32 | 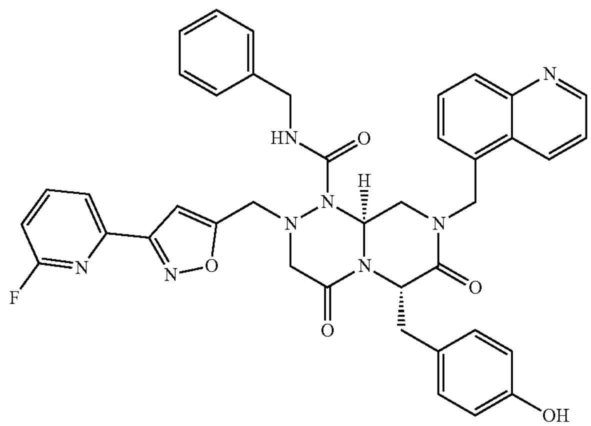 [SMILES: O=C1[C@H](Cc2ccc(O)cc2)N2C(=O)CN(Cc3cc(-c4cccc(F)n4)no3)N(C(=O)NCc3ccccc3)[C@H]2CN1Cc1cccc2ncccc12] | >98% | 727.4 |
| 33 | 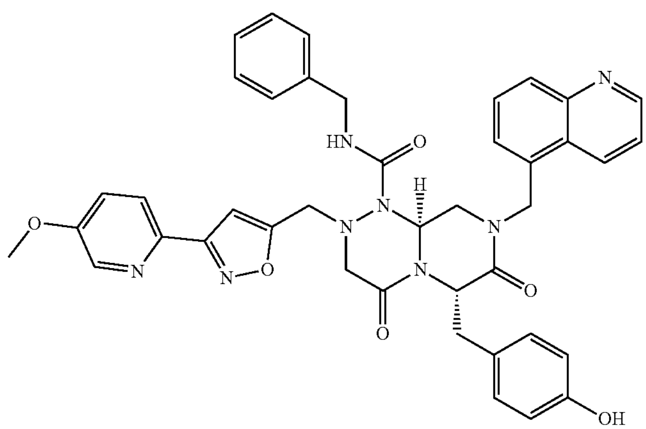 [SMILES: COc1ccc(-c2cc(CN3CC(=O)N4[C@@H](Cc5ccc(O)cc5)C(=O)N(Cc5cccc6ncccc56)C[C@@H]4N3C(=O)NCc3ccccc3)on2)nc1] | 100% | 739.2 |
| 34 | 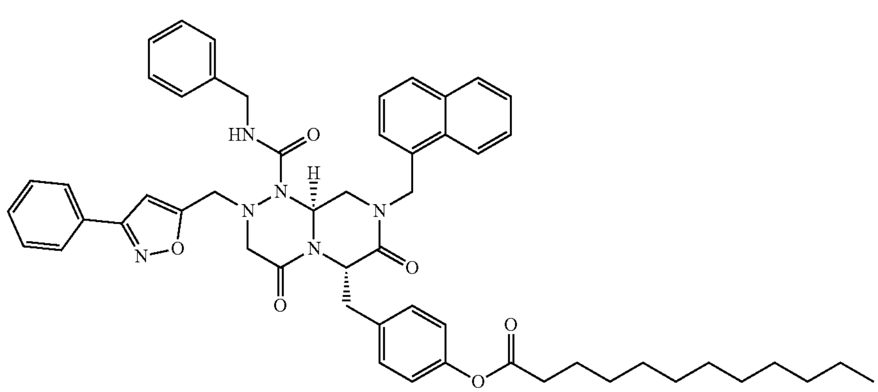 [SMILES: CCCCCCCCCCCC(=O)Oc1ccc(C[C@H]2C(=O)N(Cc3cccc4ccccc34)C[C@H]3N2C(=O)CN(Cc2cc(-c4ccccc4)no2)N3C(=O)NCc2ccccc2)cc1] | >99% | 889.5 |

Example 14

Starting materials used for the preparation of exemplary compounds of the present invention listed in the examples and Table 1 are listed in Table 2.

TABLE 2

| Intermediates and Starting Materials | Structure | CAS# or comment on synthesis |
|---|---|---|
| 35 | Br-CH2-(isoxazole)-(2-methoxyphenyl) | 886364-40-5 |
| 36 | Br-CH2-(1,3,4-oxadiazole)-phenyl | 26114-48-7 |
| 37 | Br-CH2-(isoxazole)-(4-fluorophenyl) | 5262-25-9 |
| 38 | Cl-CH2-(1,2,4-oxadiazole)-(4-fluorophenyl) | 721428-34-8 |
| 39 | Br-CH2-(oxazole)-phenyl | 14372-43-1 |
| 40 | Br-CH2-(3-methylisoxazole) | 36958-61-9 |
| 41 | Br-CH2-(3-bromoisoxazole) | 88982-28-9 |

TABLE 2-continued

| Intermediates and Starting Materials | Structure | CAS# or comment on synthesis |
|---|---|---|
| 42 | Br-[CH2-(isoxazole-5-yl)]-3-(4-methoxyphenyl) | Prepared according to the procedures described above in Example 6, starting from 4-methoxybenzaldehyde |
| 43 | Br-[CH2-(isoxazole-5-yl)]-3-(3-methoxyphenyl) | Prepared according to the procedures described above in Example 6, starting from 3-methoxybenzaldehyde |
| 44 | Br-[CH2-(isoxazole-5-yl)]-3-(3-CF3-4-F-phenyl) | Prepared according to the procedures described above in Example 6, starting from 4-fluoro-3-(trifluoromethyl)benzaldehyde |
| 45 | Br-[CH2-(isoxazole-5-yl)]-3-(4-CF3-phenyl) | Prepared according to the procedures described above in Example 6, starting from 4-trifluoromethyl)benzaldehyde |
| 46 | Br-[CH2-(isoxazole-5-yl)]-3-(pyridin-2-yl) | Prepared according to the procedures described above in Example 6, starting from pyridine-2-aldoxime |
| 47 | pyridin-2-yl-C(Cl)=NOH | Prepared according to the procedures described above in Example 8, starting from picolinaldehyde or pyridine-2-aldoxime |
| 48 | Br-[CH2-(isoxazole-5-yl)]-3-(5-bromopyridin-2-yl) | Prepared according to the procedures described above in Example 6, starting from 5-bromopicolinaldehyde |

TABLE 2-continued

| Intermediates and Starting Materials | Structure | CAS# or comment on synthesis |
|---|---|---|
| 49 | [isoxazole with CH2Cl and pyridin-4-yl, HCl salt] | 865610-66-8 |
| 50 | [tetrahydropyran-4-yl C(Cl)=NOH] | Prepared according to the procedures described above in Examples 8 and 10, starting from tetrahydro-2H-pyran-4-carbaldehyde |
| 51 | [N-Boc-piperidin-4-yl C(Cl)=NOH] | Prepared according to the procedures described above in Examples 8 and 10, starting from tert-butyl 4-formylpiperidine-1-carboxylate |
| 52 | [isoxazole with CH2Br and 6-fluoropyridin-2-yl] | Prepared according to the procedures described above in Example 6, starting from 6-fluoropicolinaldehyde |
| 53 | [isoxazole with CH2Br and 5-methoxypyridin-2-yl] | Prepared according to the procedures described above in Example 6, starting from 5-methoxypicolinaldehyde |
| 54 | [5-morpholino-pyridine-2-carbaldehyde] | Prepared according to the procedure described in WO 2009027746, starting from 5-fluoropicolinaldehyde |

Example 15

Figure 1:
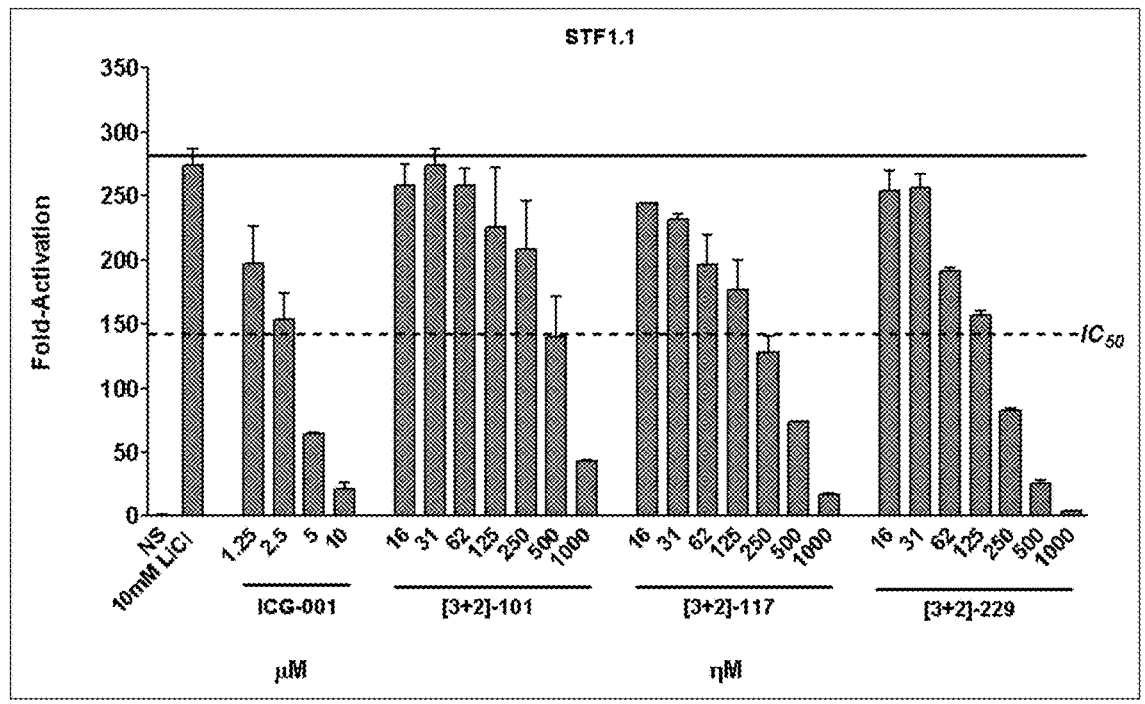
FIG. 1 shows, according to non-limiting aspects of the present invention, results of a SuperTOPFLASH cell-based luciferase assay (Wnt-driven Luciferase Activity in Stably Transfected Cell Line, Hek293, STF1.1), comparing the CBP/β-Catenin inhibition activities of three exemplary isoxazole compounds of the present invention (coded [3+2]-101, [3+2]-117 and [3+2]-229; each compared in concentrations between 16 and 1000 nM), with the art-recognized specific CBP/β-Catenin inhibitor ICG-001 used as a positive control (at 1.25, 2.5, 5 and 10 μM). As is readily apparent, the three inventive isoxazole compounds generally have ~10× or greater potency than that of the control compound ICG-001 in this assay.

Three Representative Isoxazole Compounds ([3+2]-101, [3+2]-117 and [3+2]-229) were Shown Generally to have ~10× or Greater Potency than that of the Positive Control Compound ICG-001 in the Art-Recognized SuperTOPFLASH Cell-Based Luciferase Assay FIG. 1 shows, according to non-limiting aspects of the present invention, results of a SuperTOPFLASH cell-based luciferase assay (Wnt-driven Luciferase Activity in Stably Transfected Cell Line, Hek293, STF1.1), comparing the CBP/β-Catenin inhibition activities of three exemplary isoxazole compounds of the present invention (coded [3+2]-101, [3+2]-117 and [3+2]-229; each compared in concentrations between 16 and 1000 nM), with the art-recognized CBP/β-Catenin inhibitor ICG-001 used as a positive control (at 1.25, 2.5, 5 and 10 μM). As is readily apparent, the three representative inventive isoxazole compounds have at least ~10× or greater potency than that of the control compound ICG-001 in this assay. The potency of the majority of the disclosed CBP/β-Catenin inhibitor compounds was determined to generally be at least ~3× or greater than that of the control compound ICG-001 in this assay.

Example 16

Figure 2:
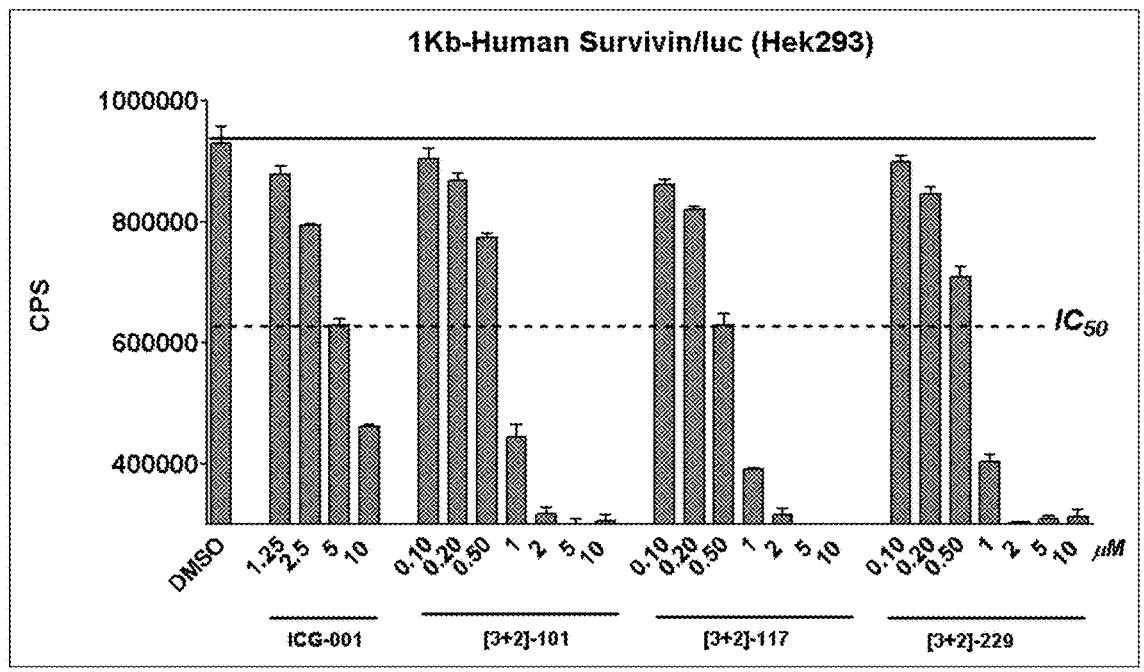
FIG. 2 shows, according to additional non-limiting aspects of the present invention, results of a survivin promoter-driven luciferase activity assay (assay of Human survivin 1 Kb-promoter-driven luciferase activity in stably transfected Hek293 cell line; 1 Kb Hu-survivin/luc-Hek293), comparing the CBP/β-Catenin inhibition activities of three exemplary isoxazole compounds of the present invention (coded [3+2]-101, [3+2]-117 and [3+2]-229; each compared in concentrations between 0.1 and 10 μM), with the art-recognized specific CBP/β-Catenin inhibitor ICG-001 used as a positive control (at 1.25, 2.5, 5 and 10 μM). As is readily apparent, the three inventive isoxazole compounds have $IC_{50}$ values generally at least ~10× or greater potency than that of the control compound ICG-001 in this assay.

Three Representative Isoxazole Compounds ([3+2]-101, [3+2]-117 and [3+2]-229) were Shown to Generally have ~10× or Greater Potency than that of the Positive Control Compound ICG-001 in the Art-Recognized Survivin Promoter-Driven Luciferase Activity Assay FIG. 2 shows, according to additional non-limiting aspects of the present invention, results of a survivin promoter-driven luciferase activity assay (assay of Human survivin 1 Kb-promoter-driven luciferase activity in stably transfected Hek293 cell line; 1 Kb Hu-survivin\luc-Hek293), comparing the CBP/β-Catenin inhibition activities of three exemplary isoxazole compounds of the present invention (coded [3+2]-101, [3+2]-117 and [3+2]-229; each compared in concentrations between 0.1 and 10 μM), with the art-recognized CBP/β-Catenin inhibitor ICG-001 used as a positive control (at 1.25, 2.5, 5 and 10 μM). As is readily apparent, these three representative inventive isoxazole compounds have $IC_{50}$ values at least ~10× or greater potency than that of the control compound ICG-001 in this assay. The $IC_{50}$ values of the majority of the disclosed CBP/β-Catenin inhibitor compounds was determined to generally be at least ~3× or greater than that of the control compound ICG-001 in this assay.

Example 17

The Representative Isoxazole Compound [3+2]-101 was Shown Generally have at Least ~10× or Greater Potency for Decreasing CBP/β-Catenin Based Transcription than that of the Positive Control Compound ICG-001 in the Art-Recognized SYBR-Green qPCR Assay for Survivin/BIRC5

Figure 3A:
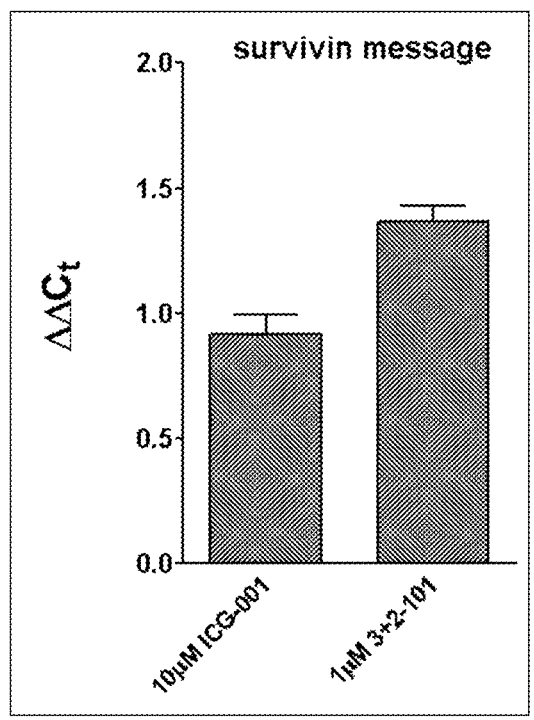
FIG. 3A and FIG. 3B show, according to yet additional non-limiting aspects of the present invention, results of a SYBR-Green qPCR assay for Survivin/BIRC5(CBP-specific) and EphB2(p300-specific) gene expression, using GAPDH as a control gene.
Figure 3B:
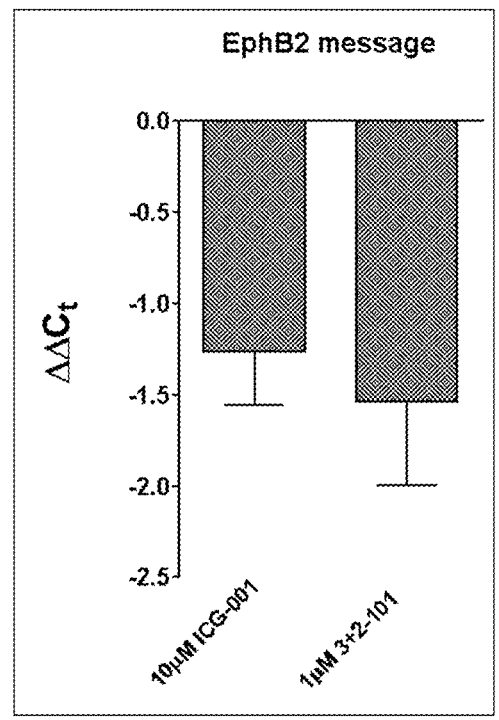

FIG. 3A and FIG. 3B show, according to yet additional non-limiting aspects of the present invention, results of a SYBR-Green qPCR assay for Survivin/BIRC5 (CBP-specific) and EphB2 (p300-specific) gene expression, using GAPDH as a control gene. FIG. 3A compares the inventive compound [3+2]-101 (at 1 μM) with the art-recognized positive control ICG-001 (at 10 μM) in inhibiting the CBP/β-catenin specific gene (H. Ma et al Oncogene 2005, 24, 3619-31) survivin gene expression (reflected as an increase in $\Delta\Delta C_t$). As is readily apparent, the CBP/β-Catenin expression inhibition activity of the inventive isoxazole is at least 10× greater than that of the control. FIG. 3B compares the inventive compound [3+2]-101 (at 1 μM) with the art-recognized positive control ICG-001 (at 10 μM) in stimulating EphB2 (p300/β-catenin-specific gene (Kumar S, et. al. Cancer Res. 2009, 69, 3736-45) gene expression (reflected as a decrease in $\Delta\Delta C_t$). As is readily apparent, the EphB2 gene expression stimulating activity of the representative inventive isoxazole is at least 10× greater than that of the control. This reflects a decrease in CBP/β-catenin based transcription with an increase in p300/β-catenin based transcription, mediated by the specific CBP/β-catenin inhibitory activities of [3+2]-101 and ICG-001.

Example 18

A Co-Immunoprecipitation Assay Ms Performed in SW480 Ceils to Further Confirm that the Positive Control Compound ICG-001 and the Representative Inventive Compound [3+2]-117 Selectively Disrupt/β-Catenin Binding to CBP, while Enhancing the Binding of β-Catenin to p300

Figures 4A, 4B:
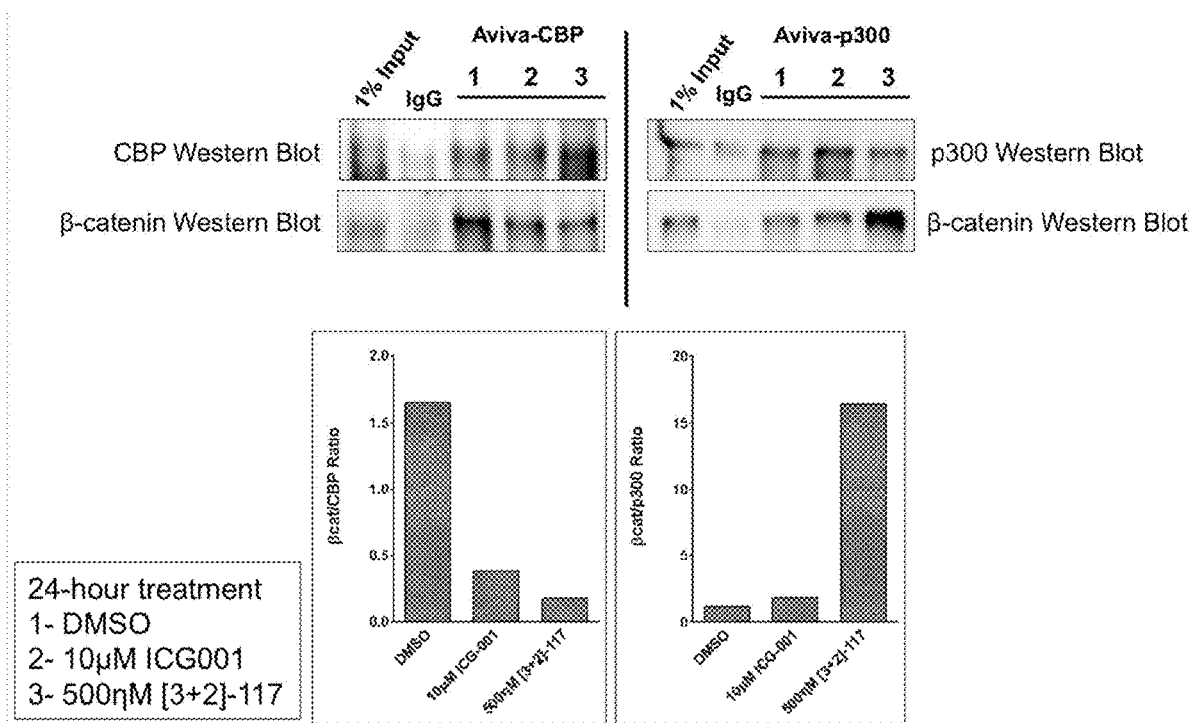
FIG. 4A and FIG. 4B show, according to further non-limiting aspects of the present invention, a co-immunoprecipitation assay that was performed in SW480 colorectal cancer cells as previously described (Emami K. et al. PNAS USA, 2004 Aug. 24; 101 (34): 12682-7) to further confirm that ICG-001 and [3+2]-117 selectively disrupt β-catenin binding to CBP (FIG. 4A), while enhancing the binding of β-catenin to p300 (FIG. 4B). Immunoprecipitation of β-catenin with CBP was inhibited by ICG-001 at 10 μM (FIG. 3A) and by [3+2]-117 at 500 nM. [3+2]-117 was approximately 20-fold more active compared with ICG-001 (compare lane 1 (DMSO control) with lanes 2 and 3). The minimal interaction seen in the SW480 cells between β-catenin and p300 was not blocked by ICG-001, despite the fact that CBP and p300 are highly homologous. In fact, treatment with 10 μM ICG-001 slightly increases the amount of β-catenin co-immunoprecipitated with p300 (FIG. 4B p300 IP, compare lanes 1 and 2), consistent with the switch from CBP/β-catenin mediated transcription to p300/β-catenin mediated transcription associated with the initiation of differentiation. [3+2]-117 at 500 nM dramatically increased the interaction of β-catenin with p300 ((FIG. 4B p300 IP, compare lanes 1 and 3). Quantification of the immunoblotting data based upon pixelation is shown below the immunoblots.

FIG. 4A and FIG. 4B, show, according to further non-limiting aspects of the present invention, a co-immunoprecipitation assay that was performed in SW480 cells as previously described (Emami K. et al. PNAS USA, 2004 Aug. 24; 101 (34): 12682-7) to further confirm that the positive control compound ICG-001 and [3+2]-117 selectively disrupt β-catenin binding to CBP (FIG. 4A), while enhancing the binding of β-catenin to p300 (FIG. 4B). Immunoprecipitation of β-catenin with CBP was inhibited by ICG-001 at 10 μM (FIG. 3A) and by [3+2]-117 at 500 nM. [3+2]-117 was approximately 20-fold more active compared with ICG-001 (compare lane 1 (DMSO control) with lanes 2 and 3. The minimal interaction seen in the SW480 cells between β-catenin and p300 was not blocked by ICG-001, despite the fact that CBP and p300 are highly homologous. In fact, treatment with 10 μM ICG-001 slightly increases the amount of β-catenin co-immunoprecipitated with p300 (FIG. 4B p300 IP, compare lanes 1 and 2), consistent with the switch from CBP/β-catenin transcription to p300/β-catenin transcription associated with the initiation of differentiation. [3+2]-117 at 500 nM dramatically increased the interaction of β-catenin with p300 ((FIG. 4B p300 IP, compare lanes 1 and 3). Quantification of the immunoblotting data based upon pixelation is shown below the immunoblots.

Example 19

A Bleomycin Induced Mouse Model of Idiopathic Pulmonary Fibrosis (IPF) was Used to Demonstrate that the Efficacy of Representative Inventive Compounds [3+2]-120A and [3+2]-120B Compared Favorably to Historical Control Data for Both Pirfenidone and Nintedanib Bleomycin induced model of IPF. Representative inventive compound [3+2]-120A (compound 20), as has been previously shown with first (ICG-001) and second (PRI-724) generation CBP/β-catenin antagonists, demonstrated efficacy in the bleomycin induced model of IPF in mice (SMC Laboratories, Tokyo, Japan). Specifically, oral (p.o.) administration by gavage of [3+2]-120A at 100 mg/kg/day (A-low) and 400 mg/kg/day (A-high) compared favorably to historical control data for overall survival and Ashcroft scoring for both FDA approved therapeutic agents for IPF, i.e., pirfenidone (400 mg/kg/day p.o.) and nintedanib (100 mg/kg/day p.o.) when administration was initiated on day 7 after bleomycin and continued for 2 weeks. Representative inventive compound [3+2]-120B (compound 11) at 400 mg/kg/day (high) also compared favorably to the historical control data.

Results. FIG. 5 shows, according to further non-limiting aspects of the present invention, that there was a significant increase in weight gain in mice treated with [3+2]-120A (both dosage groups) and with [3+2]-20B (high dosage group), and all mice survived (FIG. 6), whereas historically approximately 30% of the mice die before day 21 even when treated in this model. Moreover, a significant decrease in lung weights and in Ashcroft scores (Table 3) was seen (FIGS. 7A-7D) in [3+2]-120A treated mice (both dosage groups) and in [3+2]-120B (high dosage group) treated mice, based on histological analysis (FIGS. 8A-8E). FIGS. 8A-8E are as follows: historical bleomycin saline treated control (8A, "ID:103"); [3+2]-120A low dose (8B, "ID: 102"); [3+2]-120A high dose (8C, "ID:201"); [[3+2]-120B low dose (8D, ID:302"); and [3+2]-120B high dose (8E, ID:401"). In all treatment groups, there is a significant reduction in extracellular collagen deposition compared to the bleomycin saline treated historical control as judged by Masson's trichrome blue staining.

Based on these results, the [3+2] series compounds are efficacious in the bleomycin-induced model of idiopathic pulmonary fibrosis when dosed orally (per os, p.o).

TABLE 3

| Parameter (mean +/− SD) | Compound A low (n = 3) | Compound A high (n = 3) | Compound B low (n = 3) | Compound B high (n = 3) |
|---|---|---|---|---|
| Body weight (g) | 18.2 +/− 0.7 | 16.9 +/− 3.8 | 15.1 +/− 3.8 | 19.5 +/− 1.6 |
| Post-caval lobe weight (mg) | 21 +/− 9 | 25 +/− 18 | 39 +/− 17 | 21 +/− 6 |
| Left lung weight (mg) | 65 +/− 19 | 66 +/− 33 | 77 +/− 15 | 65 +/− 13 |

| Parameter (mean +/− SD) | Compound A ow (n = 3) | Compound A high (n = 3) | Compound B low (n = 3) | Compound B high (n = 3) |
|---|---|---|---|---|
| Ashcroft score | 2.2 +/− 1.7 | 2.5 +/− 2.0 | 3.9 +/− 1.4 | 2.1 +/− 0.7 |

Example 20

A STAM™ Mouse Model of NASH-HCC was Used to Demonstrate Efficacy of Representative Inventive Compound [3+2]-120A Representative inventive compound [3+2]-120A (compound 20), demonstrated efficacy in the proprietary STAM™ mouse model of NASH-HCC in mice (SMC Laboratories, Tokyo, Japan). Specifically, in an ongoing study, oral (p.o.) administration by gavage of [3+2]-120A at 100 mg/kg/day (A-low) and 400 mg/kg/day (A-high) compared favorably to vehicle control data for overall survival after 4 weeks of treatment. In the vehicle control treated group only 5 out of 8 mice survived, whereas in the 3+2]-120A at 100 mg/kg/day (A-low) and 400 mg/kg/day (A-high), 7 out of 8 and 8 out of 8 mice survived respectively.

Example 21

A NG/Nga Mouse Model of Atopic Dermatitis Ms Used to Demonstrate the Efficacy of Representative Inventive Compound [3+2]-121A in Decreasing the TEWL Score and Dermatitis Scores Compared to Vehicle Control NG/Nga Mouse Model of Atopic Dermatitis:
NC/Nga mice (female) were obtained from CHARLES RIVER LABORATORIES JAPAN INC. Mice were randomized into 4 groups of 8 mice on Day 0 based on their body weight and dermatitis score. Eight NC/Nga mice were topically administered test compound-containing [3+2]-121A (compound 34) ointment (in a volume of 100 mg) once daily from Day 0 to Day 13, or vehicle control (hydrophilic petrolatum). Representative compound [3+2]-121A, at both low (100 uM) and high (500 uM) dose levels, significantly decreased the TEWL score and dermatitis scores compared to vehicle control.

Representative test substance [3+2]-121A was formulated in hydrophilic petrolatum at low (100 uM) and high (500 uM) dosages (referred to in the study as [3+2]-121A and [3+2]-121B, respectively). 7-week-old female NC/Nga mice were used. The first induction of atopic dermatitis was performed three weeks before compound administration, for which the mice were shaved of hair on their backs and behind the ears with a clipper and a shaver. Then the mice had their hair removed completely with a depilatory agent (Epilat™, Kracie Home Products, Ltd.) before 100 mg of Biostir AD® ointment was applied to the shaved dorsal skin and both surfaces of each ear evenly with a plastic spoon. The second induction of atopic dermatitis was performed subsequently. The mice were shaved of hair on their backs and behind the ears, then 150 μl of 4% sodium lauryl sulfate solution was applied to the back and behind the ears with a plastic spoon. After this, it was dried with a hair dryer (cold air) and then left to dry naturally for about 1 to 2 hours. 100 mg of Biostir AD® ointment was applied to the shaved dorsal skin and both surfaces of each ear evenly with a plastic spoon. This procedure was repeated twice a week for three weeks. Twenty-four atopic dermatitis model mice were sorted into 3 groups of 8 mice based on their body weight and dermatitis severity score on the morning at Day 0. Vehicle control (hydrophilic petrolatum), [3+2]-121A or [3+2]-121B was administered topically in a volume of 100 mg once daily from Day 0 to Day 13. Body weight and food consumption were measured once a week at Day 0, 7 and 14. The severity of dermatitis was evaluated at Day 0, 3, 7, 10 and 14. The development of 1) erythema/hemorrhage, 2) scarring/dryness, 3) edema, 4) excoriation/erosion were scored as 0 (none), 1 (mild), 2 (moderate) and 3 (severe). The sum of the individual scores was taken as the dermatitis score. The TEWL was evaluated at Day 0 and at Day 14 after administration. Histological analyses were performed on lower neck dorsal skin and auricle that were fixed in 10% neutral formalin, embedded in paraffin and sectioned at 3-4 μm sections and stained with hematoxylin-eosin using Carrazzi's hematoxylin solution. For analysis of the skin area, bright field images of HE-stained sections were randomly captured using a digital camera (DS-Fi3; Nikon) at 2 and 4-fold magnification. Statistical analyses were performed using Prism Software 6 (GraphPad Software, USA). Statistical analyses were performed using Dunnett's Comparison Test. Comparisons were made between the following groups; Group 1 (Vehicle) vs. Group 2 ([3+2]-121A) and Group 3 ([3+2]-121B). P values <0.05 were considered statistically significant. Results were expressed as mean±SD. There were no significant differences in mean body weight at any day during the treatment period between the Vehicle group and the treatment groups, attesting to the lack of toxicity of the treatment (FIG. 9). There were no significant differences in the food consumption per mouse between the Vehicle group and the treatment groups (FIG. 10).

Dermatitis severity score: The [3+2]-121A group showed a significant decrease in the dermatitis severity score on the back on Days 10 and 14 compared with the Vehicle group (FIG. 11A back 11B total).

TEWL analysis (transepidermal water loss (TEWL) is the amount of water that passively evaporates through skin to the external environment due to water vapor pressure gradient on both sides of the skin barrier and is used to characterize skin barrier function): The [3+2]-121A and 121B group showed a significant decrease in the TEWL at day 14 (FIG. 12), attesting to the increased barrier function associated with the treatment.

Histological analysis: showed a significant reduction in inflammation and inflammatory cell influx in both the [3+2]-121A and [3+2]-121B group as shown in representative photomicrographs (FIGS. 13A-13C).

The invention and the manner and process of making and using it, are now described in such full, clear, concise, and exact terms as to enable any person skilled in the art to which it pertains, to make and use the same.

It will be appreciated that, although specific embodiments of the invention have been described herein for the purposes of illustration, various modifications may be made without departing from the spirit and scope of the invention. Accordingly, the invention is not limited except by the appended claims.

All of the above U.S. patents, U.S. patent application publications, U.S. patent applications, foreign patents, foreign patent applications and non-patent publications referred to in this specification, are incorporated herein by reference.

While certain aspects have been described and shown in the accompanying drawings, it is to be understood that such aspects are merely illustrative of and not restrictive on the broad invention, and that the invention is not limited to the specific constructions and arrangements shown and described, since various other modifications may occur to those of ordinary skill in the art. The description is thus to be regarded as illustrative instead of limiting.

The invention claimed is:

1. A compound of formula (Ia):

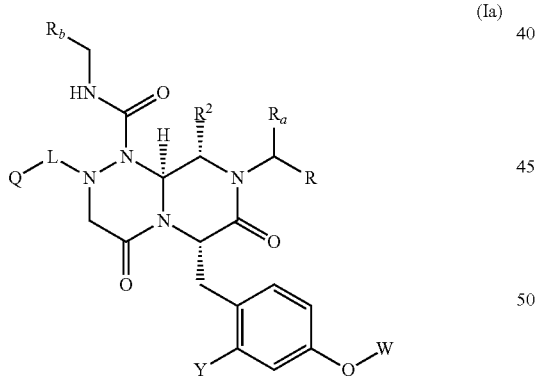

(Ia)

or a pharmaceutically acceptable salt thereof, wherein:
$R_a$ is hydrogen or —$CH_3$;
$R_b$ is a monocyclic aryl group having 5 to 7 ring members, which may have 1 to 2 heteroatoms selected from nitrogen, oxygen or sulfur, and which may have one or more substituents selected from a group consisting of halide, cyano, and lower alkyl;
R is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkyl amino, $C_{1-4}$dialkylamino, halogen, perfluoro $C_{1-4}$alkyl, $C_{1-3}$alkoxy, nitro, carboxy, cyano, sulfuryl, and hydroxyl group; or a bicyclic aryl group, or substituted bicyclic aryl, having 8 to 11 ring members, which may have 1 to 3 heteroatoms selected from nitrogen, oxygen or sulfur, where the substituted bicyclic aryl may have one or more substituents independently selected from amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group;

$R^2$ is hydrogen, or —$CH_3$;

Y is selected from: hydrogen, deuterium, or halogen;

W is hydrogen, phosphate or phosphate salt, or X, wherein X is selected from:

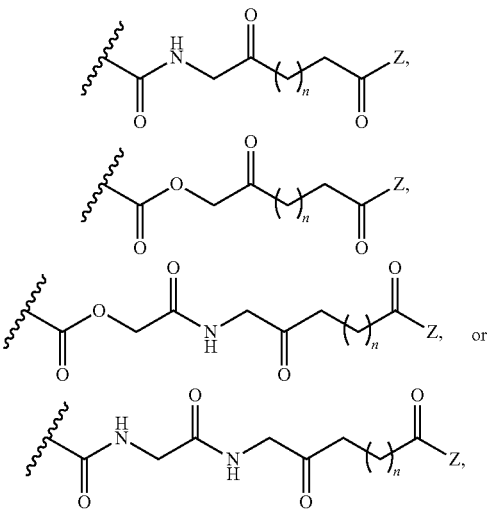

wherein Z is $OR_4$ where $R_4$ is hydrogen or $C_1$-$C_6$ alkyl, or Z is an amino acid or amino acid ester, and n is 1 or 2;

L is —$CH_2$—, —$CF_2$—, or —$C(CH_3)_2$—; and

Q is a 5- or 6-membered nitrogen-containing heteroaryl substituted by 0-2 substituents, selected from:

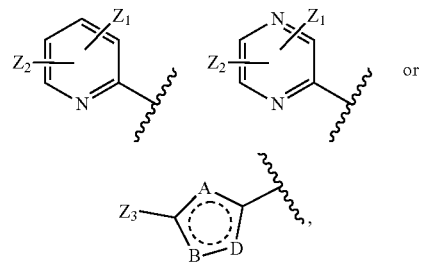

wherein A, B, and D are independently selected from O, S, N, or —CH, wherein $Z_1$, $Z_2$ are independently selected from hydrogen, deuterium, halogen, $C_1$-$C_4$ alkyl, —OH, —$OC_1$-$C_6$ alkyl, and

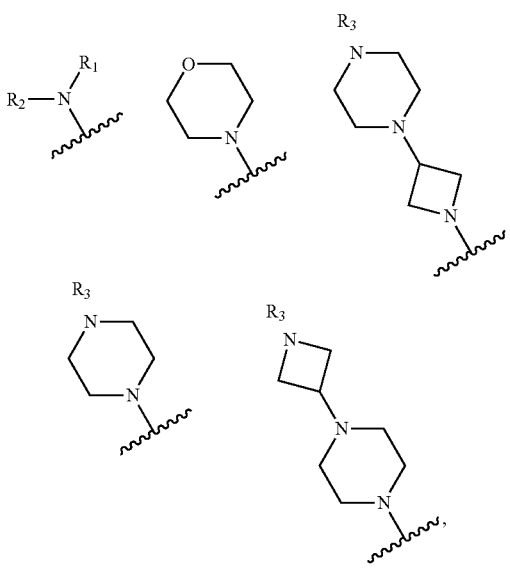

wherein R₁, R₂ and R₃ are independently selected from hydrogen, $C_1$-$C_6$ alkyl, or $C_1$-$C_6$ alkyl containing one or more —OH, and wherein $Z_3$ is selected from hydrogen, halogen, or a direct-bonded, or —NH-linked, —O$C_1$-$C_3$ alkyl linked, or —NH$C_1$-$C_3$ alkyl linked aryl, heteroaryl, cycloalkyl, heterocycloalkyl, or a nitrogen-bonded cycloalkyl, heterocycloalkyl, or —NH$C_1$-$C_4$ alkyl, —N($C_1$-$C_4$ alkyl)₂, each of which is substituted by 0-4 substituents independently selected from hydrogen, deuterium, halogen, $C_1$-$C_4$ alkyl, $C_1$-$C_3$ haloalkyl, —OH, —O$C_1$-$C_6$ alkyl, —O$C_1$-$C_6$ alkyl-C(O)NH—OH, —NH₂, —C(O)NH—$C_1$-$C_6$ alkyl-heteroaryl, —NHC(O)$C_1$-$C_6$ alkyl-C(O)NH—OH, heteroaryl, cycloalkyl, heterocycloalkyl, or a nitrogen-bonded cycloalkyl or heterocycloalkyl, —NH$C_1$-$C_4$ alkyl, or —N($C_1$-$C_4$ alkyl)₂.

2. The compound of claim 1, wherein R is a bicyclic aryl selected from naphthyl, quinolinyl, isoquinolinyl, quinoxaline, phthalazine, quinazoline, cinnoline, naphthyridine, or substituted variants thereof.

3. The compound of claim 2, wherein the compound is of the formula (Ib):

(Ib)

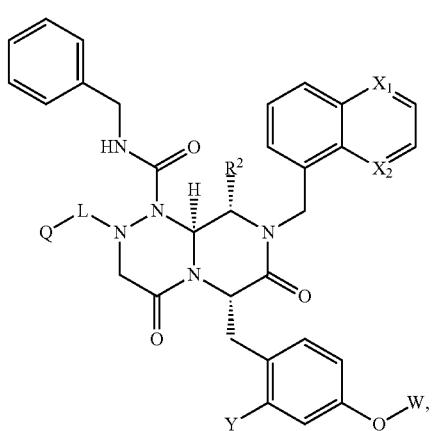

wherein $X_1$ and $X_2$ are independently selected from: N, or —CH.

4. The compound of claim 3, wherein:
L is —CH₂—;
Q is

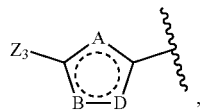

wherein A, B, and D are independently selected from O, S, N, or —CH.

5. The compound of claim 4, wherein A is —CH, B is N, and D is O ($Z_3$-isoxazole-), and wherein W is hydrogen, phosphate or phosphate salt, or X, wherein X is selected from:

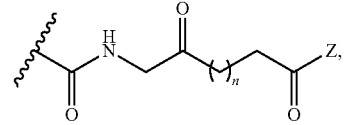

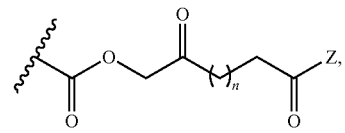

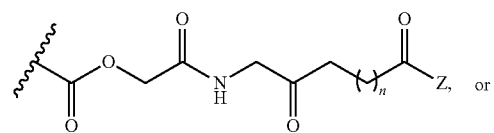

or

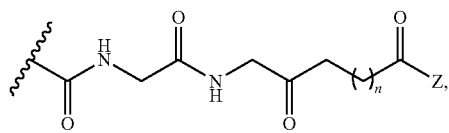

wherein Z is O$R_4$ where $R_4$ is hydrogen or $C_1$-$C_6$ alkyl, or Z is an amino acid or amino acid ester, and n is 1 or 2.

6. The compound of claim 5, wherein $Z_3$ is selected from aryl or heteroaryl, each of which is substituted by 0-4 substituents independently selected from hydrogen, deuterium, halogen, $C_1$-$C_4$ alkyl, $C_1$-$C_3$ haloalkyl, —OH, —O$C_1$-$C_6$ alkyl, —O$C_1$-$C_6$ alkyl-C(O)NH—OH, —NH₂, —C(O)NH—$C_1$-$C_6$ alkyl-heteroaryl, —NHC(O)$C_1$-$C_6$ alkyl-C(O)NH—OH, heteroaryl, cycloalkyl, heterocycloalkyl, or a nitrogen-bonded cycloalkyl or heterocycloalkyl, —NH$C_1$-$C_4$ alkyl, or —N($C_1$-$C_4$ alkyl)₂.

7. The compound of claim 6, wherein $Z_3$ is selected from aryl or heteroaryl, substituted by 0-4 substituents independently selected from hydrogen, deuterium, halogen, $C_1$-$C_4$ alkyl, $C_1$-$C_3$ haloalkyl, —OH, —O$C_1$-$C_6$ alkyl, or nitrogen-bonded heterocycloalkyl.

8. The compound of claim 7, wherein the compound is:
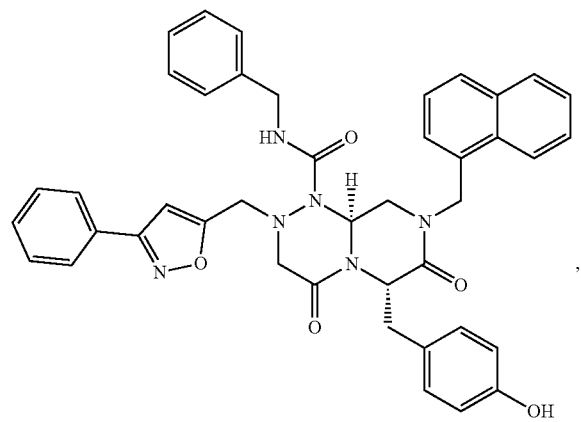
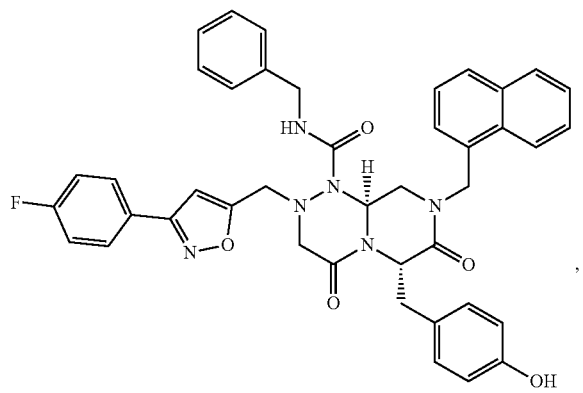
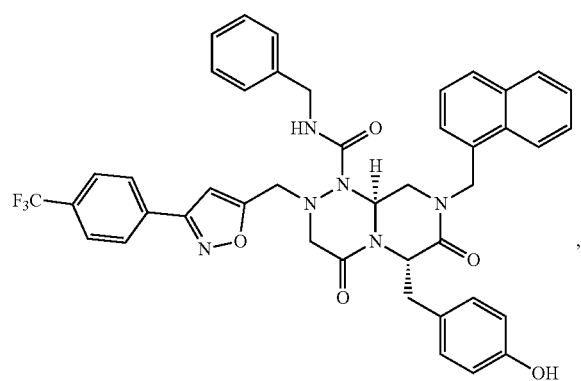
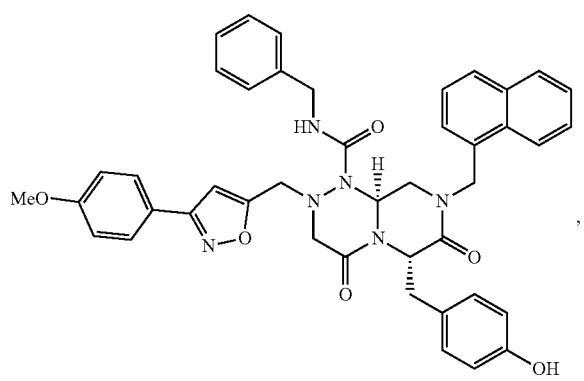
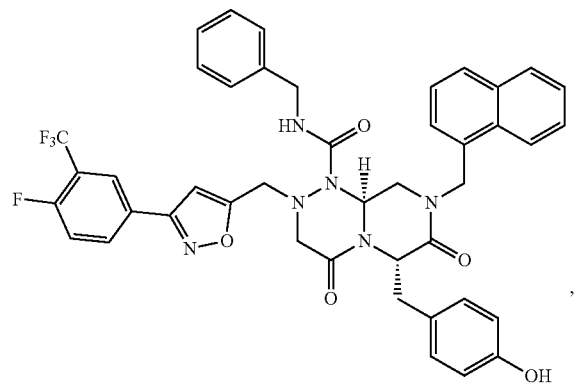
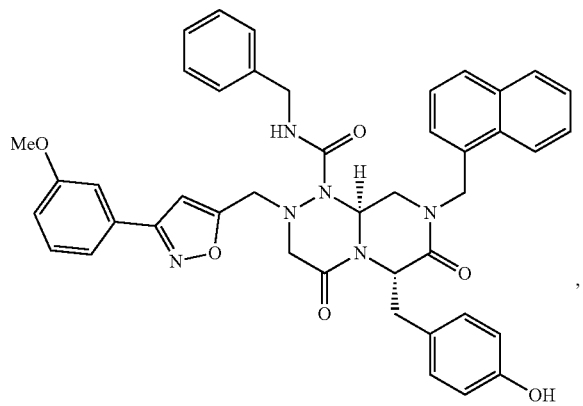
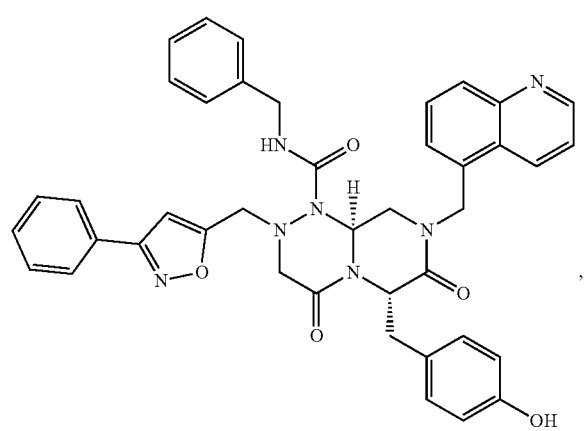
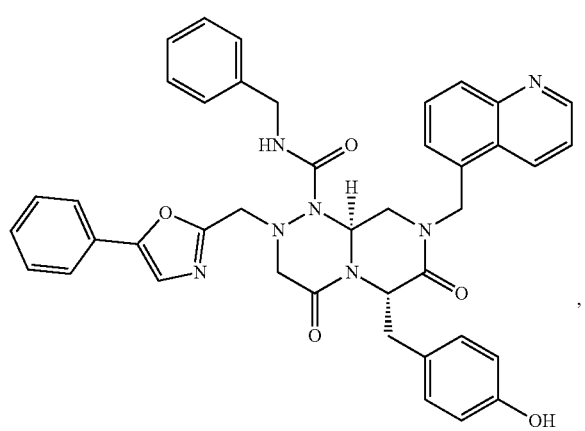

101
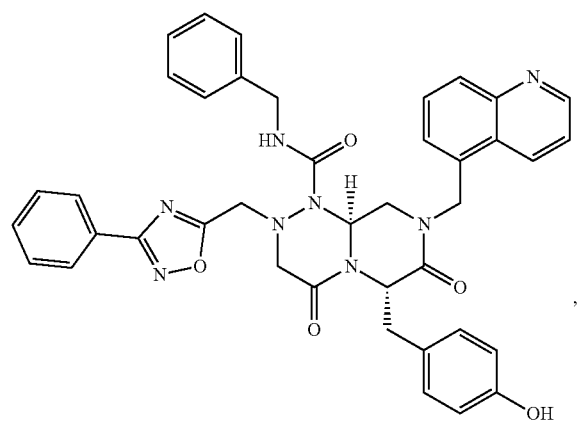
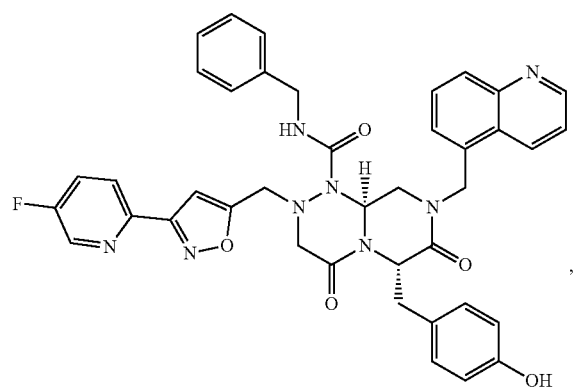
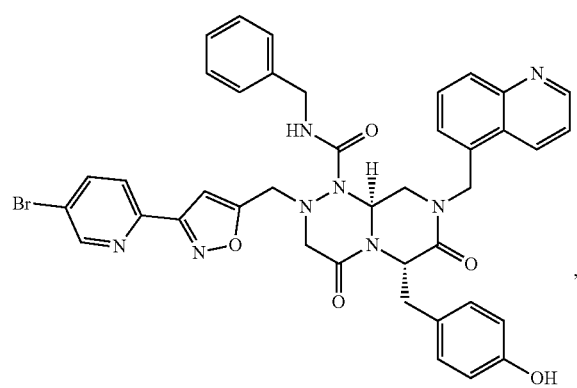
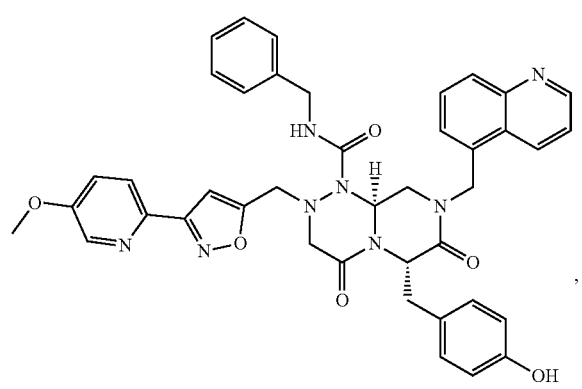
102
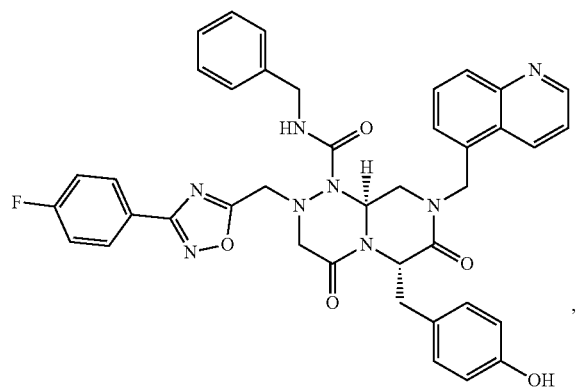
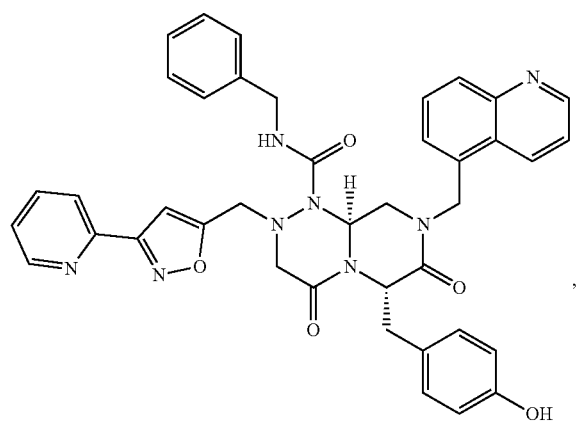
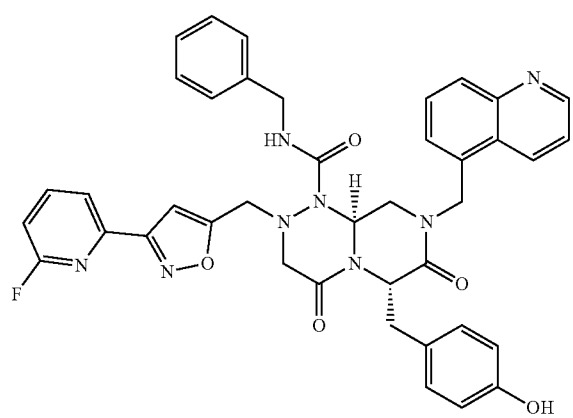
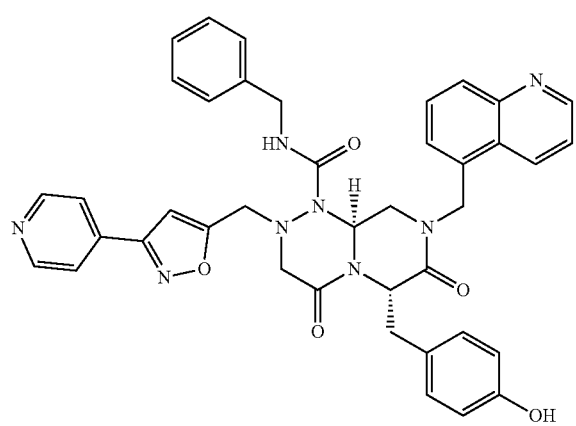

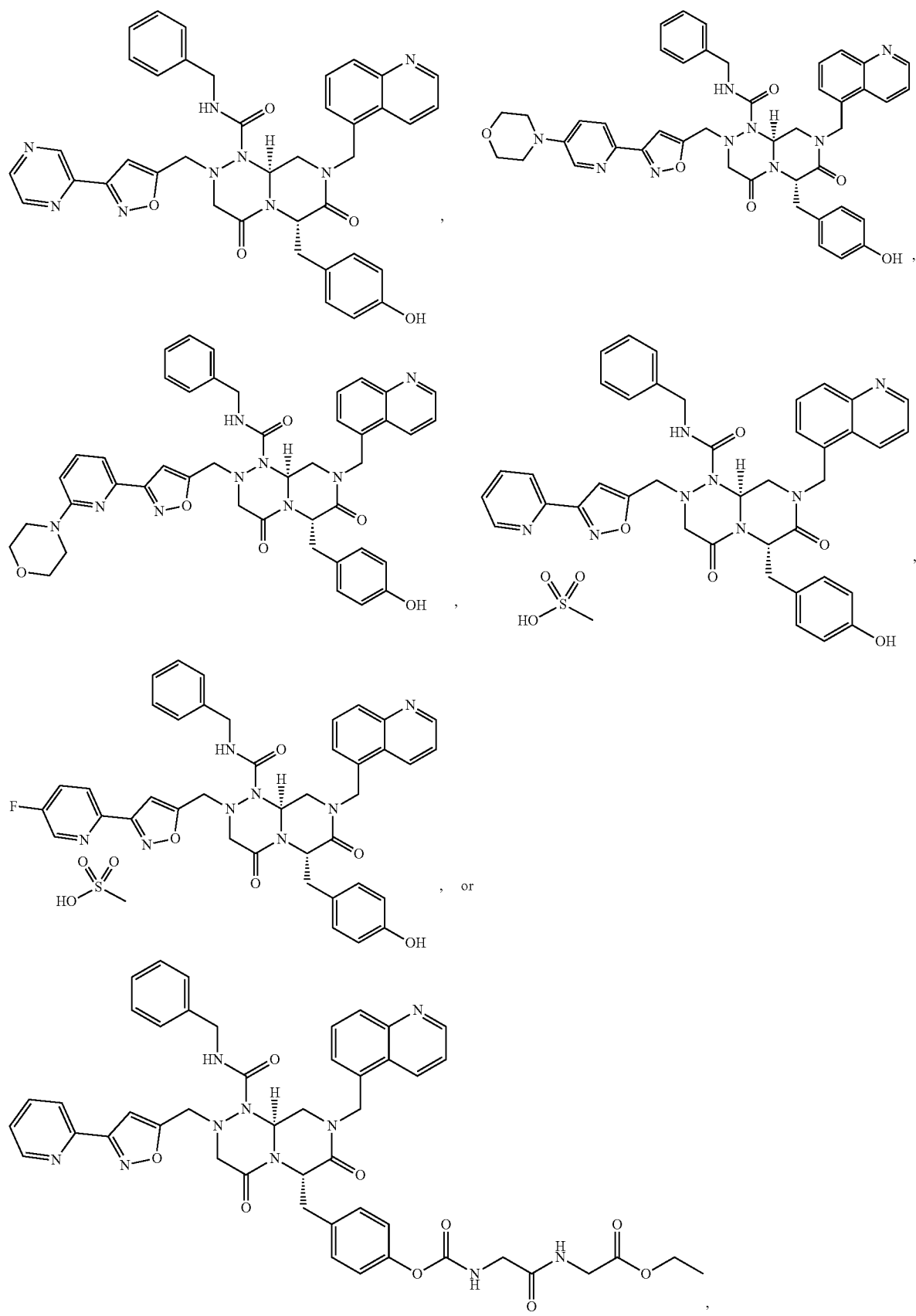

9. A compound of formula (IIa):

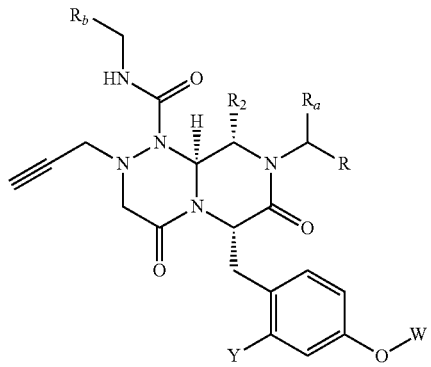

(IIa)

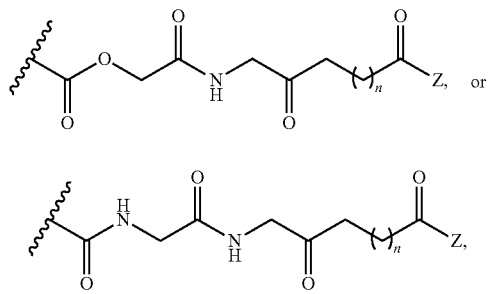

wherein Z is OR$_4$ where R$_4$ is hydrogen or C$_1$-C$_6$ alkyl, or Z is an amino acid or amino acid ester, and n is 1 or 2.

10. A compound of formula (Ia):

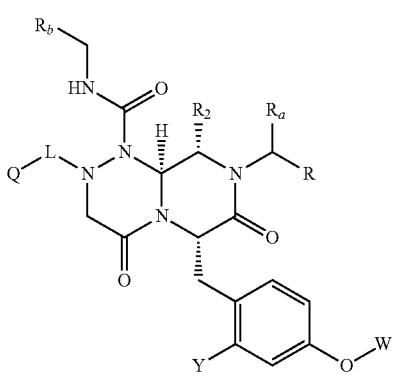

(Ia)

or a pharmaceutically acceptable salt thereof, wherein:

R$_a$ is hydrogen or —CH$_3$;

R$_b$ is a monocyclic aryl group having 5 to 7 ring members, which may have 1 to 2 heteroatoms selected from nitrogen, oxygen or sulfur, and which may have one or more substituents selected from a group consisting of halide, cyano, and lower alkyl;

R is a phenyl group; a substituted phenyl group having one or more substituents wherein the one or more substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-3}$alkoxy, nitro, carboxy, cyano, sulfuryl, and hydroxyl group; or a bicyclic aryl group, or substituted bicyclic aryl, having 8 to 11 ring members, which may have 1 to 3 heteroatoms selected from nitrogen, oxygen or sulfur, where the substituted bicyclic aryl may have one or more substituents independently selected from amino, amidino, guanidino, hydrazino, amidazonyl, C$_{1-4}$alkylamino, C$_{1-4}$dialkylamino, halogen, perfluoro C$_{1-4}$alkyl, C$_{1-3}$alkoxy, nitro, carboxy, cyano, sulfuryl, and hydroxyl group;

wherein:

R$_a$ is methyl or hydrogen;

R$_b$ is a monocyclic aryl group having 5 to 7 ring members, which may have 1 to 2 heteroatoms selected from nitrogen, oxygen or sulfur, and which may have one or more substituents selected from a group consisting of halide, cyano, and lower alkyl;

R is a phenyl group; a substituted phenyl group having one or more substituents wherein the one or more substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-3}$alkoxy, nitro, carboxy, cyano, sulfuryl, and hydroxyl group; or a bicyclic aryl group having 8 to 11 ring members, which may have 1 to 3 heteroatoms selected from nitrogen, oxygen or sulfur;

R$^2$ is hydrogen, or —CH$_3$;

Y is selected from: hydrogen, deuterium, or halogen;

W is X, wherein X is selected from: an alkyl acid or fatty acid,

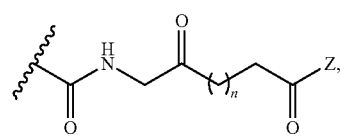

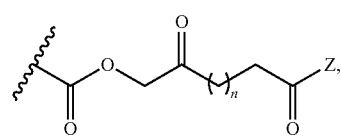

R² is hydrogen, or —CH₃;
Y is selected from: hydrogen, deuterium, or halogen;
W is an ester of an alkyl acid or of a fatty acid;
L is —CH₂—, —CF₂—, or —C(CH₃)₂—; and
Q is a 5- or 6-membered nitrogen-containing heteroaryl substituted by 0-2 substituents, selected from:

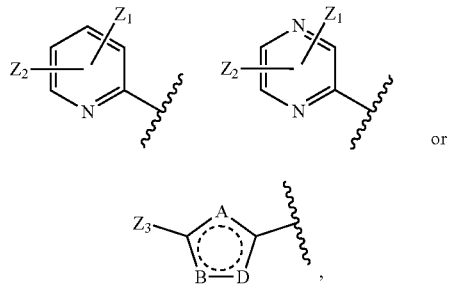

wherein A, B, and D are independently selected from O, S, N, or —CH, wherein Z₁, Z₂ are independently selected from hydrogen, deuterium, halogen, C₁-C₄ alkyl, —OH, —OC₁-C₆ alkyl, and

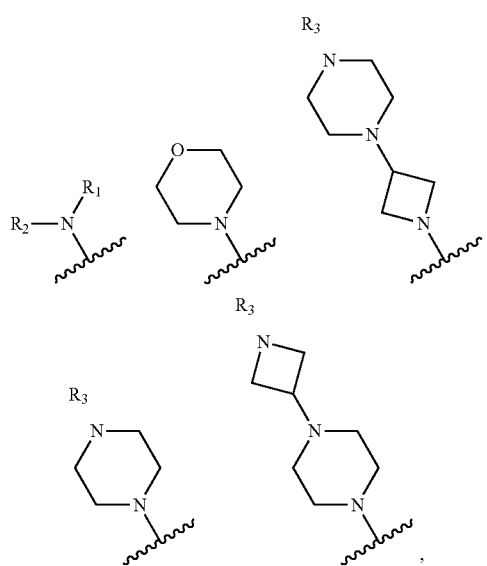

wherein R₁, R₂ and R₃ are independently selected from hydrogen, C₁-C₆ alkyl, or C₁-C₆ alkyl containing one or more —OH, and wherein Z₃ is selected from hydrogen, halogen, or a direct-bonded, or —NH-linked, —OC₁-C₃ alkyl linked, or —NHC₁-C₃ alkyl linked aryl, heteroaryl, cycloalkyl, heterocycloalkyl, or a nitrogen-bonded cycloalkyl, heterocycloalkyl, or —NHC₁-C₄ alkyl, —N(C₁-C₄ alkyl)₂, each of which is substituted by 0-4 substituents independently selected from hydrogen, deuterium, halogen, C₁-C₄ alkyl, C₁-C₃ haloalkyl, —OH, —OC₁-C₆ alkyl, —OC₁-C₆ alkyl-C(O)NH—OH, —NH₂, —C(O)NH—C₁-C₆ alkyl-heteroaryl, —NHC(O)C₁-C₆ alkyl-C(O)NH—OH, heteroaryl, cycloalkyl, heterocycloalkyl, or a nitrogen-bonded cycloalkyl or heterocycloalkyl, —NHC₁-C₄ alkyl, or —N(C₁-C₄ alkyl)₂.

11. The compound of claim 10, wherein the ester of the alkyl acid or of the fatty acid is selected from:

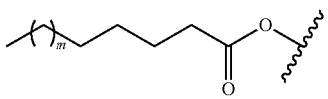

wherein m is 1 to 14,

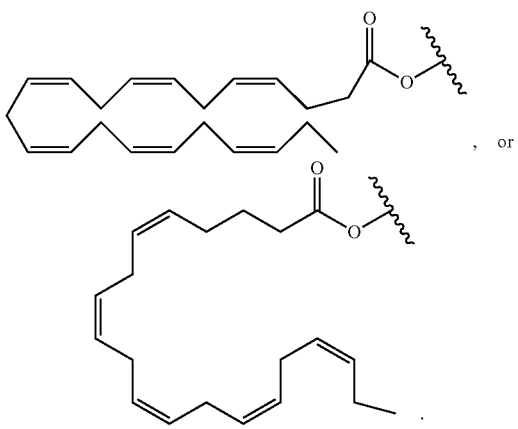

, or

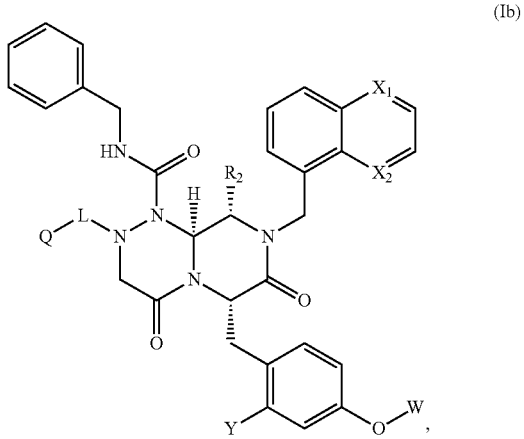

.

12. The compound of claim 10, wherein R is a bicyclic aryl selected from naphthyl, quinolinyl, isoquinolinyl, quinoxaline, phthalazine, quinazoline, cinnoline, naphthyridine, or substituted variants thereof.

13. The compound of claim 12, wherein the compound is of the formula (Ib):

(Ib)

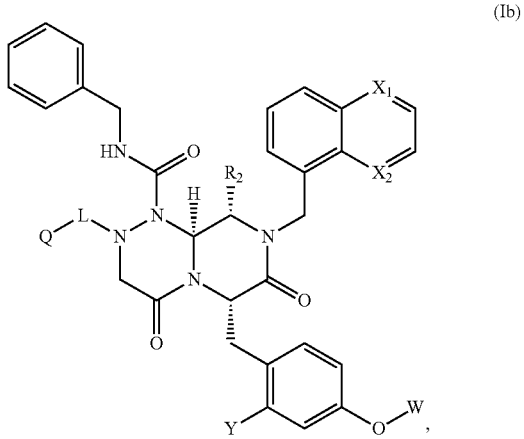

wherein X₁ and X₂ are independently selected from: N, or —CH.

14. The compound of claim 13, wherein:
L is —CH₂—;
Q is

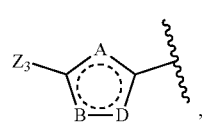

, wherein A, B, and D are independently selected from O, S, N, or —CH.

15. The compound of claim 14, wherein A is —CH, B is N, and D is O ($Z_3$-isoxazole-).

16. The compound of claim 15, wherein $Z_3$ is selected from aryl or heteroaryl, each of which is substituted by 0-4 substituents independently selected from hydrogen, deuterium, halogen, $C_1$-$C_4$ alkyl, $C_1$-$C_3$ haloalkyl, —OH, —O$C_1$-$C_6$ alkyl, —O$C_1$-$C_6$ alkyl-C(O)NH—OH, —$NH_2$, —C(O)NH—$C_1$-$C_6$ alkyl-heteroaryl, —NHC(O)$C_1$-$C_6$ alkyl-C(O)NH—OH, heteroaryl, cycloalkyl, heterocycloalkyl, or a nitrogen-bonded cycloalkyl or heterocycloalkyl, —NH$C_1$-$C_4$ alkyl, or —N($C_1$-$C_4$ alkyl)$_2$.

17. The compound of claim 16, wherein $Z_3$ is selected from aryl or heteroaryl, substituted by 0-4 substituents independently selected from hydrogen, deuterium, halogen, $C_1$-$C_4$ alkyl, $C_1$-$C_3$ haloalkyl, —OH, —O$C_1$-$C_6$ alkyl, or nitrogen-bonded heterocycloalkyl.

18. The compound of claim 17, wherein the compound is:

19. The compound of claim 1, wherein the pharmaceutically acceptable salt is a p-toluenesulfonate.

20. A composition or pharmaceutical composition comprising the compound of any one of claim 1, claims 2-8, or claim 19 and a pharmaceutically acceptable carrier.

21. A composition or pharmaceutical composition comprising the compound of any one of claims 10 to 18, and a pharmaceutically acceptable carrier.

22. A method of treating a disease or disorder, comprising administering to a patient or a warm-blooded mammal, having a disease or disorder mediated by CREB binding protein (CBP)/β-catenin signaling, a therapeutically effective amount of a compound, or of a composition or pharmaceutical composition comprising same wherein the dis

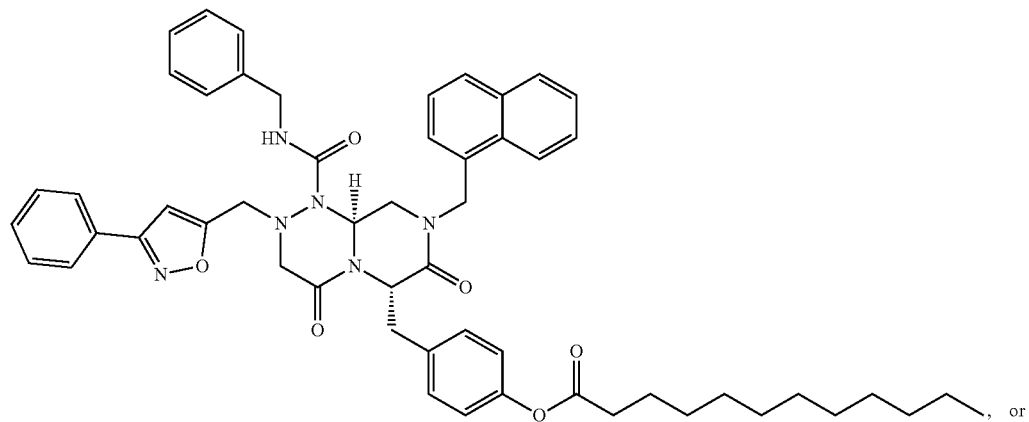

, or

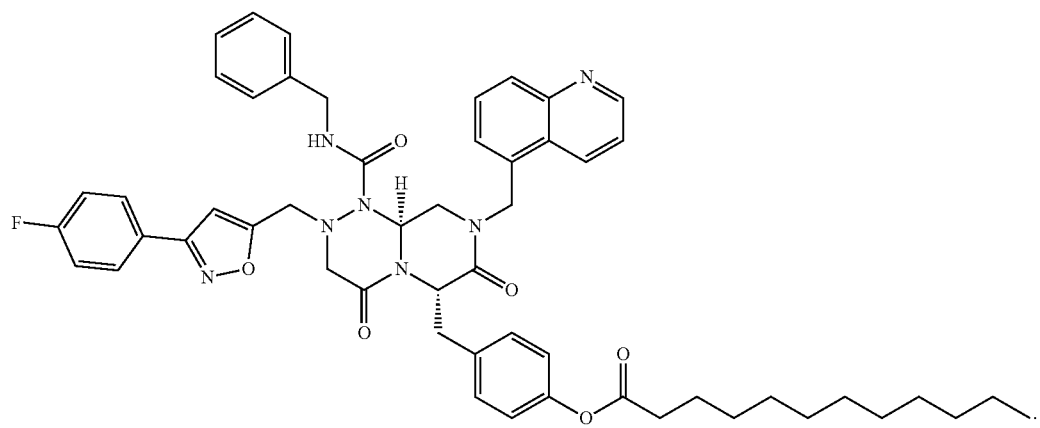

.

ease or disorder is one or more of fibrosis, metabolic disease, and skin conditions, and wherein the compound is of formula (Ia):

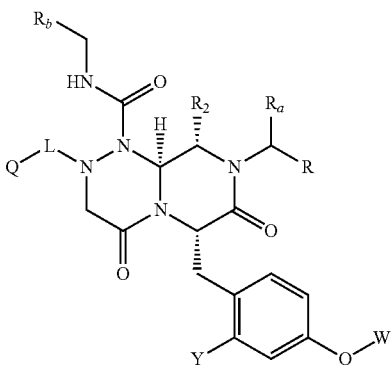

(Ia)

or a pharmaceutically acceptable salt thereof, wherein:
  $R_a$ is hydrogen or —CH$_3$;
  $R_b$ is a monocyclic aryl group having 5 to 7 ring members, which may have 1 to 2 heteroatoms selected from nitrogen, oxygen or sulfur, and which may have one or more substituents selected from a group consisting of halide, cyano, and lower alkyl;
  R is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$ alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group; or a bicyclic aryl group, or substituted bicyclic aryl, having 8 to 11 ring members, which may have 1 to 3 heteroatoms selected from nitrogen, oxygen or sulfur, where the substituted bicyclic aryl may have one or more substituents independently selected from amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group;
  $R^2$ is hydrogen, or —CH$_3$;
  Y is selected from: hydrogen, deuterium, or halogen;
  W is hydrogen, phosphate or phosphate salt, or X, wherein X is selected from:

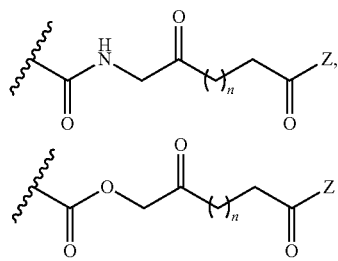

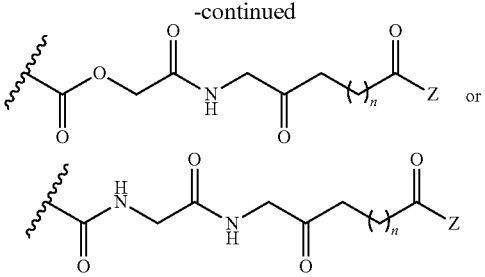

wherein Z is OR$_4$ where R$_4$ is hydrogen or C$_1$-C$_6$ alkyl, or Z is an amino acid or amino acid ester, and n is 1 or 2;
  L is —CH$_2$—, —CF$_2$—, or —C(CH$_3$)$_2$—; and
  Q is a 5- or 6-membered nitrogen-containing heteroaryl substituted by 0-2 substituents, selected from:

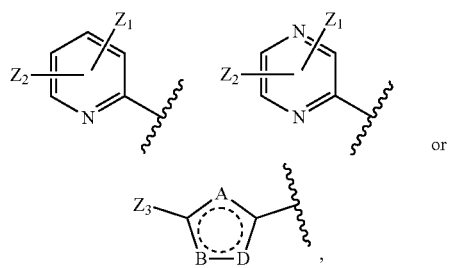

wherein A, B, and D are independently selected from O, S, N, or —CH, wherein Z$_1$, Z$_2$ are independently selected from hydrogen, deuterium, halogen, C$_1$-C$_4$ alkyl, —OH, —OC$_1$-C$_6$ alkyl, and

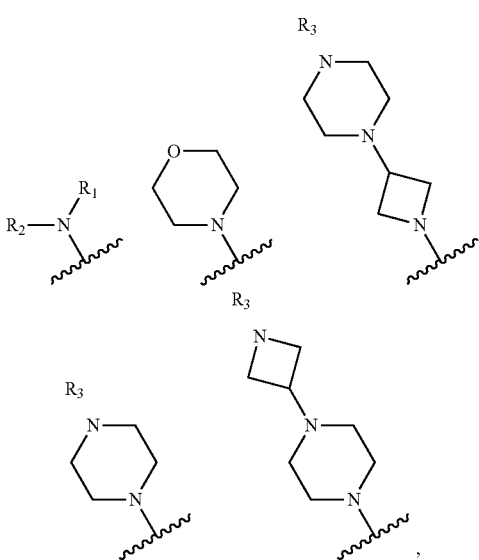

wherein R$_1$, R$_2$ and R$_3$ are independently selected from hydrogen, C$_1$-C$_6$ alkyl, or C$_1$-C$_6$ alkyl containing one or more —OH, and wherein Z$_3$ is selected from hydrogen, halogen, or a direct-bonded, or —NH-linked, —OC$_1$-C$_3$ alkyl linked, or —NHC$_1$-C$_3$ alkyl linked aryl, heteroaryl, cycloalkyl, heterocycloalkyl, or a nitrogen-bonded cycloalkyl, heterocycloalkyl, or —NHC$_1$-C$_4$ alkyl, —N(C$_1$-C$_4$ alkyl)$_2$, each of which is substituted by 0-4 substituents independently selected from hydrogen, deuterium, halogen, $C_1$-$C_4$ alkyl, $C_1$-$C_3$ haloalkyl, —OH, —O$C_1$-$C_6$ alkyl, —O$C_1$-$C_6$ alkyl-C(O)NH—OH, —NH$_2$, —C(O)NH—$C_1$-$C_6$ alkyl-heteroaryl, —NHC(O)$C_1$-$C_6$ alkyl-C(O)NH—OH, heteroaryl, cycloalkyl, heterocycloalkyl, or a nitrogen-bonded cycloalkyl or heterocycloalkyl, —NH$C_1$-$C_4$ alkyl, or —N($C_1$-$C_4$ alkyl)$_2$.

23. The method of claim 22, wherein, in the compound, W is X, wherein X is selected from:

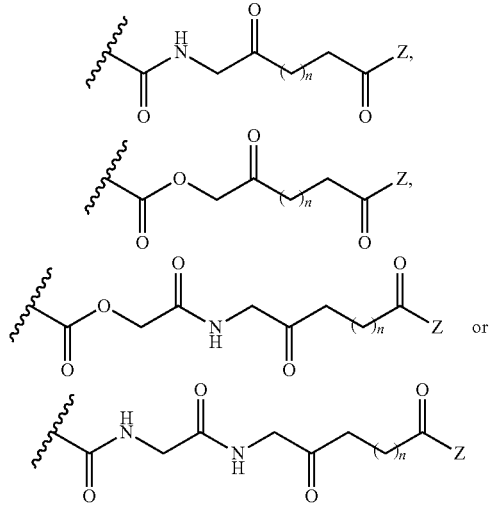

wherein Z is OR$_4$ where R$_4$ is hydrogen or $C_1$-$C_6$ alkyl, or Z is an amino acid or amino acid ester and n is 1 or 2.

24. The method of claim 22, wherein, in the compound, X is

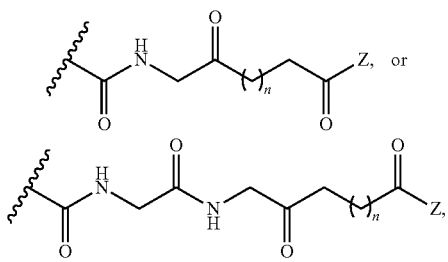

wherein Z is OR$_4$ where R$_4$ is a hydrogen or $C_1$-$C_6$ alkyl, or Z is an amino acid or amino acid ester and n is 1 or 2.

25. The method of claim 22, wherein the metabolic disorder comprises one or more of diabetes and/or fatty liver disease.

26. The method of claim 25, wherein the fatty liver disease comprises one or more of alcoholic hepatic steatosis (ALD), non-alcoholic hepatic steatosis (NAFLD), and/or non-alcoholic steatohepatitis (NASH).

27. The method of claim 22, wherein the fibrosis is fibrosis of the lung, liver, kidney, heart, endometrium, skin or systemic fibrosis.

28. The method of claim 27, wherein the fibrosis comprises fibrosis in a SARS-CoV-2 (COVID-19) patient tissue.

29. The method of claim 22, wherein the skin condition comprises one or more of atopic dermatitis, psoriasis, acne, fibrosis, wounding, scarring, burns, sun or U.V. damage, diabetic ulceration, chronic ulceration, and/or alopecia.

30. The method of claim 29, wherein administration comprises topical or transdermal administration.

31. A cosmetic method for treating a skin condition, comprising topically administering to a patient or a warm-blooded mammal, having a skin condition, a cosmeceutically effective amount of a compound, or of a composition or pharmaceutical composition comprising same, and wherein the compound is of formula (Ia):

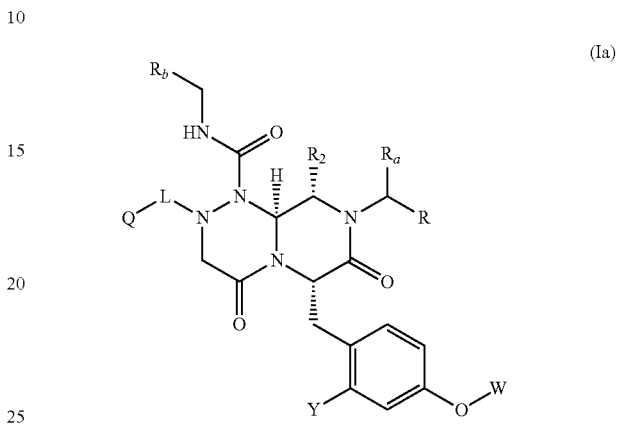

(Ia)

or a pharmaceutically acceptable salt thereof, wherein:
R$_a$ is hydrogen or —CH$_3$;
R$_b$ is a monocyclic aryl group having 5 to 7 ring members, which may have 1 to 2 heteroatoms selected from nitrogen, oxygen or sulfur, and which may have one or more substituents selected from a group consisting of halide, cyano, and lower alkyl;
R is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group; or a bicyclic aryl group, or substituted bicyclic aryl, having 8 to 11 ring members, which may have 1 to 3 heteroatoms selected from nitrogen, oxygen or sulfur, where the substituted bicyclic aryl may have one or more substituents independently selected from amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group;
R$^2$ is hydrogen, or —CH$_3$;
Y is selected from: hydrogen, deuterium, or halogen;
W is hydrogen, phosphate or phosphate salt, or X, wherein X is selected from:

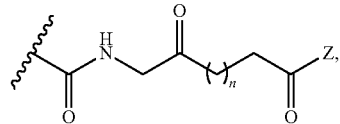

-continued

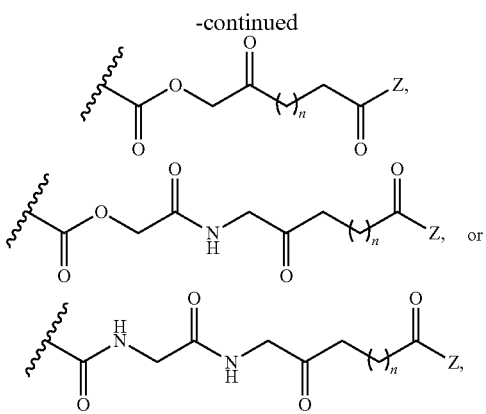

wherein Z is OR$_4$ where R$_4$ is hydrogen or C$_1$-C$_6$ alkyl, or Z is an amino acid or amino acid ester, and n is 1 or 2;
L is —CH$_2$—, —CF$_2$—, or —C(CH$_3$)$_2$—; and
Q is a 5- or 6-membered nitrogen-containing heteroaryl substituted by 0-2 substituents, selected from:

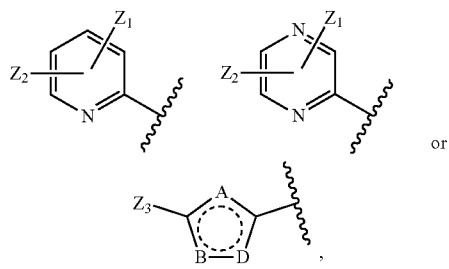

wherein A, B, and D are independently selected from O, S, N, or —CH, wherein Z$_1$, Z$_2$ are independently selected from hydrogen, deuterium, halogen, C$_1$-C$_4$ alkyl, —OH, —OC$_1$-C$_6$ alkyl, and

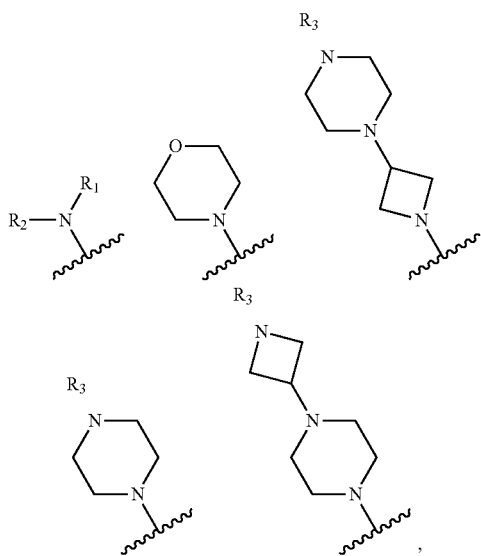

wherein R$_1$, R$_2$ and R$_3$ are independently selected from hydrogen, C$_1$-C$_6$ alkyl, or C$_1$-C$_6$ alkyl containing one or more —OH, and wherein Z$_3$ is selected from hydrogen, halogen, or a direct-bonded, or —NH-linked, —OC$_1$-C$_3$ alkyl linked, or —NHC$_1$-C$_3$ alkyl linked aryl, heteroaryl, cycloalkyl, heterocycloalkyl, or a nitrogen-bonded cycloalkyl, heterocycloalkyl, or —NHC$_1$-C$_4$ alkyl, —N(C$_1$-C$_4$ alkyl)$_2$, each of which is substituted by 0-4 substituents independently selected from hydrogen, deuterium, halogen, C$_1$-C$_4$ alkyl, C$_1$-C$_3$ haloalkyl, —OH, —OC$_1$-C$_6$ alkyl, —OC$_1$-C$_6$ alkyl-C(O)NH—OH, —NH$_2$, —C(O)NH—C$_1$-C$_6$ alkyl-heteroaryl, —NHC(O)C$_1$-C$_6$ alkyl-C(O)NH—OH, heteroaryl, cycloalkyl, heterocycloalkyl, or a nitrogen-bonded cycloalkyl or heterocycloalkyl, —NHC$_1$-C$_4$ alkyl, or —N(C$_1$-C$_4$ alkyl)$_2$.

32. The method of claim 31, wherein the skin condition comprises one or more aging skin conditions selected from wrinkles, hyperpigmentation, redness, rosacea, dryness, cracking, loss of vibrance, loss of elasticity, thinning, loss of vibrance, scarring, acne, sun damage, hair loss, loss of hair coloration, reduced cuticle growth, reduced nail growth.

33. A method of treating a disease or disorder, comprising administering to a patient or a warm-blooded mammal, having a disease or disorder mediated by CREB binding protein (CBP)/β-catenin signaling, a therapeutically effective amount of a compound, or of a composition or pharmaceutical composition comprising same, wherein the disease or disorder is one or more skin conditions selected from atopic dermatitis, psoriasis, acne, fibrosis, wounding, scarring, burns, sun or U.V. damage, diabetic ulceration, chronic ulcerations and alopecia, and wherein the compound is of formula (Ia):

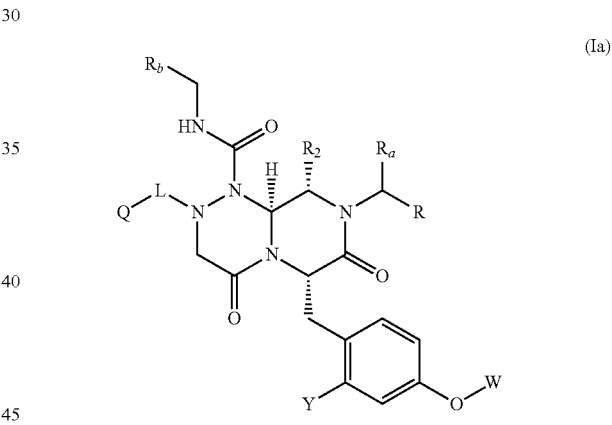

(Ia)

or a pharmaceutically acceptable salt thereof, wherein:
R$_a$ is hydrogen or —CH$_3$;
R$_b$ is a monocyclic aryl group having 5 to 7 ring members, which may have 1 to 2 heteroatoms selected from nitrogen, oxygen or sulfur, and which may have one or more substituents selected from a group consisting of halide, cyano, and lower alkyl;
R is a phenyl group; a substituted phenyl group having one or more substituents wherein the one or more substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$ alkyl, C$_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-3}$alkoxy, nitro, carboxy, cyano, sulfuryl, and hydroxyl group; or a bicyclic aryl group, or substituted bicyclic aryl, having 8 to 11 ring members, which may have 1 to 3 heteroatoms selected from nitrogen, oxygen or sulfur, where the substituted bicyclic aryl may have one or more substituents independently selected from amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group;

$R^2$ is hydrogen, or —$CH_3$;

Y is selected from: hydrogen, deuterium, or halogen;

W is an ester of an alkyl acid or of a fatty acid;

L is —$CH_2$—, —$CF_2$—, or —$C(CH_3)_2$—; and

Q is a 5- or 6-membered nitrogen-containing heteroaryl substituted by 0-2 substituents, selected from:

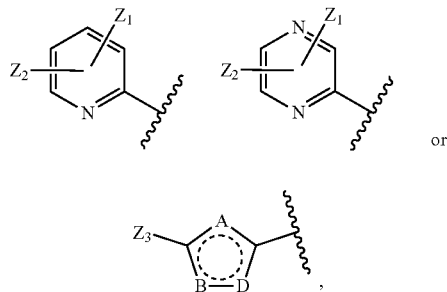

wherein A, B, and D are independently selected from O, S, N, or —CH, wherein $Z_1$, $Z_2$ are independently selected from hydrogen, deuterium, halogen, $C_1$-$C_4$ alkyl, —OH, —$OC_1$-$C_6$ alkyl, and

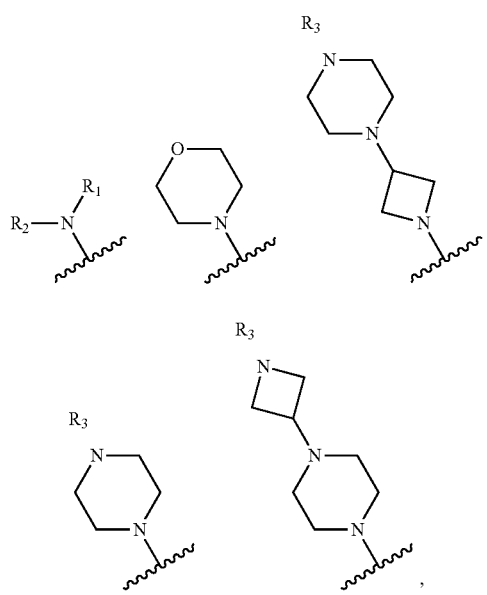

wherein $R_1$, $R_2$ and $R_3$ are independently selected from hydrogen, $C_1$-$C_6$ alkyl, or $C_1$-$C_6$ alkyl containing one or more —OH, and wherein $Z_3$ is selected from hydrogen, halogen, or a direct-bonded, or —NH-linked, —$OC_1$-$C_3$ alkyl linked, or —$NHC_1$-$C_3$ alkyl linked aryl, heteroaryl, cycloalkyl, heterocycloalkyl, or a nitrogen-bonded cycloalkyl, heterocycloalkyl, or —$NHC_1$-$C_4$ alkyl, —$N(C_1$-$C_4$ alkyl$)_2$, each of which is substituted by 0-4 substituents independently selected from hydrogen, deuterium, halogen, $C_1$-$C_4$ alkyl, $C_1$-$C_3$ haloalkyl, —OH, —$OC_1$-$C_6$ alkyl, —$OC_1$-$C_6$ alkyl-C(O)NH—OH, —$NH_2$, —C(O)NH—$C_1$-$C_6$ alkyl-heteroaryl, —NHC(O)$C_1$-$C_6$ alkyl-C(O)NH—OH, heteroaryl, cycloalkyl, heterocycloalkyl, or a nitrogen-bonded cycloalkyl or heterocycloalkyl, —$NHC_1$-$C_4$ alkyl, or —$N(C_1$-$C_4$ alkyl$)_2$.

34. The method of claim 33, wherein the fibrosis is fibrosis of the skin.

35. The method of claim 33, wherein administration comprises topical or transdermal administration.

36. A cosmetic method for treating a skin condition, comprising topically administering to a patient or a warm-blooded mammal, having a skin condition, a cosmeceutically effective amount of a compound, or of a composition or pharmaceutical composition comprising same, and wherein the compound is of formula (Ia):

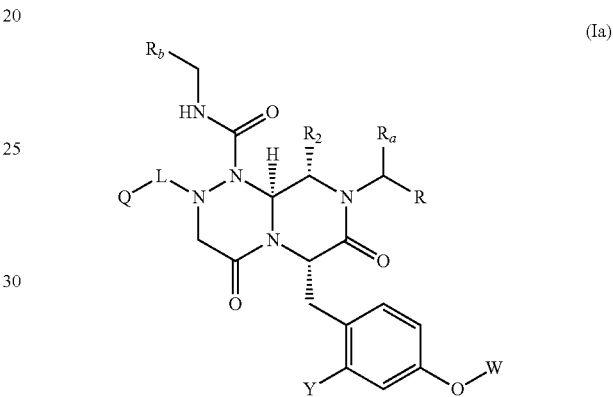

(Ia)

or a pharmaceutically acceptable salt thereof, wherein:

$R_a$ is hydrogen or —$CH_3$;

$R_b$ is a monocyclic aryl group having 5 to 7 ring members, which may have 1 to 2 heteroatoms selected from nitrogen, oxygen or sulfur, and which may have one or more substituents selected from a group consisting of halide, cyano, and lower alkyl;

R is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$ alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group; or a bicyclic aryl group, or substituted bicyclic aryl, having 8 to 11 ring members, which may have 1 to 3 heteroatoms selected from nitrogen, oxygen or sulfur, where the substituted bicyclic aryl may have one or more substituents independently selected from amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group;

R² is hydrogen, or —CH₃;
Y is selected from: hydrogen, deuterium, or halogen;
W is an ester of an alkyl acid or of a fatty acid;
L is —CH₂—, —CF₂—, or —C(CH₃)₂—; and
Q is a 5- or 6-membered nitrogen-containing heteroaryl substituted by 0-2 substituents, selected from:

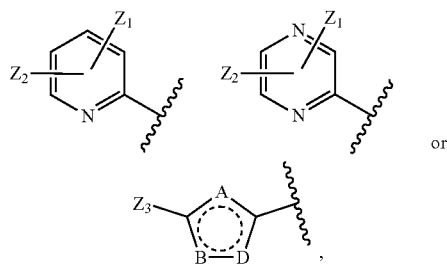

wherein A, B, and D are independently selected from O, S, N, or —CH, wherein Z₁, Z₂ are independently selected from hydrogen, deuterium, halogen, C₁-C₄ alkyl, —OH, —OC₁-C₆ alkyl, and

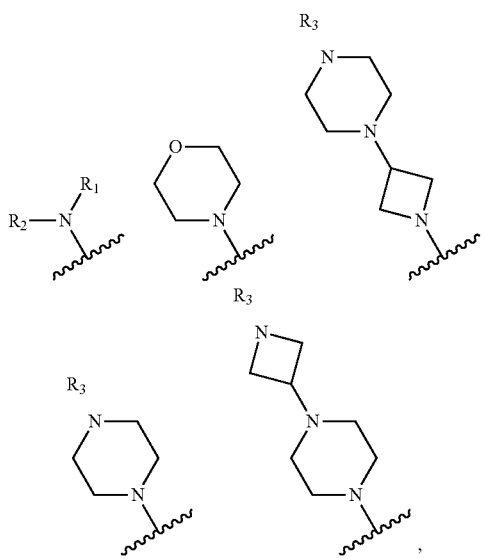

wherein R₁, R₂ and R₃ are independently selected from hydrogen, C₁-C₆ alkyl, or C₁-C₆ alkyl containing one or more —OH, and wherein Z₃ is selected from hydrogen, halogen, or a direct-bonded, or —NH-linked, —OC₁-C₃ alkyl linked, or —NHC₁-C₃ alkyl linked aryl, heteroaryl, cycloalkyl, heterocycloalkyl, or a nitrogen-bonded cycloalkyl, heterocycloalkyl, or —NHC₁-C₄ alkyl, —N(C₁-C₄ alkyl)₂, each of which is substituted by 0-4 substituents independently selected from hydrogen, deuterium, halogen, C₁-C₄ alkyl, C₁-C₃ haloalkyl, —OH, —OC₁-C₆ alkyl, —OC₁-C₆ alkyl-C(O)NH—OH, —NH₂, —C(O)NH—C₁-C₆ alkyl-heteroaryl, —NHC(O)C₁-C₆ alkyl-C(O)NH—OH, heteroaryl, cycloalkyl, heterocycloalkyl, or a nitrogen-bonded cycloalkyl or heterocycloalkyl, —NHC₁-C₄ alkyl, or —N(C₁-C₄ alkyl)₂.

37. The method of claim 36, wherein the skin condition comprises one or more aging skin conditions selected from wrinkles, hyperpigmentation, redness, rosacea, dryness, cracking, loss of vibrance, loss of elasticity, thinning, loss of vibrance, scarring, acne, sun damage, hair loss, loss of hair coloration, reduced cuticle growth, reduced nail growth.

38. The method of claim 22 or claim 31, wherein R is a bicyclic aryl selected from naphthyl, quinolinyl, isoquinolinyl, quinoxaline, phthalazine, quinazoline, cinnoline, naphthyridine, or substituted variants thereof.

39. The method of claim 38, wherein the compound is of the formula (Ib):

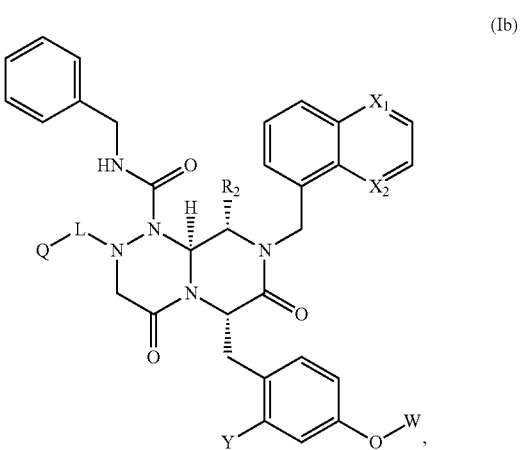

(Ib)

wherein X₁ and X₂ are independently selected from: N, or —CH.

40. The method of claim 39, wherein:
L is —CH₂—;
Q is

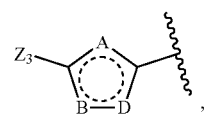

wherein A, B, and D are independently selected from O, S, N, or —CH.

41. The method of claim 40, wherein A is —CH, B is N, and D is O (Z₃-isoxazole-), and wherein W is hydrogen, phosphate or phosphate salt, or X, wherein X is selected from:

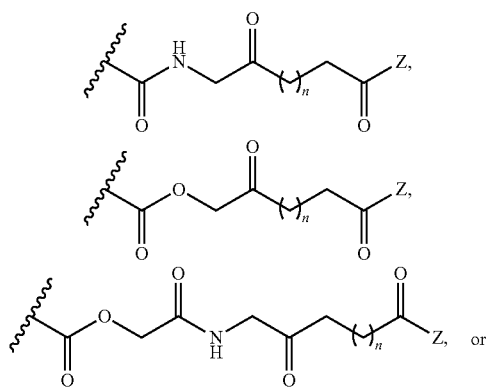

121

-continued

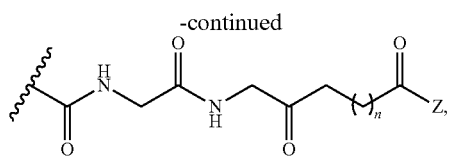

wherein Z is OR$_4$ where R$_4$ is hydrogen or C$_1$-C$_6$ alkyl, or Z is an amino acid or amino acid ester, and n is 1 or 2.

42. The method of claim 41, wherein Z$_3$ is selected from aryl or heteroaryl, each of which is substituted by 0-4 substituents independently selected from hydrogen, deuterium, halogen, C$_1$-C$_4$ alkyl, C$_1$-C$_3$ haloalkyl, —OH, —OC$_1$-C$_6$ alkyl, —OC$_1$-C$_6$ alkyl-C(O)NH—OH, —NH$_2$, —C(O)NH—C$_1$-C$_6$ alkyl-heteroaryl, —NHC(O)C$_1$-C$_6$ alkyl-C(O)NH—OH, heteroaryl, cycloalkyl, heterocycloalkyl, or a nitrogen-bonded cycloalkyl or heterocycloalkyl, —NHC$_1$-C$_4$ alkyl, or —N(C$_1$-C$_4$ alkyl)$_2$.

43. The method of claim 42, wherein Z$_3$ is selected from aryl or heteroaryl, substituted by 0-4 substituents independently selected from hydrogen, deuterium, halogen, C$_1$-C$_4$ alkyl, C$_1$-C$_3$ haloalkyl, —OH, —OC$_1$-C$_6$ alkyl, or nitrogen-bonded heterocycloalkyl.

44. The method of claim 43, wherein the compound is:

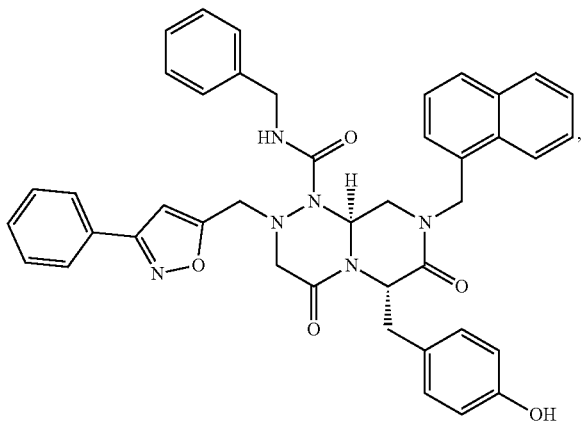

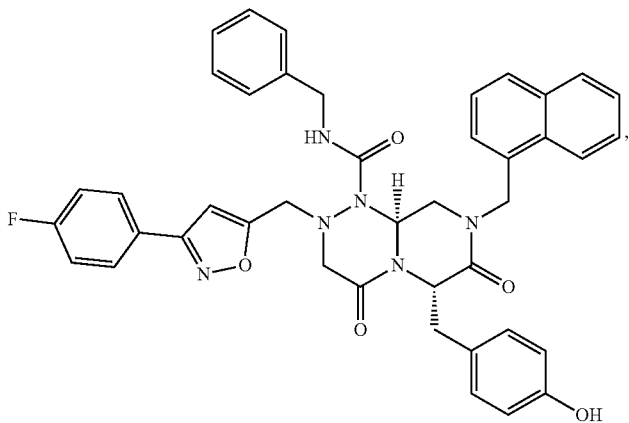

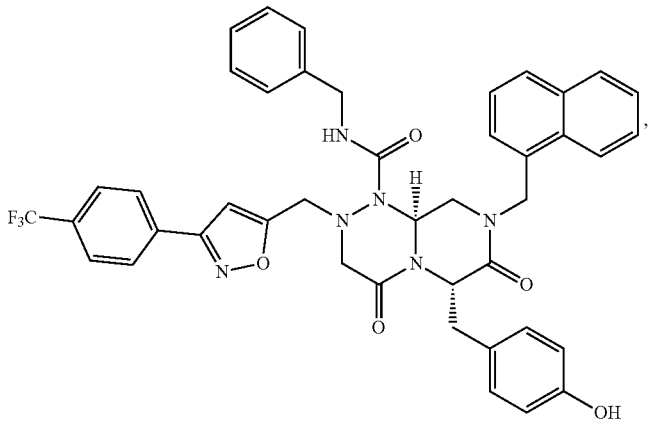

123                                                                          124
-continued
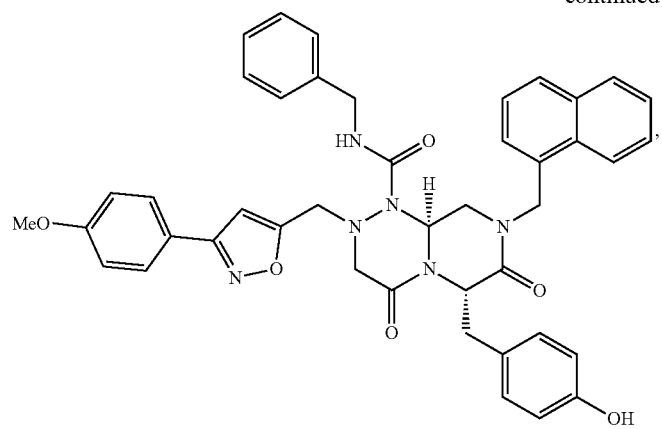
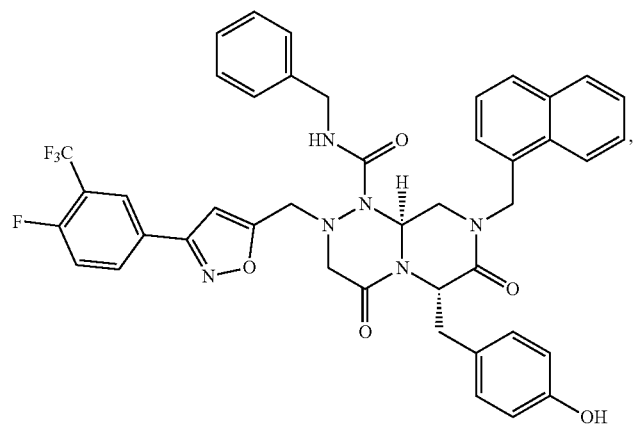
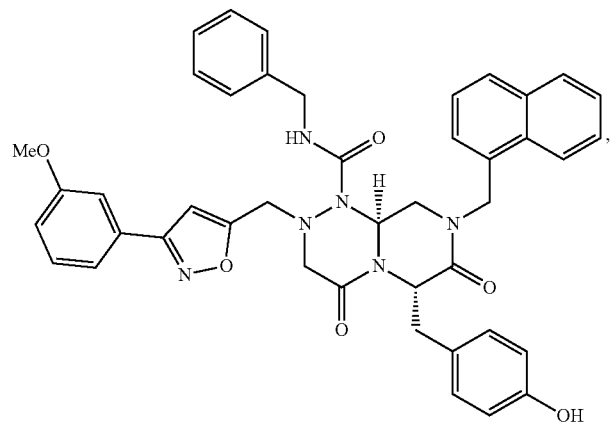
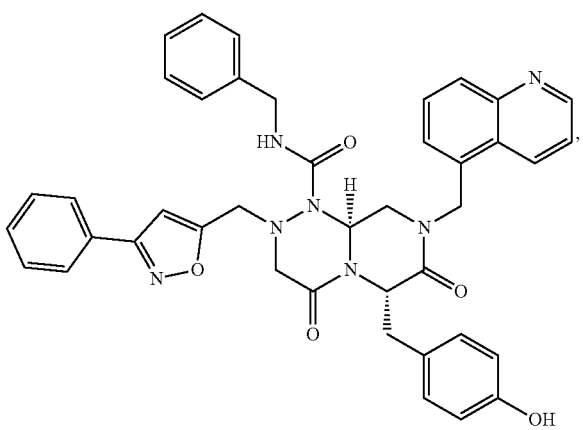
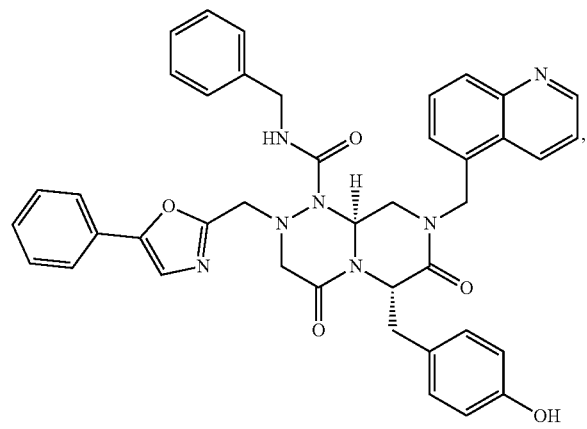
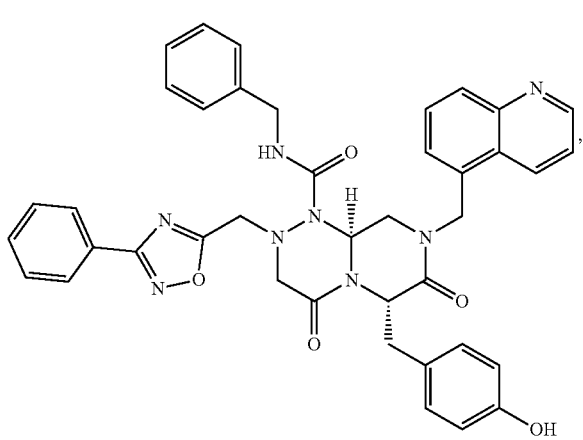

125
126
-continued
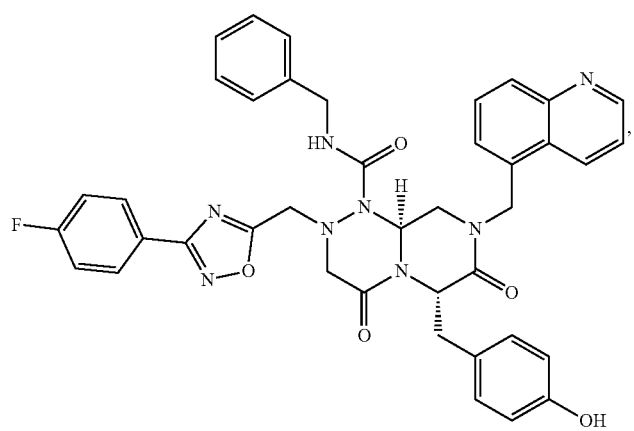
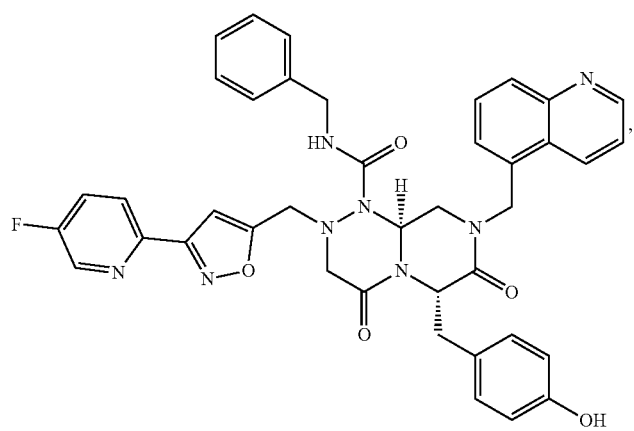
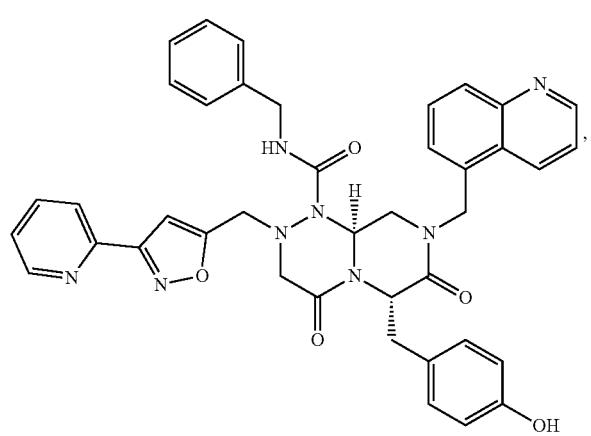
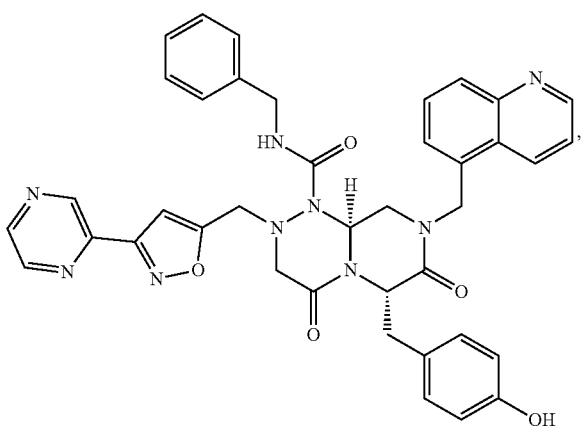
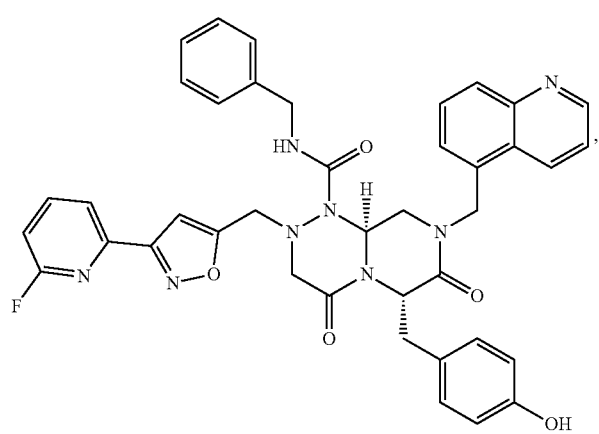

-continued
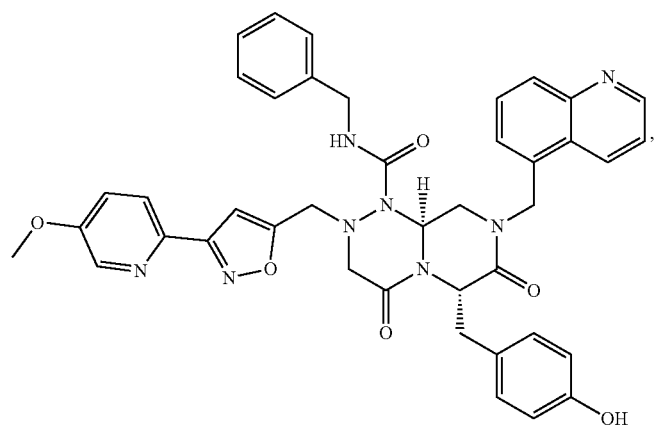
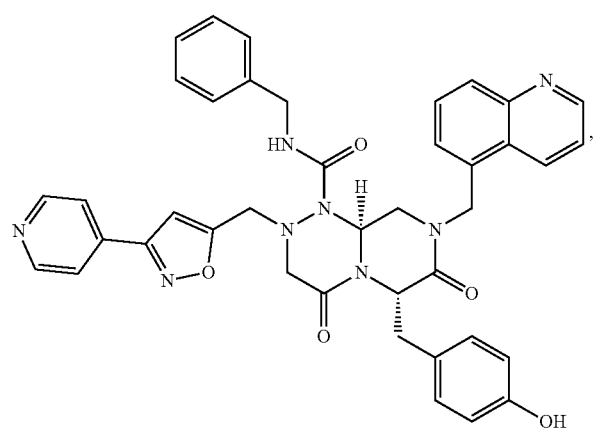
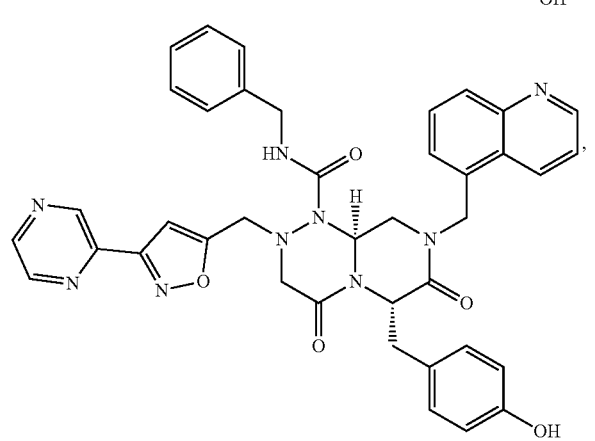
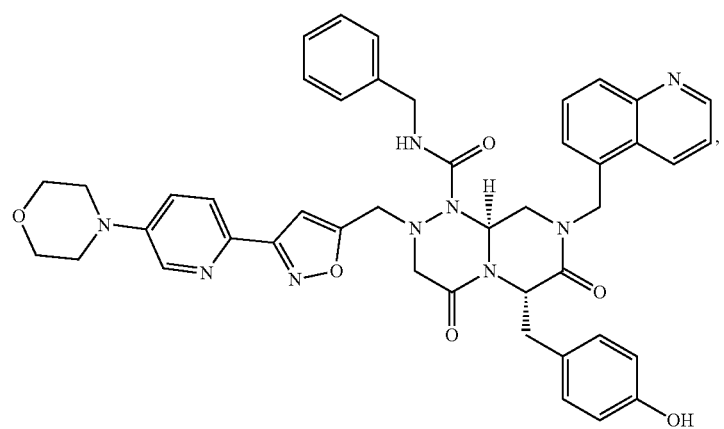

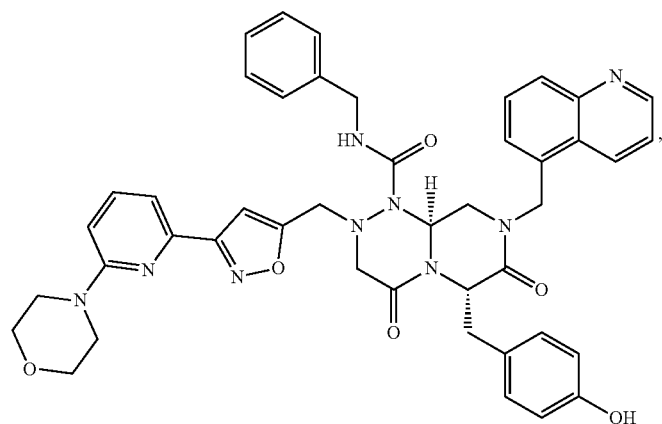
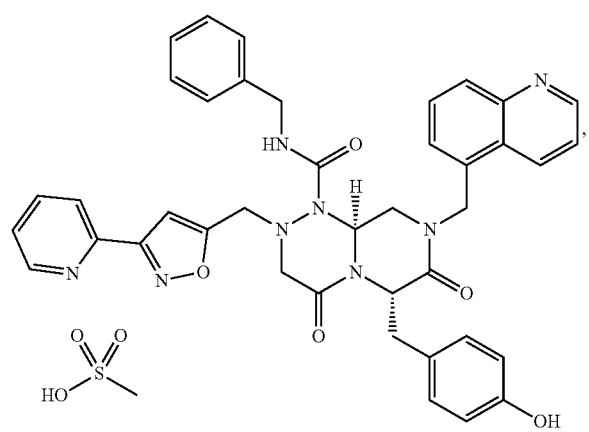
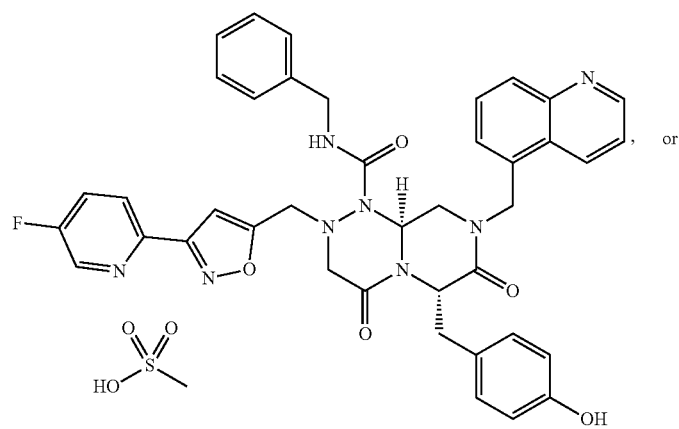

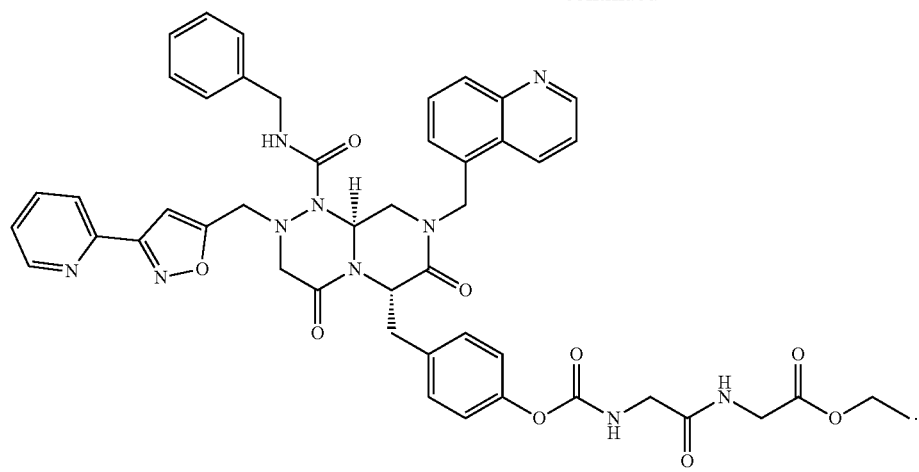

45. The method of claim 22, wherein the pharmaceutically acceptable salt is a p-toluenesulfonate.

46. The method of claim 31, wherein the pharmaceutically acceptable salt is a p-toluenesulfonate.

47. The method of claim 33 or claim 36, wherein the ester of the alkyl acid or of the fatty acid is selected from:

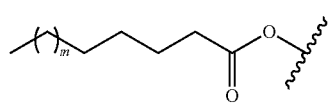

wherein m is 1 to 14,

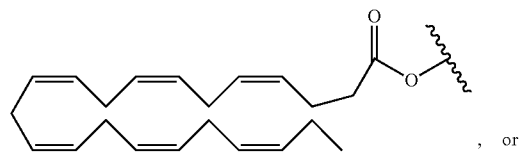, or

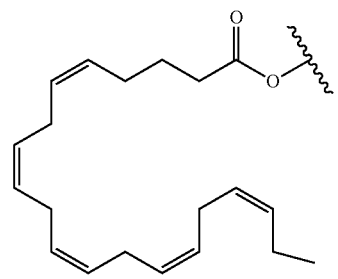

48. The method of claim 33 or claim 36, wherein R is a bicyclic aryl selected from naphthyl, quinolinyl, isoquinolinyl, quinoxaline, phthalazine, quinazoline, cinnoline, naphthyridine, or substituted variants thereof.

49. The method of claim 48, wherein the compound is of the formula (Ib):

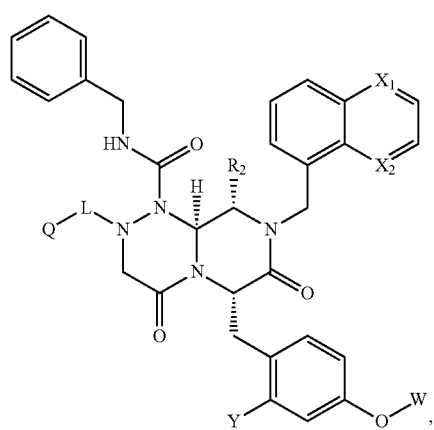

(Ib)

wherein $X_1$ and $X_2$ are independently selected from: N, or —CH.

50. The method of claim 49, wherein:
L is —CH$_2$—;
Q is

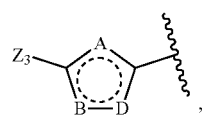

wherein A, B, and D are independently selected from O, S, N, or —CH.

51. The method of claim 50, wherein A is —CH, B is N, and D is O ($Z_3$-isoxazole-).

52. The method of claim 51, wherein $Z_3$ is selected from aryl or heteroaryl, each of which is substituted by 0-4 substituents independently selected from hydrogen, deuterium, halogen, $C_1$-$C_4$ alkyl, $C_1$-$C_3$ haloalkyl, —OH, —OC$_1$-C$_6$ alkyl, —OC$_1$-C$_6$ alkyl-C(O)NH—OH, —NH$_2$, —C(O)NH—C$_1$-C$_6$ alkyl-heteroaryl, —NHC(O)C$_1$-C$_6$ alkyl-C(O)NH—OH, heteroaryl, cycloalkyl, heterocycloalkyl, or a nitrogen-bonded cycloalkyl or heterocycloalkyl, —NHC$_1$-C$_4$ alkyl, or —N(C$_1$-C$_4$ alkyl)$_2$.

53. The method of claim 52, wherein Z$_3$ is selected from aryl or heteroaryl, substituted by 0-4 substituents independently selected from hydrogen, deuterium, halogen, C$_1$-C$_4$ alkyl, C$_1$-C$_3$ haloalkyl, —OH, —OC$_1$-C$_6$ alkyl, or nitrogen-bonded heterocycloalkyl.

54. The method of claim 53, wherein the compound is:

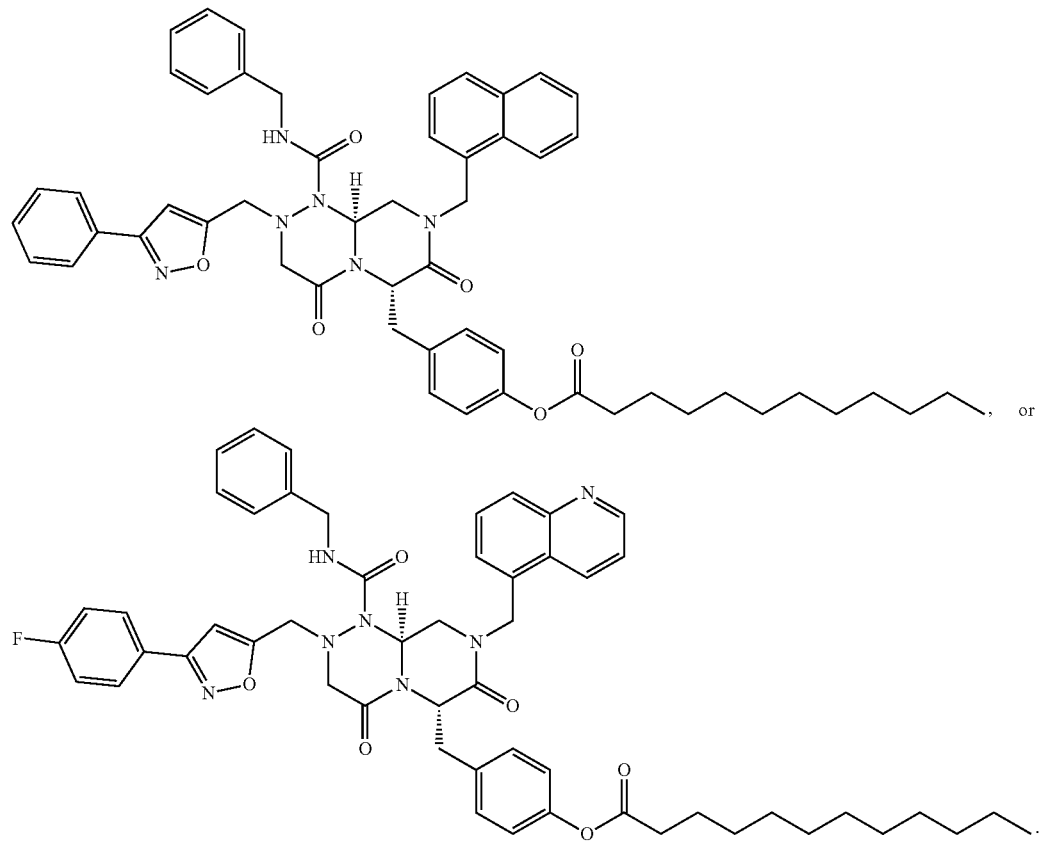

* * * * *